US009757480B2

(12) United States Patent
Abraham et al.

(10) Patent No.: US 9,757,480 B2
(45) Date of Patent: Sep. 12, 2017

(54) RADIOPAQUE EMBOLIC PARTICLES

(75) Inventors: Robert J. Abraham, Halifax (CA); Sharon Kehoe, Halifax (CA); Daniel Boyd, Halifax (CA)

(73) Assignee: ABK Biomedical Incorporated, Halifax (CA)

( * ) Notice: Subject to any disclaimer, the term of this patent is extended or adjusted under 35 U.S.C. 154(b) by 152 days.

(21) Appl. No.: 13/980,316

(22) PCT Filed: Jan. 27, 2012

(86) PCT No.: PCT/IB2012/000341
§ 371 (c)(1),
(2), (4) Date: Jul. 18, 2013

(87) PCT Pub. No.: WO2012/101524
PCT Pub. Date: Aug. 2, 2012

(65) Prior Publication Data
US 2013/0295020 A1 Nov. 7, 2013

Related U.S. Application Data

(60) Provisional application No. 61/437,566, filed on Jan. 28, 2011.

(51) Int. Cl.
*A61K 49/08* (2006.01)
*A61K 33/00* (2006.01)
*A61K 33/08* (2006.01)
*A61K 33/24* (2006.01)
*A61K 49/04* (2006.01)
*A61K 9/14* (2006.01)

(52) U.S. Cl.
CPC ............. *A61K 49/08* (2013.01); *A61K 9/143* (2013.01); *A61K 33/00* (2013.01); *A61K 33/08* (2013.01); *A61K 33/24* (2013.01); *A61K 49/0419* (2013.01)

(58) Field of Classification Search
CPC ........ A61K 33/24; A61K 49/08; A61K 9/143; A61K 33/08; A61K 33/00; A61K 49/0419; A61K 2300/00
USPC ...................... 424/9.322, 497, 9.32; 514/770
See application file for complete search history.

(56) References Cited

U.S. PATENT DOCUMENTS

| | | | |
|---|---|---|---|
| 5,618,763 | A | 4/1997 | Frank et al. |
| 6,054,400 | A | 4/2000 | Brink et al. |
| 6,335,384 | B1 | 1/2002 | Evans et al. |
| 2001/0024662 | A1 | 9/2001 | Yang |
| 2002/0119202 | A1* | 8/2002 | Hunter et al. ............... 424/501 |
| 2004/0247849 | A1 | 12/2004 | Truckai |
| 2008/0255265 | A1 | 10/2008 | Hoescheler et al. |
| 2010/0021550 | A1 | 1/2010 | Li et al. |

FOREIGN PATENT DOCUMENTS

| | | |
|---|---|---|
| CA | 2154990 A1 | 2/1996 |
| CN | 1128246 | 8/1996 |
| CN | 1241169 | 1/2000 |
| CN | 101484396 | 7/2009 |
| EP | 0695726 A1 | 2/1996 |
| EP | 0802890 A1 | 10/1997 |
| EP | 0802890 B1 | 9/2001 |
| EP | 1547572 A1 | 6/2005 |
| FR | 2908891 A1 | 5/2008 |
| JP | H10-512227 | 11/1998 |
| JP | 2005350325 A | 12/2005 |
| JP | 2007-515450 | 6/2007 |
| JP | 2007-526202 | 9/2007 |
| WO | 99/37287 A1 | 7/1999 |
| WO | WO 01/58720 A1 | 8/2001 |
| WO | 2004074199 A1 | 9/2004 |
| WO | 2007048856 A1 | 5/2007 |
| WO | 2010044413 | 4/2010 |

OTHER PUBLICATIONS

First Examination Report for New Zealand Patent Application No. 613872, Apr. 4, 2014, 2 Pages.
Written Opinion for Singapore Patent Application No. 2013057294, Jun. 19, 2014, 7 Pages.
CN201280015284, Office action, mailed Aug. 21, 2014, 6 pages.
PCT International Search Report and Written Opinion for PCT/IB2012/000341, Sep. 13, 2012, 9 Pages.
Saralidze, K., et al., "New acrylic microspheres for arterial embolization: Combining radiopacity for precise localization with immobilized thrombin to trigger local blood coagulation," Biomaterials, 2007, pp. 2457-2464, vol. 28, No. 15.
Examination Report No. 1 dated Apr. 11, 2016 for corresponding Australian Patent Application No. 2012210256.
Office Action dated Jan. 20, 2015 from corresponding Canadian Patent Application No. 2,825,512.
Office Action dated Dec. 22, 2015 from corresponding Canadian Patent Application No. 2,825,512.
Notice of Reasons for Rejection dated Feb. 15, 2016 from corresponding Japanese Patent Application No. 2013550965, with English translation.
Further Examination Report dated Jul. 24, 2015 from corresponding New Zealand Patent Application No. 613872.
Notice of Acceptance dated Jan. 27, 2016 from corresponding New Zealand Patent Application No. 613872.
Establishment of Report without Response to Written Opinion dated Jan. 5, 2015 from corresponding Singapore Patent Application No. 2013057294.
Notification of Second Office Action dated Jul. 14, 2015 from corresponding Chinese Patent Application No. 201280015284.0, with English translation.
Office Action issued in May 2015 for corresponding Eurasian Patent Application No. 201370170, with English summary.

(Continued)

*Primary Examiner* — Robert Cabral
(74) *Attorney, Agent, or Firm* — Borden Ladner Gervais LLP; David Nauman

(57) ABSTRACT

A radiopaque particulate material one or more of $SiO_2$, $TiO_2$, $La_2O_3$, $Na_2O$ and MgO and useful for embolization which optionally includes therapeutic components that are released in vivo.

27 Claims, 31 Drawing Sheets

(56) References Cited

OTHER PUBLICATIONS

Office Action issued in Sep. 2015 for corresponding Eurasian Patent Application No. 201370170, with English summary.
Notification of Third Office Action dated Jan. 21, 2016 from corresponding Chinese Patent Application No. 201280015284.0, with English translation.
Extended European Search Report dated Jun. 6, 2016 issued on the corresponding European Patent Application No. 12738789.2.
Wu et al., "Melt-derived bioactive glass scaffolds produced by a gel-cast foaming technique", Acta Biomaterialia, vol. 7, No. 4, p. 1807-1816, Nov. 29, 2010.
International Preliminary Report on Patentability for Application No. PCT/IB2012/000341, mailed on Aug. 8, 2013, 7 pages.
Office Action dated Oct. 17, 2016 issued on the corresponding Chinese application No. 201280015284 with English translation.
Office Action dated Oct. 25, 2016 issued on the corresponding Canadian application No. 2,825,512.
Office Action dated Sep. 15, 2016 issued on the corresponding Japanese application No. 20130550965 with English translation.

* cited by examiner

Key
1  cranial end
2  0.2 ml injections of polar extract
3  0.2 ml injections of non-polar extract
4  0.2 ml injections of polar solvent control
5  0.2 ml injections of non-polar solvent control
6  caudal end

RADIOPAQUE EMBOLIC PARTICLES

CROSS-REFERENCE TO RELATED APPLICATIONS

This application is the 35 USC §371 national stage entry of PCT/IB2012/000341 and claims the benefit of U.S. Provisional Application 61/437,566 filed on Jan. 28, 2011, which is hereby incorporated by reference in its entirety for all purposes.

FIELD OF THE INVENTION

The invention relates to particulate material that is radiopaque and suited for performing embolization.

BACKGROUND

Polymeric particles are frequently employed by interventional radiologists for the selective occlusion of blood vessels in the treatment of (but not limited to) hypervascular tumors such as leiomyoma uteri and vascular anomalies such as vascular malformations. However, current state of the art particles are beset with numerous drawbacks which limit market penetration for such products. The drawbacks include that the particles are not radiopaque. Thus, the clinician is not able to monitor placement of the particles radiographically. The result is that complications of embolization, such as reflux with non-target embolization and through embolization are not detectable. Current approaches to this problem include dispersing the particles in a medium that includes a contrast agent that is visible radiographically. This leads to its own complications however. Contrast-induced nephropathy occurs in about seven percent of patients exposed to contrast agents. Contrast-induced nephropathy is characterized by acute renal injury which can lead to renal failure. Exposure to contrast agents is the third most common cause of hospital acquired renal failure. Additionally, the degradation of the particles currently in use cannot be controlled. The ability to choose particles that are either non-degradable or that have differing degrees of degradability allows for more treatment options for the various lesions that are amenable to embolization. Use of particles that degrade with time may allow for revascularization of the occluded blood vessel after the treated lesion is gone resulting in recovery of blood flow to normal tissue. This would be desired in instances such as the treatment of gastrointestinal hemorrhage. In other instances, use of a non-degradable particle prevents revascularization of the underlying vessel. This would be desired in vascular lesions such as vascular malformations.

Thus, what are needed are improved embolic particles that limit the addition of a contrast agent for radiographic imaging and whose degradation may be controlled.

SUMMARY

A particulate material comprising one or more of $TiO_2$, $La_2O_3$, $Na_2O$ and $MgO$ or $SrO$ is provided. In one embodiment, the particulate material comprises: 0.4-0.7 mole fraction $SiO_2$; 0.04-0.7 mole fraction $TiO_2$; 0.04-0.5 mole fraction $La_2O_3$; 0.03-0.3 mole fraction $MgO$; and 0.03-0.3 mole fraction $Na_2O$. In one embodiment, $MgO$ is present at 0.05 to 0.2 mole fraction. The particulate material may optionally comprise $SrO$. When $SrO$ is included, the $MgO$ and the $SrO$ together can be present at 0.05-0.3 mole fraction. Alternatively, the $MgO$ and the $SrO$ together are present at 0.05-0.2 mole fraction. The $La_2O_3$ can be present at 0.04 to 0.4 mole fraction or 0.04 to 0.3 mole fraction. The $TiO_2$ may be present at 0.04 to 0.3 mole fraction or 0.04 to 0.2 mole fraction. The $SiO_2$ may be present at 0.4-0.6 mole fraction or 0.4-0.5 mole fraction. The $Na_2O$ is present at 0.03-0.2 mole fraction or 0.03-0.15 mole fraction.

In some aspects, the particulate material is radiopaque.

In some aspects, the particulate material is biocompatible.

The particulate material is optionally degradable in vivo. In one embodiment the particulate material degrades substantially in more than six months. Alternatively the particles are non-resorbable.

In some aspects, the particulate material releases therapeutic components under physiological conditions.

In some aspects, the particulate material has a Q-speciation of $Q^1$-$Q^3$ or about $Q^2$.

In some aspects, the particles of the particulate material have an average diameter of 45-1180 μm, 200-1000 μm, 100-300 μm, 300-500 μm, 500-710 μm or 710-1000 μm.

In some aspects, the particulate material comprises no more than 0.1 mole fraction aluminosilicates, phosphates or a combination thereof.

The particulate material optionally includes a polymeric coating or is dispersed within a polymeric matrix. In one embodiment, the polymer comprises poly(lactic-co-glycolic acid). Additionally or alternatively, the polymer comprises a poloxamer. In one embodiment the poloxamer is Pluronic F127. The polymer optionally comprises therapeutic components which are released under physiological conditions.

In one aspect, the particulate material of any of the previous claims is used for vascular occlusion. The vascular occlusion may be for treatment of vascular malformations, organ ablation, chemoembolization, treatment of hemorrhage or uterine fibroid embolization.

DETAILED DESCRIPTION

Figure 1:
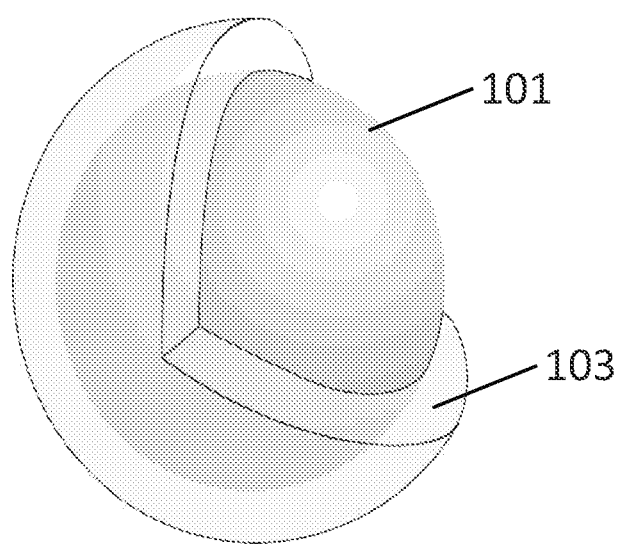
FIG. 1 illustrates a particle according to one embodiment.

The particles of the particulate material comprise a core and an optional compressible shell/matrix. The core comprises one or more of $SiO_2$, $La_2O_3$, $Na_2O$, MgO and SrO. The optional compressible shell/matrix comprises a biocompatible polymer. Additional provided particulate materials have a core comprising one or more of $SiO_2$, $La_2O_3$, $TiO_2$, ZnO, MgO, $Na_2O$, SrO, and CaO. In some embodiments, the particulate material is substantially free of phosphates and aluminosilicates. In some embodiments, the particulate material comprises no more than 0.1 mole fraction aluminosilicates, phosphates or a combination thereof. Surprisingly, the particulate materials are biocompatible and yet do not require phosphates or aluminosilicates.

Core

In one embodiment, the particulate material has the properties of a glass ceramic. In such an embodiment, the components make up a network, which can be amorphous or crystalline. Components include $SiO_2$, $La_2O_3$, $TiO_2$, ZnO, MgO, $Na_2O$, SrO, and CaO. Modifying the amounts of the various core components (as well as the ratios of components to each other) allows for tuning the characteristics of the material to its intended use.

Network Components $La_2O_3$ is present at a mole fraction of 0.04 to 0.5. In another embodiment, $La_2O_3$ is present at 0.04 to 0.4 mole fraction. In another embodiment, $La_2O_3$ is present at 0.04 to 0.3 mole fraction. $La_2O_3$ provides radiopacity to the particulate material. Lanthanum has been used for decades in dental applications as a radiopacifiying agent in glass ceramics and dental composites. The $La_2O_3$ provides superior radiopacity over current state of the art embolic agents. The release of $La^{3+}$ as the material degrades has the additional potential benefit of providing therapeutic benefit. The $La^{3+}$, for example, facilitates anoikis of certain cancers and is thus beneficial when the intended use of the particulate material is to initiate anoikis of those cancers. For those uses the amount of lanthanum is tuned for that purpose.

Another component of the particulate material is titanium. $TiO_2$ is present in 0.04 to 0.7 mole fraction. In some embodiments, $TiO_2$ is present at 0.04 to 0.3 mole fraction. In some embodiments, $TiO_2$ is present at 0.04-0.2 mole fraction. Titanium is thrombogenic and its inclusion in the particulate material increases thrombogenicity around the particles in vivo. The thrombogenicity of the particulate material may be tuned by the amount of $TiO_2$ present. Depending on the intended application, a greater or lesser amount of thrombogenicity is required.

A third component of the particulate materials is silicon. $SiO_2$ is present in the particulate material at 0.4-0.7 mole fraction. In one embodiment, the $SiO_2$ is present at 0.4-0.6 mole fraction. In yet another embodiment, the $SiO_2$ is present at 0.4-0.5 mole fraction.

Magnesium is present in the particulate material in the form of MgO at a mole fraction of 0.03 to 0.3. In one embodiment, the MgO is present at 0.03 to 0.2 mole fraction. In alternative embodiments, MgO is present at 0.05 to 0.3 pr 0.05 to 0.2 mole fraction. Magnesium is a thrombogenic material and its inclusion in the particulate material increases thrombogenicity around the particles in vivo. Further, magnesium, a metallic element, enhances the imaging qualities of the particulate material and also provides additional control over the structure of the particulate material. In some embodiments, a second alkaline earth metal oxide is also used, SrO. The ratio of MgO to SrO allows tuning the biocompatibility of the particulate material as needed for different applications. For example, increased MgO results in a less stable glass network which would result in faster degradation which is desirable for some applications. Increasing SrO increases radiopacity and so the ratio of MgO to SrO also allows for tuning of this functional aspect of the particulate material.

Sodium imparts degradability to the particulate material. The more sodium present in the particulate material, the more quickly the particulate material degrades in vivo. $Na_2O$ is present in the particulate material at 0.03-0.3 mole fraction. In some embodiments, $Na_2O$ is present in the particulate material at 0.03-0.2 mole fraction. In yet other embodiments, $Na_2O$ is present in the particulate material at 0.03-0.15 mole fraction. In one embodiment, the particles take more than six months to degrade. Particles with this rate of degradation are useful when early recanalization of vessels is undesirable. Examples of such situations include organ ablation (i.e. embolization of native kidneys that are causing hypertension in a dialysis patient or a patient with a kidney transplant) or malignant tumor embolization (i.e hormonally active metastatic disease to the liver such as a carcinoid tumor, renal cell carcinoma, etc).

Additional Components

Additional components having therapeutic properties can be added to the particulate material. In one embodiment such therapeutic components release as a function of in vivo surface modifications to the particle. These components are then released from the particle in the body. The make-up of the network-modifying components is used to control the release of the therapeutic components. Examples of such components include therapeutic ions and chemotherapeutic agents. Therapeutic ions include, for example, $Ca^{2+}$, which aids in coagulation. In one embodiment, calcium is provided in the particle in the form of CaO.

Nature of Core/Particle

In one embodiment, the particulate material is a ceramic. Ceramics are inorganic, non-metallic materials prepared by heating and subsequent cooling. Ceramics are usually formed between metallic and nonmetallic elements, such as, for example, aluminum and oxygen, calcium and oxygen and silicon and nitrogen. Ceramics can have crystalline, partly crystalline or amorphous structures and include ceramic glasses, also referred to as glasses. Other ceramics include enamels, glass-ceramics (glasses containing ceramic crystals), and inorganic cement-type materials (cement, plaster and lime). In one embodiment, the particulate material is a glass. Glass is any solid with a non-crystalline, or amorphous, structure and exhibits a glass transition upon heating.

Q-speciation is known in the art as a system for characterizing glass materials. It is a measure of how many of the oxygens surrounding silicon are bridging oxygens. The superscript, n, in $Q^n$ is higher the more bridging oxygens there are in the tetrahedral units of the network. The superscript n can be from 0 to 4. In one embodiment, the particulate material of the invention has a Q-speciation between $Q^1$ and $Q^3$ with a corresponding network connectivity of between 1 and 3. In one embodiment, the particulate material has a Q-speciation of $Q^2$.

Compressible Shell/Matrix

FIG. 1 illustrates a particle according to one embodiment. The particle includes the core 101 described above and also a compressible shell/matrix 103 of a biocompatible polymer. Such an embodiment is illustrated in FIG. 1. As mentioned previously, the core can also be suspended in a polymer matrix. Possible polymers include poly(lactic-co-glycolic acids) ("PLGA") and poloxamers. In one embodiment, the shell/matrix includes Pluronic F127 available from BASF. This shell/matrix allows for drug elution for therapeutic benefit. Examples include chemoembolization of malignant tumors. Specific examples include hepatocellular carcinoma of the liver. Additional drugs that can be eluted include, for example, thrombogenic agents that enhance the degree of vascular occlusion. The compressibility of the shell/matrix is useful in clinical deployment of the particulate material.

particles can also be used as the initial size of particle for uterine fibroid embolization and most other organ or tumor embolizations. In another alternative embodiment, the particles have an average diameter of 500-710 μm. The 500-710 μm particles are also used in embolization of uterine fibroids. Which size range, 300-500 μm or 500-710 μm, to use for embolization of uterine fibroids depends on other characteristics of the particle. In yet another alternative, the particles have an average diameter of 710-1000 μm and are useful for proximal embolization to reduce the "head pressure" to a site of hemorrhage such as in gastrointestinal hemorrhage or traumatic hemorrhage.

Additional Uses of Particulate Material

The particulate material of the invention may be used for vascular occlusion. In one embodiment, vascular occlusion is used in the treatment of uterine fibroids, vascular malformations and other vascular anomalies or lesions, organ ablation including portal vein embolization, chemoembolization and hemorrhage from any cause.

EXAMPLES

Synthesis of Glass Particulate Materials

Generally, appropriate amounts of analytical grade reagents are weighed out as appropriate and thoroughly mixed by shaking (30 mins) in a plastic container. Each batch of powder is fired at the appropriate temperature (initially 1520° C. for 1 hour) in a platinum crucible. The glass melt is then shock quenched into water. The resulting glass frit is dried in an oven (120° C., 1 day), ground and sieved to retrieve glass powder for subsequent analysis. Tables 1 and 2 show example compositions for particulate materials. Table 2 as appended at the end of the specification.

TABLE 1

13 glass compositions (mol. fraction) formulated using design of experiments. The Network Modifying (NM) components (Ca; Mg; Sr and Na) are kept constant at 0.035 mol. fraction.

| Embolic Designation | Design NC points[a] | | $SiO_2$ | CaO | ZnO | MgO | $La_2O_3$ | SrO | $Ti_2O$ | $Na_2O$ |
|---|---|---|---|---|---|---|---|---|---|---|
| ORP1 | 2 | V | 0.553 | 0.035 | 0.137 | 0.035 | 0.137 | 0.035 | 0.033 | 0.035 |
| ORP2 | 2 | V | 0.570 | 0.035 | 0.240 | 0.035 | 0.000 | 0.035 | 0.050 | 0.035 |
| ORP3 | 2 | V | 0.537 | 0.035 | 0.213 | 0.035 | 0.068 | 0.035 | 0.042 | 0.035 |
| ORP4 | 2 | V | 0.570 | 0.035 | 0.000 | 0.035 | 0.240 | 0.035 | 0.050 | 0.035 |
| ORP5 | 2 | V | 0.562 | 0.035 | 0.188 | 0.035 | 0.068 | 0.035 | 0.042 | 0.035 |
| ORP6 | 2 | V | 0.562 | 0.035 | 0.068 | 0.035 | 0.188 | 0.035 | 0.042 | 0.035 |
| ORP7 | 2 | A-CB | 0.562 | 0.035 | 0.213 | 0.035 | 0.068 | 0.035 | 0.017 | 0.035 |
| ORP8 | 2 | A-CB | 0.570 | 0.035 | 0.000 | 0.035 | 0.290 | 0.035 | 0.000 | 0.035 |
| ORP9 | 2 | A-CB | 0.520 | 0.035 | 0.290 | 0.035 | 0.000 | 0.035 | 0.050 | 0.035 |
| ORP10 | 2 | A-CB | 0.520 | 0.035 | 0.000 | 0.035 | 0.290 | 0.035 | 0.050 | 0.035 |
| ORP11 | 2 | A-CB | 0.570 | 0.035 | 0.290 | 0.035 | 0.000 | 0.035 | 0.000 | 0.035 |
| ORP12 | 2 | A-CB | 0.562 | 0.035 | 0.068 | 0.035 | 0.213 | 0.035 | 0.017 | 0.035 |
| ORP13 | 2 | C | 0.537 | 0.035 | 0.068 | 0.035 | 0.213 | 0.035 | 0.042 | 0.035 |

Size of Particulate Material

The individual particles of the particulate materials are between 45 and 1180 μm in average diameter. Alternatively the particles are between 200 and 1000 μm in average diameter. Various uses for the particles require different sizes of particles. Thus, in one embodiment, the particles have an average diameter of 100-300 μm which are useful for deep tumor necrosis as may be needed in malignant tumor embolization. In another embodiment, the particles have an average diameter of 300-500 μm and are used for treating gastrointestinal or traumatic bleeding. The 300-500 μm The optional compressible shell/matrix are added by a modified emulsification method. PLGA of various molecular weights are supplemented with glass particles at various wt %. PLGA are dissolved in methylene chloride, and then the glass will be added, at the preferred level, into the solution. The mixture is then added, drop-wise, into a stirred PVA solution. Micro-spheres are isolated by filtration, washed with deionized water air dried then vacuum dried. Table 3 provides the make-up of example particulate materials with a polymer coating.

TABLE 3

9 composite variations (wt %.) formulated using design of experiments.
The glass is expressed as a wt. % of the PLGA base.

| Std. | Run. | PLGA | Glass |
|---|---|---|---|
| ORP2 | 1 | 25.00 | 5.00 |
| ORP8 | 2 | 25.00 | 60.00 |
| ORP1 | 3 | 15.00 | 5.00 |
| ORP9 | 4 | 25.00 | 60.00 |
| ORP7 | 5 | 10.00 | 60.00 |
| ORP6 | 6 | 10.00 | 60.00 |
| ORP4 | 7 | 10.00 | 32.50 |
| ORP3 | 8 | 25.0 | 5.00 |
| ORP5 | 9 | 15.0 | 41.67 |

Example 1

Particle Compositions

Particle compositions (mol. fraction) $(0.52-0.57)SiO_2$-$0.035CaO$-$(0.00-0.29)$-$ZnO$-$0.035MgO$-$(0.00-0.188)La_2O_3$-$0.035SrO$-$(0.00-0.05)TiO_2$-$0.035Na_2O$ were synthesized for this work. Analytical grade reagents: silicon dioxide, calcium carbonate, zinc oxide, magnesium oxide, lanthanum (III) oxide, strontium carbonate, titanium dioxide and sodium carbonate (Sigma Aldrich, Canada) were weighed and homogeneously mixed in a plastic container (Nalgene™, Sigma Aldrich, Canada) for 1 hour. Each batch of powder was placed in platinum crucibles (50 mL), then fired (1480° C., 1 hour) using a Bench-Top High Temperature Muffle Furnace (EQ-KSL, MTI Corporation. USA) and shock quenched into water. The resulting frit was dried in an oven (120° C., 1 day), pulverized in an agate planetary mill (Pulverisette 7; Laval Labs Inc., Canada) and sieved through various aperture to produce powder particulates in the following size ranges: <45 µm; 45-212 µm; 212-300 µm; 355-500 µm; >500 µm. All batches of particles produced in this work were subsequently stored in dry dessicators for further evaluation.

Characterization of Particulate Materials
Differential Scanning Calorimetry (DSC)

Generally, DSC is used to determine the onset of the glass transition temperature ($T_g$) for each glass using a differential scanning calorimeter (DSC). Temperature intervals of 258.15° C. (up to 725° C.) are employed in an air atmosphere with alumina (or other appropriate reference) in a matched platinum crucible. The tolerance of the DSC used is on the order of 2%.

Example 2

Figure 2:
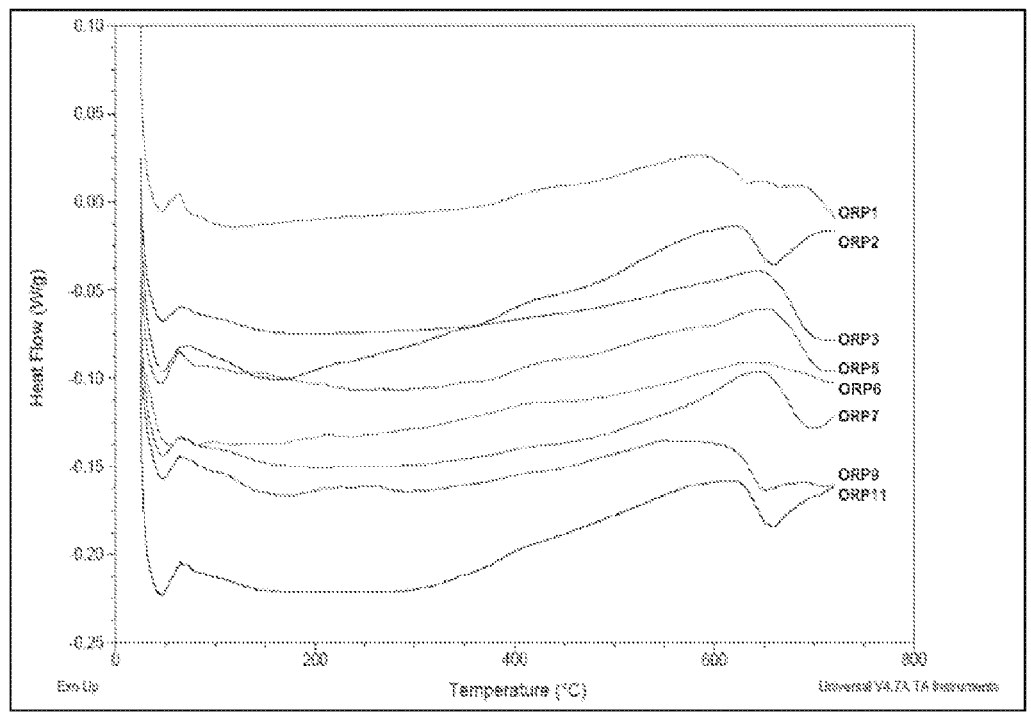
FIG. 2 are DSC traces for eight particles.

DSC analysis of the particles made in Example 1 was performed to obtain the values of the glass transition temperature ($T_g$). Samples (~80 mg) were heated in a platinum crucible in a nitrogen environment alongside an empty reference crucible. A standard reference material is already pre-selected for a given temperature range. $T_g$ was measured in a differential scanning calorimeter (DSC; TA Instruments-DQ200) between 25° C. and 725° C. at temperature intervals of 258.15° C. DSC traces for the eight particles (ORP1-3, ORP5-7, ORP9 and ORP11) are shown in FIG. 2. Table 4 is an abstracted ANOVA table for the $T_g$ reduced linear mixture polynomial model. A tabulated comparison between observed and calculated $T_g$ behaviors for each material composition, is provided for in Table 5, as based on the regression model developed in terms of L-Pseudo component coding. The final mathematical model in terms of L-Pseudo components is shown as follows in Equation 1:

$$T_g(°C.) = +634.82ZnO + 833.28La_2O_3 + 677.195SiO_2 + 699.01TiO_2 \quad \text{Eqn. 1}$$

TABLE 4

| Response (sig./non sig.) | SD | Mean | F Value | Prob. > F Model | $R^2$ | Adj-$R^2$ | Pred-$R^2$ | CV % | Adq. Prec. |
|---|---|---|---|---|---|---|---|---|---|
| $T_g$ (° C.) significant | 5.05 | 662.27 | 31.54 | 0.0309 | 0.9793 | 0.9482 | 0.7089 | 0.76 | 10.728 |

TABLE 5

Residuals of the $T_g$ study.

| Embolic Composition | ORP2 | ORP3 | ORP5 | ORP7 | ORP9 | ORP11 |
|---|---|---|---|---|---|---|
| Calculated $T_g$ (° C.) | 646.08 | 680.971 | 684.087 | 681.573 | 639.845 | 641.05 |
| Experimental $T_g$ (° C.) | 643.65 | 680.20 | 688.94 | 677.49 | 640.23 | 643.09 |
| Residual (Difference) | 2.43 | −0.78 | 4.85 | −4.08 | 0.39 | 2.04 |

X-Ray Diffraction (XRD)

Generally, XRD is employed to validate the amorphous nature of the glasses. Powdered samples of each glass are pressed to form discs (Ø32 mm×3 mm). Diffraction patterns are collected using an X-ray Diffraction Unit with monochromated CuKα (λ=1.54060 A) radiation at 40 KV and 35 mA. The scanning angle range (2θ) is performed from 10° to 70° with a step size 0.033423° and step time of 59.69 s.

Example 3

X-ray diffraction (XRD) measurements for the particles were performed using an INEL CPS-120 diffractometer with a curved position sensitive detector coupled to an X-ray generator (40 kV; 35 mA) and equipped with a Cu target X-ray tube. Samples were prepared by pressing the selected particle particles (45-212 µm) into hollow square steel wafers. A monochromator in the incident beam path limits the wavelengths striking the sample to Cu Kα1,α2. The X-ray beam is incident upon the sample at approximately 6° and the curved position sensitive detector collects all scattered X-rays in the scan angle range 10°<2θ<110°. Collection time for the XRD spectra is 1800 seconds. The powder samples were placed on the INEL's x-y translating stage that allows measurement and move operations to be sequentially programmed.

Figure 3A:
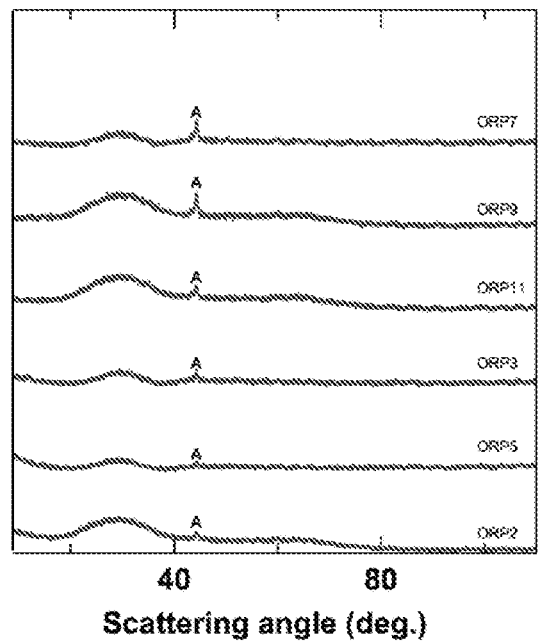
FIG. 3 are XRD patterns for synthesized exemplary particles.
Figure 3B:
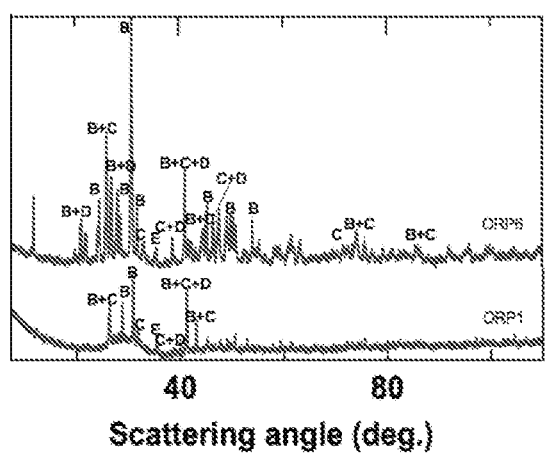

FIG. 3 illustrates XRD patterns for each material synthesized (A) glasses ORP 2,3,5,7,9,11 and (B) ORP 1 and 6. The x axis denotes the scattering angle as measured in degree 2-theta and the y-axis in arbitrary units. Table 6 provides the legend for phase identification.

TABLE 6

| Peak Identifier | JCPDS Card No. | Phase Identifier | Chemical Formula | Present in Composition: |
|---|---|---|---|---|
| B | 00-050-0522 | Strontium-Lanthanum-Titanium oxide | $Sr_3La_2Ti_2O_{10}$ | ORP1,6 |
| C | 00-042-0423 | Perovskite, Calcium Titanium Oxide | $CaTiO_3$ | ORP6 |
| D | 00-049-1433 | Titanium oxide | $TiO_2$ | ORP6 |
| E | 00-039-0190 | Zinc-Titanium oxide | $ZnTiO_3$ | ORP1 |

Surprisingly $T_g$ for these complex multi-component systems is increased by increasing any of the four compositional variants, with its level of statistical significance for the compositional variants following the order: $La_2O_3 > TiO_2 > SiO_2 > ZnO$. One might have expected that only increasing $SiO_2$ content would lead to increases in $T_g$. Interestingly, with a decrease in $T_g$ attributed to the formation of a weaker glass network, the strongest to weakest networks formed for the series of glasses herein therefore, follows the order: ORP5 > ORP3 > ORP7 > ORP2 > ORP11 > ORP9.

Network Connectivity

Example 4

The network connectivity (NC) of each composition was calculated using Equation 2 and the molar compositions of the glass.[1,2] The results are shown in Table 1.

$$NC = \frac{\text{No. BOs} - \text{No. NBOs}}{\text{Total No. Bridging species}} \qquad \text{Eq. 2}$$

Wherein NC=Network Connectivity; BO=Bridging Oxygens and NBO=Non-Bridging Oxygens Generation and Application of Mathematical Models Using a Design of Experiments (DoE) Approach To estimate the coefficients of a second order canonical Scheffé polynomial[3,4], a quadratic user-defined design with thirteen experiments representing different compositional variants (design points) within a defined domain (design space) was constructed using Design-Expert 8.0.4 software (Stat-Ease, Inc.). These design points were determined based on the constrained ranges for each composition: with six experiments set at the extreme vertices; a further six investigating axial check-blends and one overall centroid within the defined design space. These points are in clear agreement with Scheffé's proposal that the interesting points of a domain are at its tops, at the middle of the sides, at the middle of the faces and its centre of gravity (See Table 1). With the mixture design method, an equation is obtained. This formula connects Y, with the four compositional factors ($ZnO$, $La_2O_3$, $SiO_2$ and $TiO_2$, noted respectively as $X_1$, $X_2$, $X_3$ and $X_4$).

The ordinary second-order Scheffé (linear) polynomial equation fitted for Magic Angle Spinning-Nuclear Magnetic Resonance (MAS-NMR) spectroscopy and DSC responses (chemical shift and line width) is:

$$Y_A = \beta_1 X_1 + \beta_2 X_2 + \beta_3 X_3 + \beta_4 X_4 + e \qquad \text{Eq. 3}$$

where $X_1$ to $X_4$ represent the compositional factors, $\beta_{1-4}$ coefficients represent the effect of the individual compositional factors $X_{1-4}$. e is called residual, this value is the difference between calculated and experimental values for each selected glass. It is equal to 0 if the number of retained glasses is the same as the number of coefficients in the formula. In the case of a number of chosen glasses higher than the number of coefficients, residual has a different value for each experiment.

The canonical Scheffé second-order polynomial equation fitted for density and cell viability responses is:

$$Y = \beta_1 X_1 + \beta_2 X_2 + \beta_3 X_3 + \beta_4 X_4 + \beta_{12} X_1 X_2 + \beta_{13} X_1 X_3 + \beta_{14} X_1 X_4 + \beta_{23} X_2 X_3 + \beta_{24} X_2 X_4 + \beta_{123} X_1 X_2 X_3 + \beta_{124} X_1 X_2 X_4 + \beta_{134} X_1 X_3 X_4 + \beta_{234} X_2 X_3 X_4 + e \qquad \text{Eq. 4}$$

where $X_1$ to $X_4$ represent the compositional factors, $\beta_{1-4}$ coefficients represent the effect of the individual compositional factors $X_{1-4}$; $\beta_{12-24}$, are the coefficients of regression which represent the effects of two-way interactions between the compositional factors; $\beta_{123-234}$, are the coefficients of regression which represent the effects of three-way interactions between the compositional factors and e is the residual.

From the estimated coefficients of a quadratic model presented in pseudo and actual values, the effect of each component can be derived. All mixture experiment models were developed relating the response variables to proportions of pseudo-components. Pseudo-component proportions ($z_i$) are calculated as:

$$z_i = (x_i - L_i)/(1 - \Sigma L) \qquad \text{Eq. 5}$$

where $x_i$ stands for the original component proportions, $L_i$ stands for the lower bound constraint (limit) for the $i^{th}$ component, L stands for the sum of all lower bound constraints (limits) for all components in the design, and 1 represents the mixture total.

The pseudo-components are combinations of the original (actual) components, which rescale the constrained composition region so that the minimum allowable proportion of each pseudo-component is zero. This transformation provides for estimating model coefficients more precisely compared to using the actual component system, and as such the coefficients derived based on the pseudo-component scaling is referred to in the context of the discussion to follow. Model validity, in terms of experimental versus calculated data points and graphical representation (contour plots) however, is presented in terms of actual component coding.

If several response characteristics $y_1$, $y_2$, ..., $y_n$ have been modeled in the proportions of the same set of q components, where in the composition space the best overall set of properties are obtained by implementing the desirability function approach. Using the models, which are based on the response characteristics, compositions for particulate materials having desired properties for a particular purpose can be determined.

True Densities

Example 5

Figure 4A:
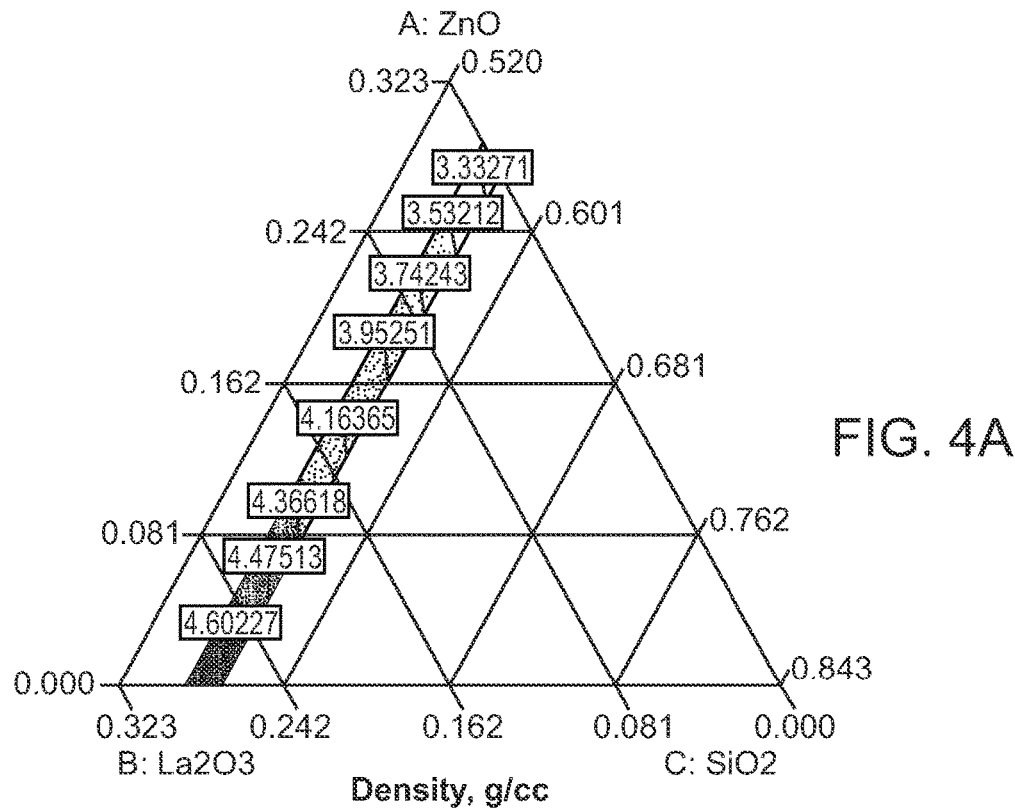
FIG. 4 are contour plots for synthesized exemplary particles.
Figure 4B:
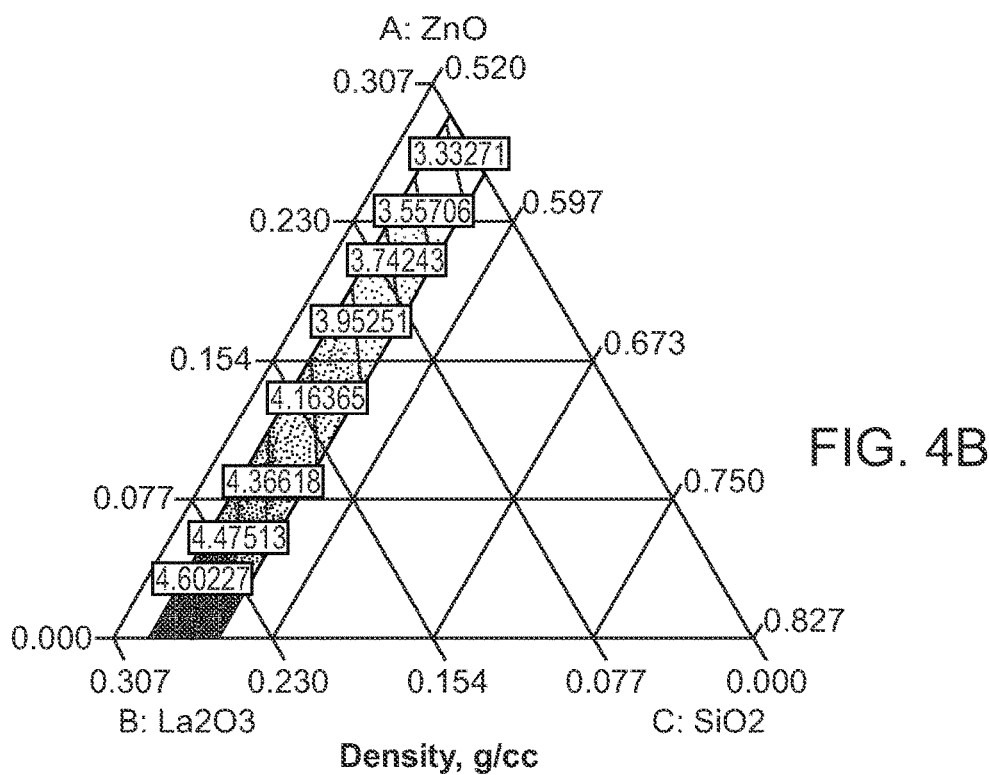
Figure 4C:
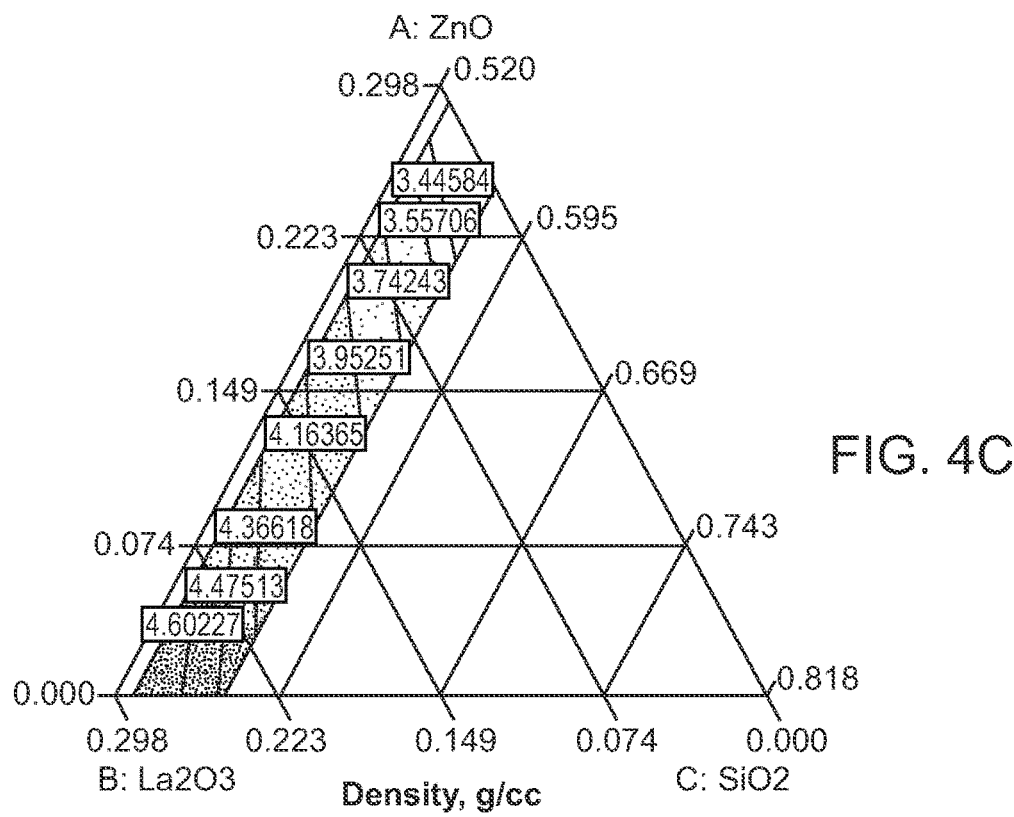
Figure 4D:
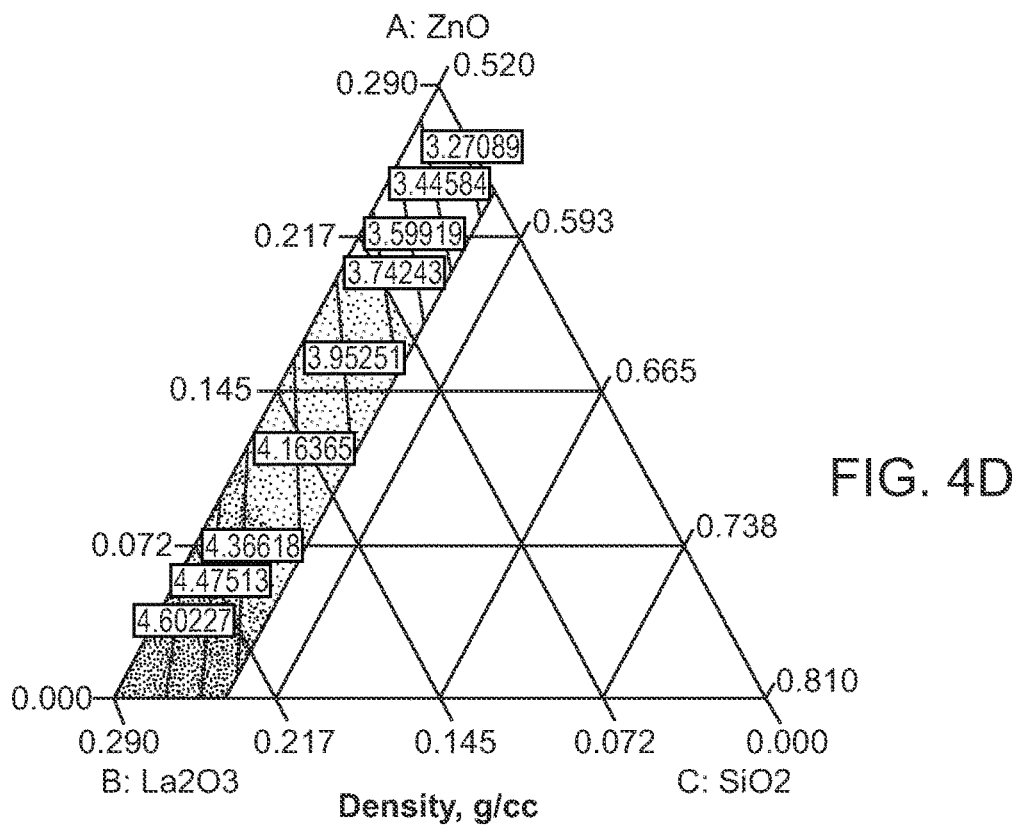

The true densities were measured using a helium pycnometer (AccuPyc 1340, Micromeritics) for all the particles synthesized herein and, also for the commercial control material: Contour™ (PVA particulates). Results are representative of an average of five recorded measurements. FIGS. 4A and 4B are resulting contour plots showing the compositional-interaction effects on the experimental particles density (g/cc) at four various additions of Ti (0.017, 0.033, 0.042 and 0.05 mol.) in actual component coding. (A) is Ti: 0.017 mol. fraction; (B) is Ti: 0.033 mol. fraction; (C) is Ti: 0.042 mol. fraction; and (D) is Ti: 0.050 mol. fraction.

Table 7 illustrates final regression equations in terms of L_Pseudo (1); Actual components (2) and $R^2$ values; and summarized ANOVA for density. The ANOVA data demonstrates that the model adequately predicts the characteristics of the particulate material.

$TiO_2$ (0.5 mol. fraction) content) may adversely affect the final cell viability obtainable; by reducing it from 84 to 61%, respectively. Interestingly, density in the range of 3.5 g/cc ($\pm 0.3$) (for ORP2, 3 and 5) was also representative of the top three compositional variations in terms of cell viabilities (86% ($\pm 5$) attainable.

TABLE 7

| Response | Regression Models | Summarized ANOVA ||||||
|---|---|---|---|---|---|---|---|
| | | $R^2$ | $R^2_{adj.}$ | $R^2_{pred.}$ | Prob > F | CV (%) | Adeq. Prec. |
| Density (g/cc) | 1  +3.39ZnO + 5.12$La_2O_3$ + 2.43$SiO_2$ + 2.92$TiO_2$ + 1.07ZnO * $La_2O_3$<br>2  +5.65559ZnO + 10.72595$La_2O_3$ + 2.82345$SiO_2$ + 4.26905$TiO_2$ + 9.211775ZnO * $La_2O_3$ | 0.9989 | 0.9975 | 0.9859 | <0.0001 | 0.55 | 69.809 |

Table 8 is a summary of the significant (positive and negative) main, interaction and quadratic compositional factors (ranked highest to lowest) and its effect on increasing density; where ↑ denotes an increase and ↓ a decrease. Based on actual component coding.

TABLE 8

| Ranking of Compositional Factors | Density Response |
|---|---|
| 1 | ↑$La_2O_3$ |
| 2 | ↑ZnO |
| 3 | ↑$TiO_2$ |
| 4 | ↑$SiO_2$ |
| 5 | ↑ZnO*$La_2O_3$ |

As illustrated, density may be increased by increasing any of the four compositional variants in the order $La_2O_3$>ZnO>$TiO_2$>$SiO_2$. Interestingly, increasing the interaction of ZnO and $La_2O_3$ (fifth most influencing factor) may result in an increase in material density, a feature which would not have been predicted but which the disclosed models do predict for the disclosed compositions. The lowest levels of density achieved (3.2 g/cc (ORP2) and 3.3 (ORP11)) in the design matrix tested, demonstrate how a slight variation in compositional variants from ORP2 to ORP 11 (increased ZnO (0.05 mol. fraction) and reduced Specific Surface Area Determination $N_2$ adsorption/desorption will be determined using the Brunauer-Emmett-Teller (BET) method to determine the specific surface area (SSA) and porosimetry of the prepared glass powders. Glass samples (~0.15 g±0.05 g) will be placed under a nitrogen atmosphere at 77.35 K with an equilibration interval of 10 s.

Example 6

The theoretical external specific surface areas for the particle particulates and Contour™ were calculated according to the following equation[5], under the assumption of spherical particulate morphology $$A = \frac{6}{\rho d}. \qquad \text{Eq. 6}$$

Table 9 provides specific surface area measurements (45 micron (Lower Level, LL) and 212 micron (Upper Level, UL).

TABLE 9

| Sample ID | Density (g/cc) | SD (g/cc) | PD (LL) cm | PD (UL) cm | SSA (LL) $cm^2/g$ | SSA (UL) $cm^2/g$ |
|---|---|---|---|---|---|---|
| ORP1 | 4.09 | 0.002 | 0.045 | 0.212 | 32.600 | 6.920 |
| ORP2 | 3.17 | 0.001 | 0.045 | 0.212 | 42.048 | 8.925 |
| ORP3 | 3.77 | 0.001 | 0.045 | 0.212 | 35.395 | 7.513 |
| ORP5 | 3.70 | 0.002 | 0.045 | 0.212 | 36.075 | 7.657 |
| ORP6 | 4.29 | 0.001 | 0.045 | 0.212 | 31.087 | 6.599 |
| ORP7 | 3.73 | 0.002 | 0.045 | 0.212 | 35.737 | 7.586 |
| ORP9 | 3.32 | 0.001 | 0.045 | 0.212 | 40.136 | 8.520 |
| ORP11 | 3.25 | 0.003 | 0.045 | 0.212 | 41.038 | 8.711 |
| Contour | 1.77 | 0.003 | 0.045 | 0.212 | 75.406 | 16.006 |

TABLE 9-continued

| Sample ID | Density g/m$^3$ | Density SD g/m$^3$ | PD (LL) m | PD (UL) m | SSA (LL) m$^2$/g | SSA (UL) m$^2$/g | 1 m$^2$ g | 1 cm$^2$ g |
|---|---|---|---|---|---|---|---|---|
| ORP1 | 4090000 | 2000 | 0.000045 | 0.000212 | 0.033 | 0.007 | 144.51 | 0.14 |
| ORP2 | 3171000 | 1000 | 0.000045 | 0.000212 | 0.042 | 0.009 | 112.04 | 0.11 |
| ORP3 | 3767000 | 1000 | 0.000045 | 0.000212 | 0.035 | 0.008 | 133.10 | 0.13 |
| ORP5 | 3696000 | 2000 | 0.000045 | 0.000212 | 0.036 | 0.008 | 130.59 | 0.13 |
| ORP6 | 4289000 | 1000 | 0.000045 | 0.000212 | 0.031 | 0.007 | 151.54 | 0.15 |
| ORP7 | 3731000 | 2000 | 0.000045 | 0.000212 | 0.036 | 0.008 | 131.83 | 0.13 |
| ORP9 | 3322000 | 1000 | 0.000045 | 0.000212 | 0.040 | 0.009 | 117.38 | 0.12 |
| ORP11 | 3249000 | 3000 | 0.000045 | 0.000212 | 0.041 | 0.009 | 114.80 | 0.11 |
| Contour ™ | 1768200 | 3000 | 0.000045 | 0.000212 | 0.075 | 0.016 | 62.48 | 0.06 |

Scanning Electron Microscopy

Example 7

For scanning electron microscopy (SEM) observations, powder samples (particle size range: 355-500 μm) were mounted onto 10 mm diameter×3 mm high Al stubs and coated with ~27 nm platinum using a gold-sputter coater (SC7640, Fisons Instruments). The samples were subsequently transferred to the chamber of a Hitachi S-4700 FEG-SEM equipped with an Oxford Inca energy dispersive x-ray spectroscopy (EDS) system for morphological and chemical analysis. An accelerating voltage of 5.0 kV and a working distance of 11-12 mm were used with the lower secondary electron (SE) detector.

Figure 5A:
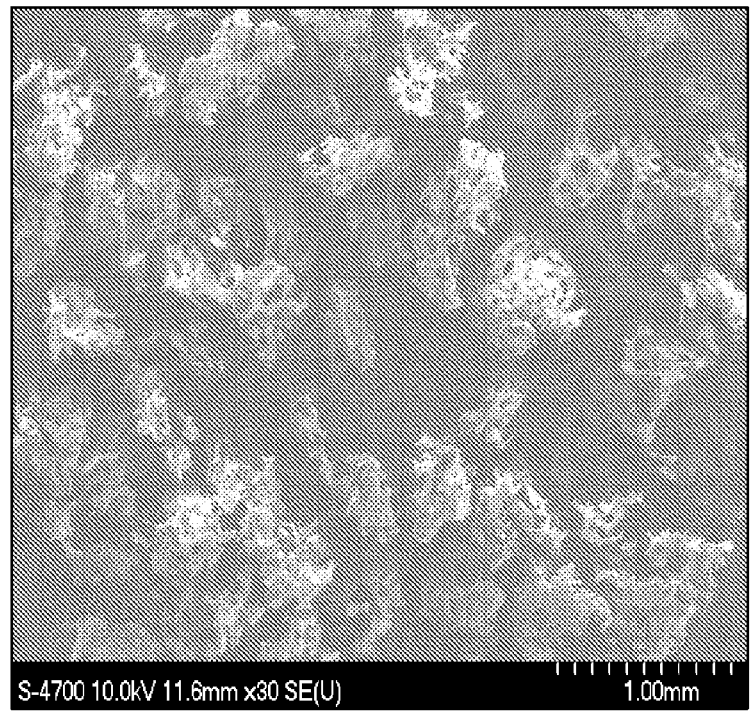
FIG. 5 morphological data (SEM) for ORP5 and control sample from Contour™.
Figure 5B:
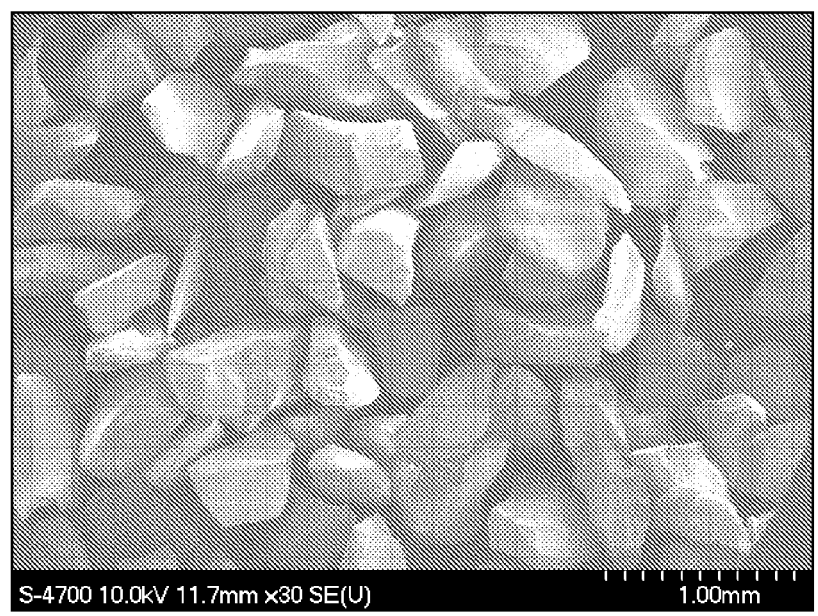

FIG. 5 presents morphological data (SEM) derived from one experimental composition (ORP5); whose morphology is representative of the full set of multi-component systems examined and compared to the commercially available predicate device, Contour. FIG. 5A is a control sample of Contour™ with particle size range of 355-510 μm. FIG. 5B is an experimental sample of ORP5 having particle size range of 355-510 μm.

Figure 6:
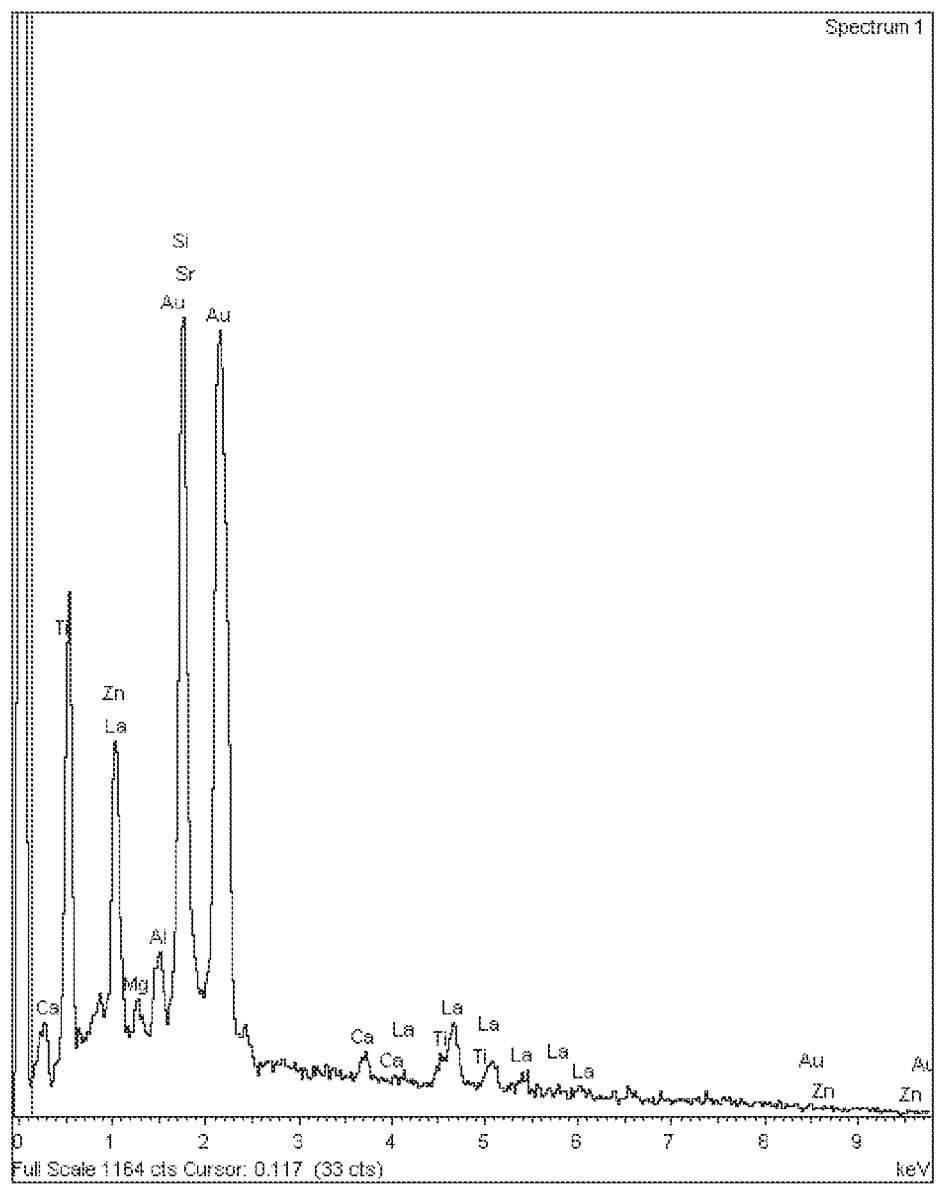
FIG. 6 illustrates chemical (EDX) data for ORP5.

Chemical (EDX) data for ORP5 is presented in FIG. 6 demonstrates that the synthesized composition is as reported in Table 1.

Magic Angle Spinning-Nuclear Magnetic Resonance (MAS-NMR) Spectroscopy for Determination of Non-Bridging Oxygens Generally, the $^{29}$Si MAS-NMR spectra of the glasses are recorded at a spinning frequency of 5 kHz using a high power pulse (P1) acquisition of 1.5 μs for silicon. The $^{29}$Si MAS-NMR samples are spun with a recycle/delay time set to ~2 s. $^{29}$Si NMR chemical shifts are reported in ppm and recorded at an ambient probe temperature with $^{29}$Si referenced externally relative to 2,2-dimethyl-2 silapentane-5-sulfonate sodium salt (DSS) or other appropriate reference. For solid state NMR, shifts recorded using MAS are independent of the isotropic bulk magnetic susceptibility of the sample. The estimated error of chemical shift for data is ca. 0.1 ppm for an ideal material; small variations above this value may be observed.

Example 8

$^{29}$Si magic angle spinning (MAS) NMR studies were carried out on a Bruker Avance NMR spectrometer with a 9.4 T magnet (79.51 MHz $^{29}$Si Larmor frequency) using a probe head for 7 mm rotor diameters. The specimens (<45 μm) were spun at 5.00 kHz. 200 scans were accumulated with single pulse excitation using a pulse length of eighty degrees at 28 kHz rf field strength. The recycle delays were chosen to be three times the spin lattice relaxation times as determined by inversion recovery sequences. Spin lattice relaxation times range between 15 and 26 seconds. The chemical shift scale was referenced externally against Kaolin as secondary chemical shift standard at −91.34 ppm. Error bars on the peak maxima and peak widths are ±1 ppm.

Figure 7:
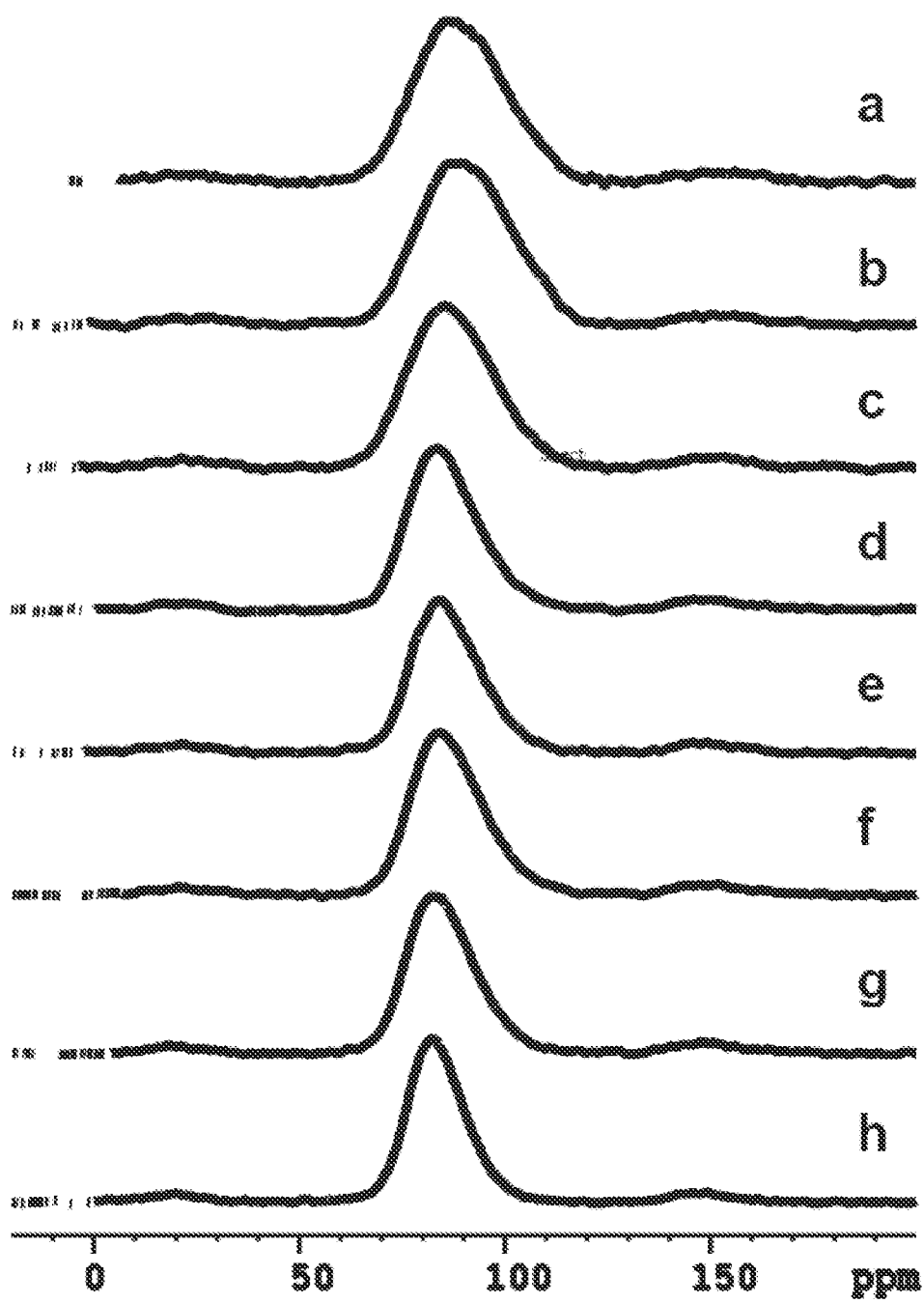
FIG. 7 illustrates $^{29}$Si MAS-NMR spectra for experimental embolic materials.
Figure 8:
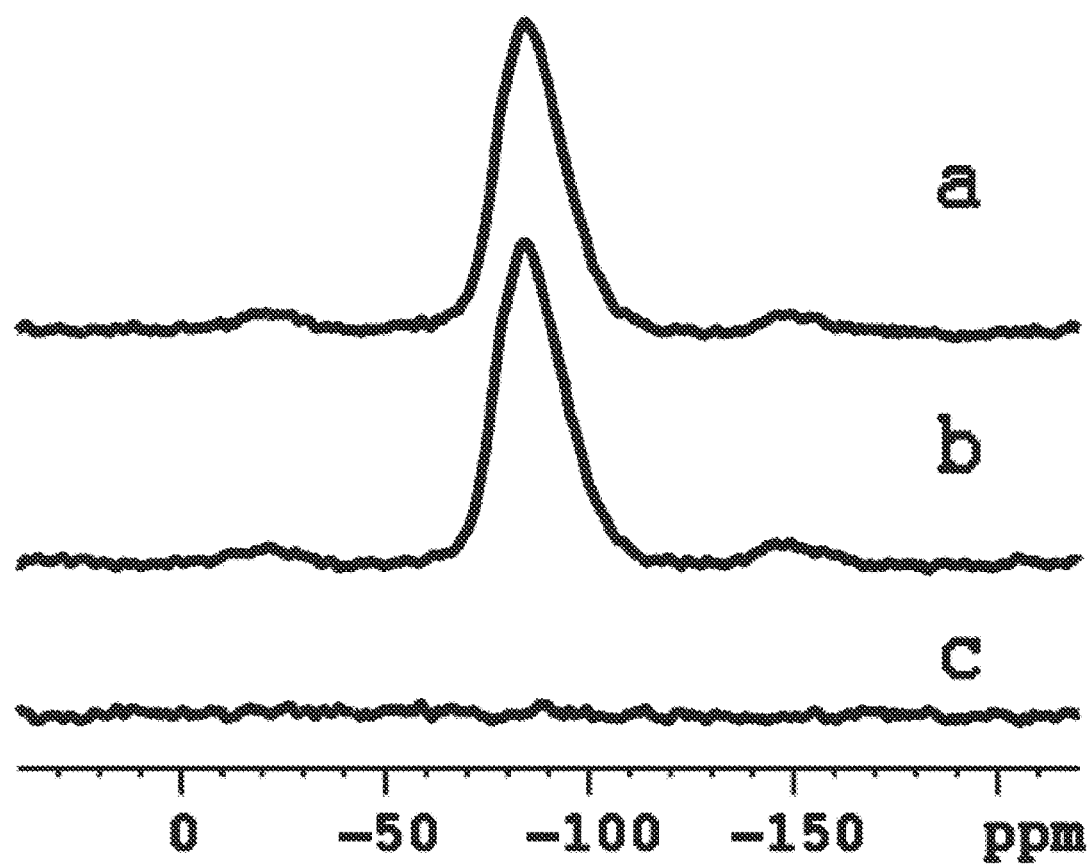
FIG. 8 illustrates $^{29}$Si MAS-NMR spectra for experimental embolic material ORP6.
Figure 9A:
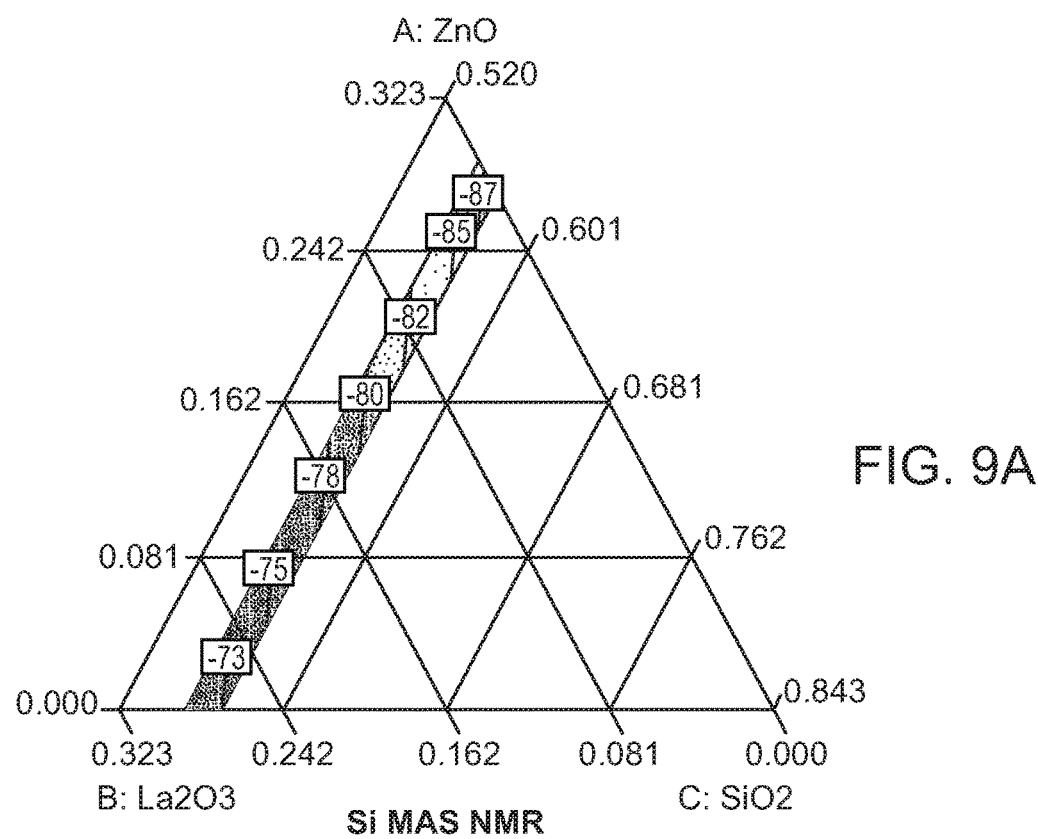
FIG. 9 illustrate contour plots based on the $^{29}$Si MAS-NMR spectra of FIG. 7.
Figure 9B:
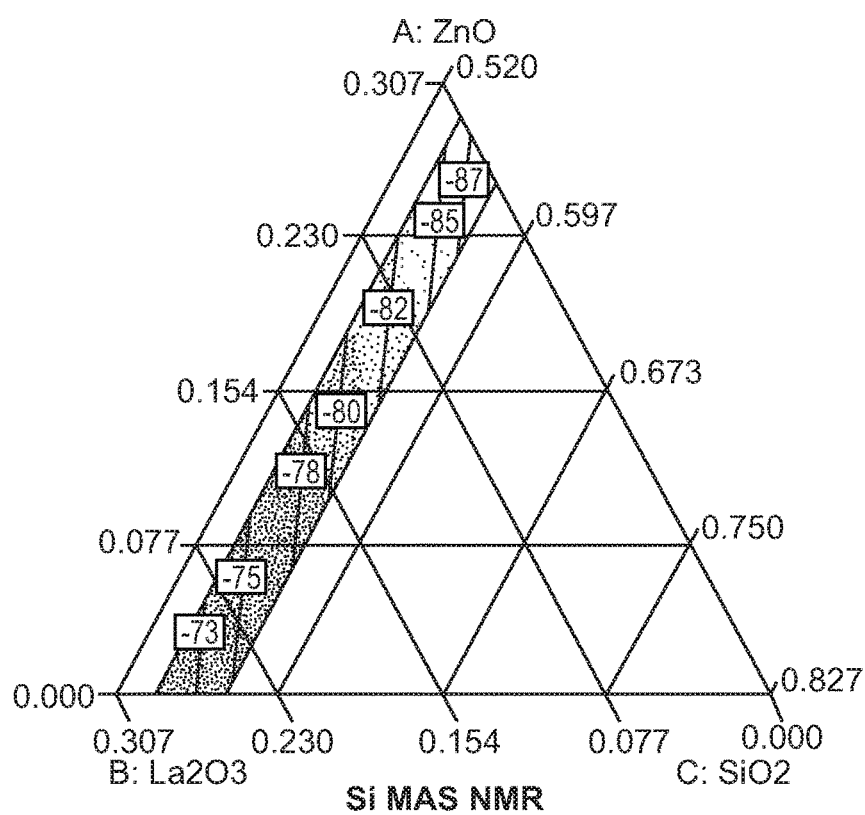
Figure 9C:
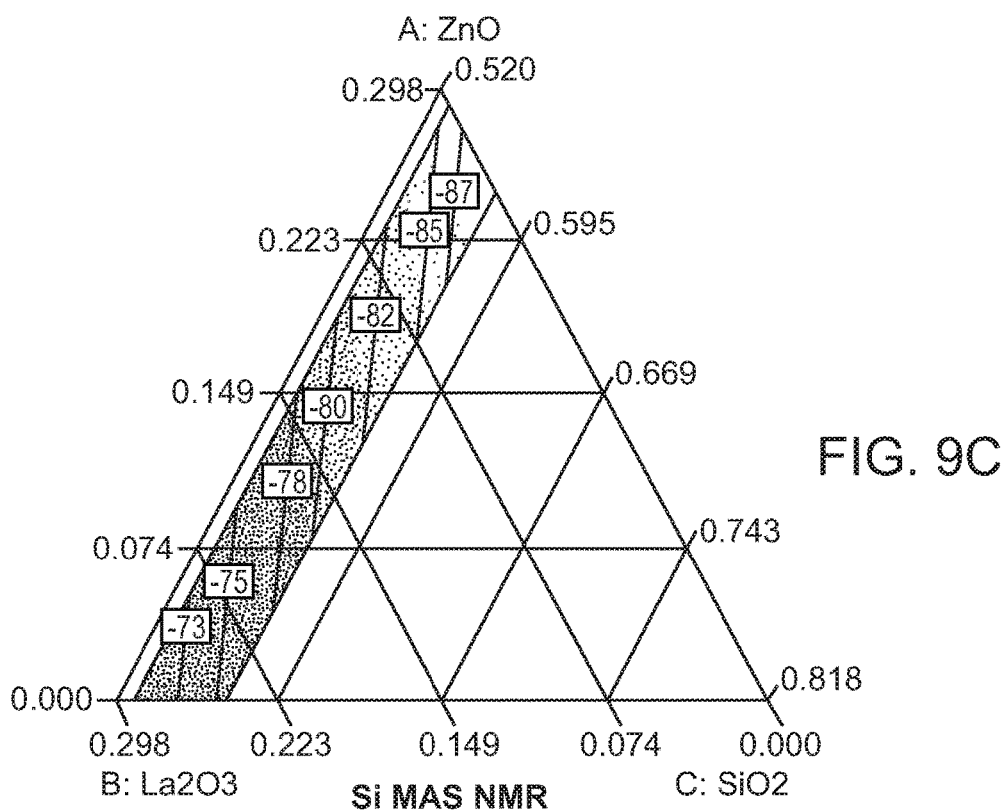
Figure 9D:
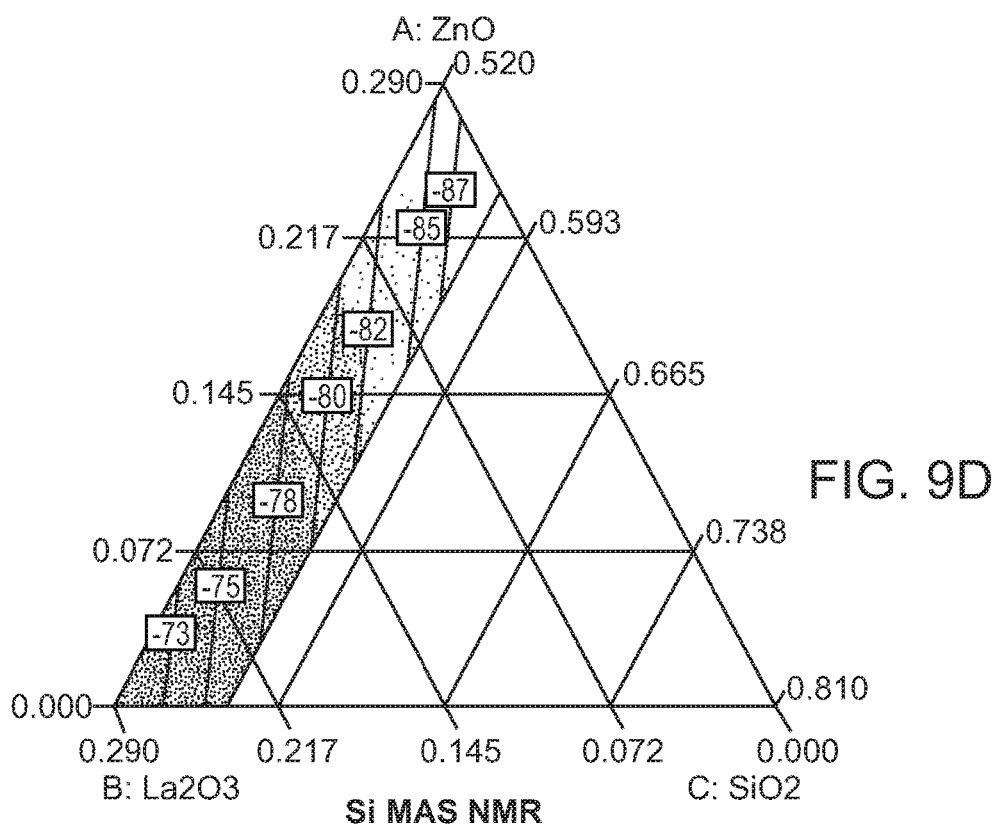
Figure 10A:
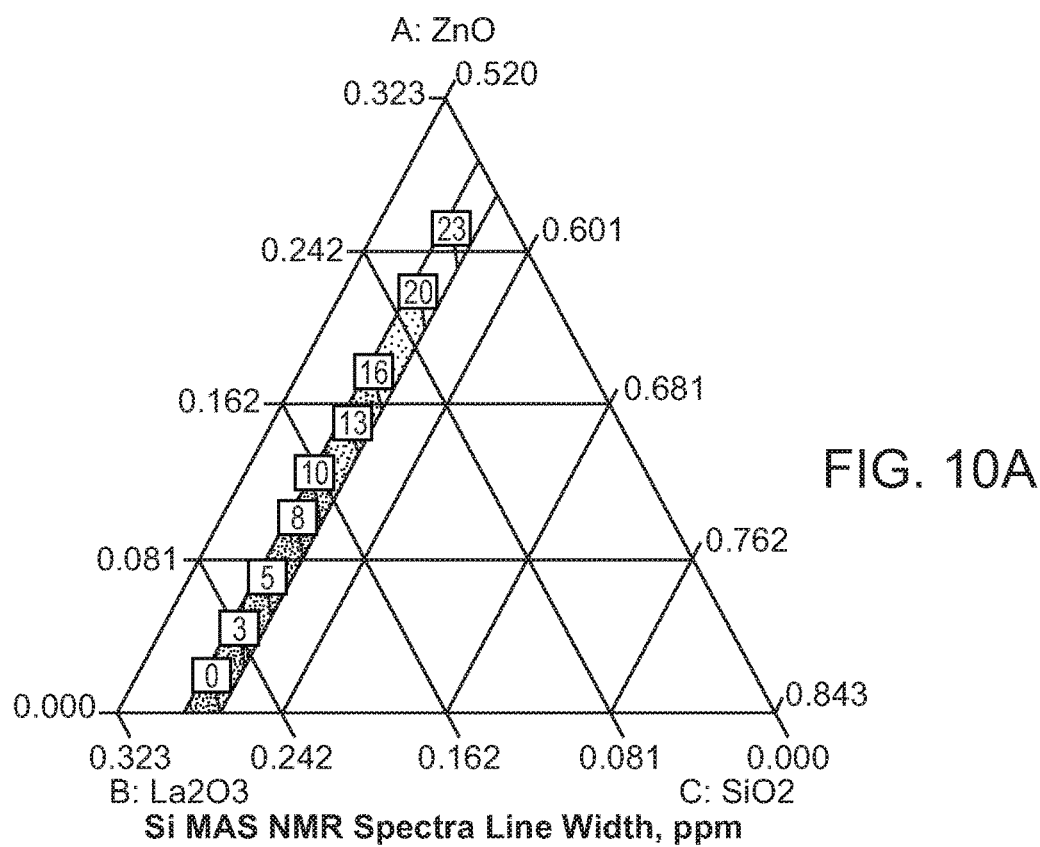
FIG. 10 illustrate additional contour plots based on the $^{29}$Si MAS-NMR spectra of FIG. 7.
Figure 10B:
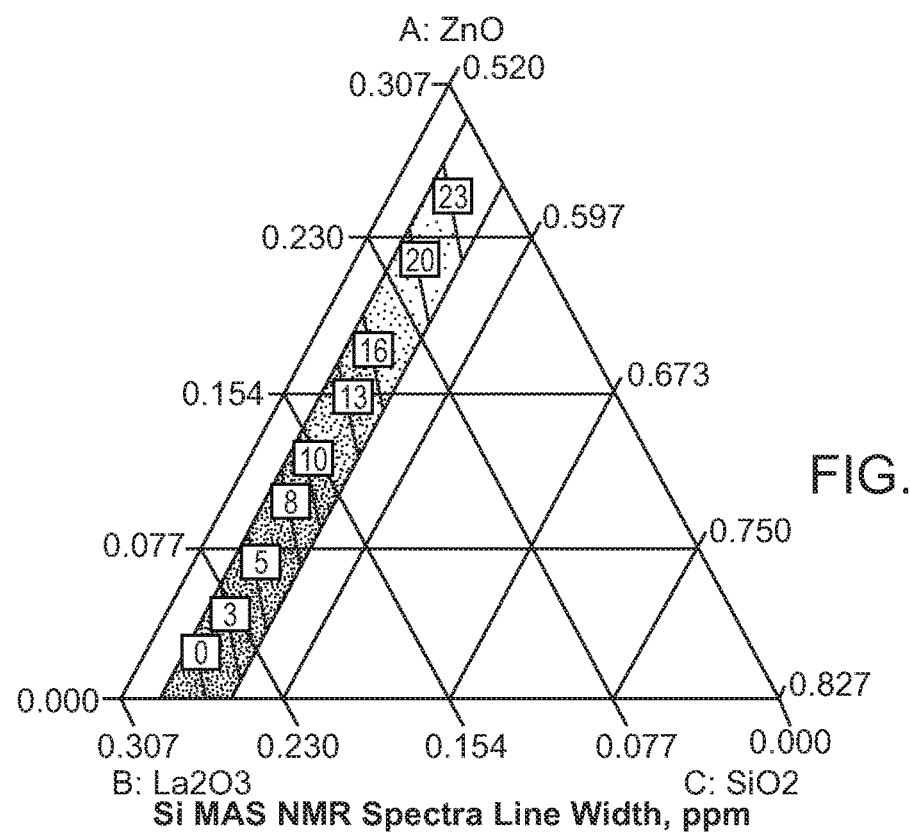
Figure 10C:
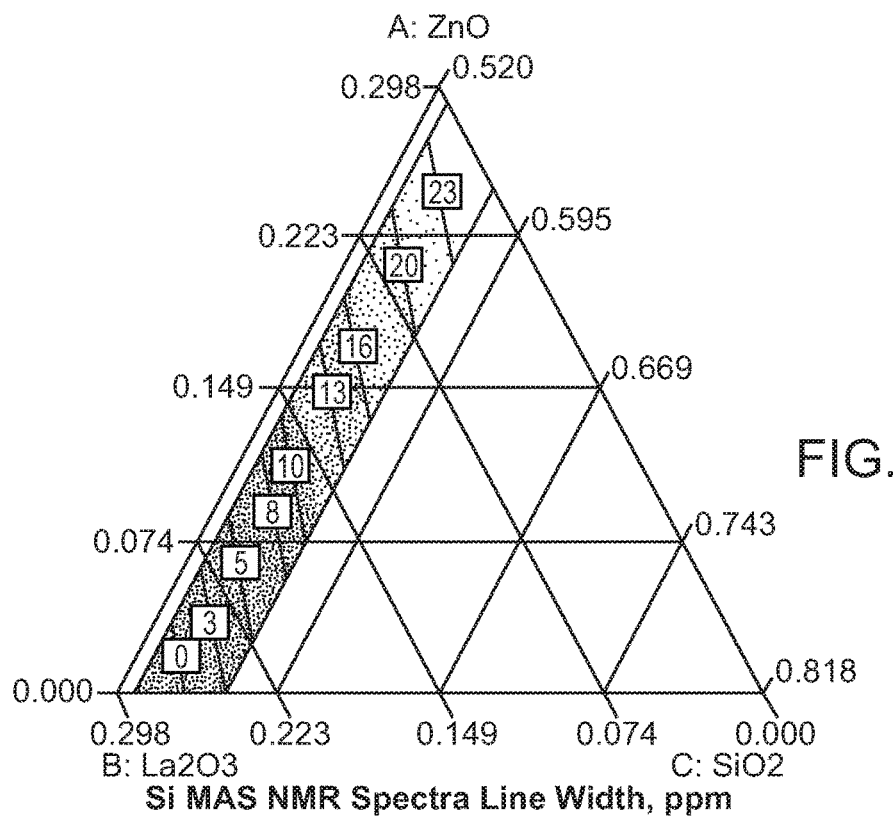
Figure 10D:
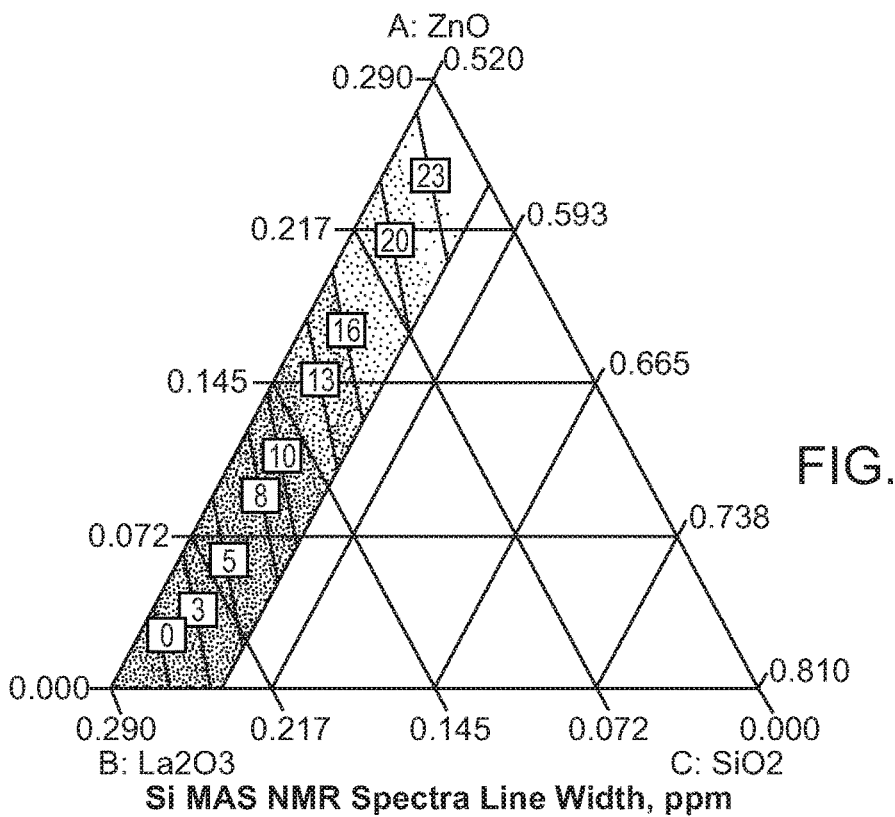

FIG. 7 illustrates $^{29}$Si MAS-NMR spectra for each experimental embolic material (peak maxima and peak width for each is recorded in Table 10, respectively) sorted by decreasing line width (a: ORP11, b: ORP2, c: ORP9, d: ORP7, e: ORP6, f: ORP5, g: ORP3, h: ORP1). To ensure that no crystal signals were missed due to too fast pulsing (50 s) an additional $^{29}$Si MAS NMR spectrum for ORP6 was acquired at longer repetition times (90 s). FIG. 8 illustrates those results—$^{29}$Si MAS-NMR spectra for experimental embolic material ORP6 at (a) 90 s and (b) 50 s repetitions times and (c) their scaled difference; verifying that silica is not part of the crystals detected by XRD. In both spectra, no crystalline components were evident. The XRD diffractograms for ORP1 and ORP6 indicate the presence of some crystalline species which were identified in Table 6.

FIG. 9 illustrates contour plots' showing the compositional-interaction effects on the experimental embolic materials $^{29}$Si MAS-NMR chemical shift (in ppm) at four various additions of Ti ((FIG. 9A) 0.017, (FIG. 9B) 0.033, (FIG. 9C) 0.042 and (FIG. 9D) 0.05 mol.) in actual component coding.

FIG. 10 illustrates contour plots' showing the compositional-interaction effects on the experimental embolic materials $^{29}$Si MAS-NMR spectra line width (ppm) at four various additions of Ti ((FIG. 10A) 0.017, (FIG. 10B) 0.033, (FIG. 10C) 0.042 and (FIG. 10D) 0.05 mol.) in actual component coding.

Table 10 illustrates the total number of positive charges and associated NMR max. position and line width from the nominal compositions outlined in Table 1 (where $SiO_2$, $TiO_2$, ZnO and $La_2O_3$ are varied with equimolar concentrations of CaO, $Na_2O$ MgO and SrO).

TABLE 10

| ORP Sample | SiO$_2$ | TiO$_2$ | ZnO | La$_2$O$_3$ | #charges/ Si | Maximum position ±1 ppm | width ±1 ppm | Morphology |
|---|---|---|---|---|---|---|---|---|
| | | mol fraction | | | | | | |
| 11 | 0.570 | 0.000 | 0.290 | 0.000 | 1.51 | −86.2 | 26.9 | glassy |
| 2 | 0.570 | 0.050 | 0.240 | 0.000 | 1.68 | −89.8 | 26.9 | |
| 9 | 0.520 | 0.050 | 0.290 | 0.000 | 2.04 | −85.5 | 24.7 | |
| 7 | 0.562 | 0.017 | 0.213 | 0.068 | 2.10 | −83.6 | 19.7 | |
| 5 | 0.562 | 0.042 | 0.188 | 0.068 | 2.19 | −84.3 | 19.9 | |
| 3 | 0.537 | 0.042 | 0.213 | 0.068 | 2.39 | −82.2 | 18.8 | |
| 1 | 0.553 | 0.033 | 0.137 | 0.137 | 2.73 | −82.4 | 15.7 | glassy + crystalline |
| 6 | 0.562 | 0.042 | 0.068 | 0.188 | 3.05 | −84.1 | 19.0 | |
| 12 | 0.562 | 0.017 | 0.068 | 0.213 | 3.14 | | | frit synthesis impossible |
| 4 | 0.570 | 0.050 | 0.000 | 0.240 | 3.37 | | | |
| 13 | 0.537 | 0.042 | 0.068 | 0.213 | 3.47 | | | |
| 8 | 0.570 | 0.000 | 0.000 | 0.290 | 3.54 | | | |
| 10 | 0.520 | 0.050 | 0.000 | 0.290 | 4.27 | | | |

Table 11 illustrates regression equations in terms of L_Pseudo (1); Actual components (2) and R$^2$ values; and summarized ANOVA for each response. The ANOVA data demonstrates that the model adequately predicts the characteristics of the particulate material for responses A and B.

TABLE 11

| Response | | Regression Models | Summarized ANOVA | | | | | |
|---|---|---|---|---|---|---|---|---|
| | | | R$^2$ | R$^2_{adj.}$ | R$^2_{pred.}$ | Prob > F | CV (%) | AP |
| A | Chemical Shift (ppm) | 1  −82.25ZnO − 63.59La$_2$O$_3$ − 111.10SiO$_2$ − 103.60TiO$_2$<br>2  −44.32971ZnO + 10.55810La$_2$O$_3$ − 129.18571SiO$_2$ − 107.11371TiO$_2$ | 0.9836 | 0.9589 | 0.7689 | 0.0246 | 0.62 | 16.512 |
| B | Line Width (ppm) | 1  +24.65ZnO − 8.69La$_2$O$_3$ + 39.61SiO$_2$ + 25.19TiO$_2$<br>2  +2.05426ZnO − 95.99452La$_2$O$_3$ + 46.05426SiO$_2$ + 3.65426TiO$_2$ | 0.9997 | 0.9993 | 0.9958 | 0.0004 | 0.45 | 97.003 |

Table 12 presents a summary of the significant (positive and negative) main, interaction and quadratic compositional factors (ranked highest to lowest) and its effect on producing a chemical shift/peak position towards a negative direction and increasing line width; where ↑ denotes an increase and ↓ a decrease. The data is based on actual component coding.

TABLE 12

| Ranking of Compositional Factors | Responses | |
|---|---|---|
| | A | B |
| 1 | ↑SiO$_2$ | ↑ SiO$_2$ |
| 2 | ↑TiO$_2$ | ↑ TiO$_2$ |

TABLE 12-continued

| Ranking of Compositional Factors | Responses | |
|---|---|---|
| | A | B |
| 3 | ↑ZnO | ↑ ZnO |
| 4 | ↑La$_2$O$_3^2$ | ↓ La$_2$O$_3$ |
| 5 | | |

Table 13 presents residuals of the $^{29}$Si MAS-NMR chemical shift (a) and line width (b) study for all material compositions synthesized.

TABLE 13

| | A. $^{29}$Si MAS-NMR chemical shift (ppm) | | | B. $^{29}$Si MAS-NMR line width (ppm) | | |
|---|---|---|---|---|---|---|
| Glass | Experimental Data | Calculated Data | Residual (Difference) | Experimental Data | Calculated Data | Residual (Difference) |
| ORP2 | −89.803 | −89.631 | −0.172 | 26.900 | 26.927 | −0.027 |
| ORP3 | −82.336 | −82.528 | 0.192 | 18.800 | 18.747 | 0.053 |
| ORP5 | −84.305 | −84.650 | 0.345 | 19.900 | 19.847 | 0.053 |
| ORP7 | −83.617 | −83.080 | −0.537 | 19.700 | 19.807 | −0.107 |

TABLE 13-continued

| | A. $^{29}$Si MAS-NMR chemical shift (ppm) | | | B. $^{29}$Si MAS-NMR line width (ppm) | | |
|---|---|---|---|---|---|---|
| Glass | Experimental Data | Calculated Data | Residual (Difference) | Experimental Data | Calculated Data | Residual (Difference) |
| ORP9 | −85.484 | −85.388 | −0.096 | 24.700 | 24.727 | −0.027 |
| ORP11 | −86.223 | −86.491 | 0.268 | 26.900 | 26.847 | 0.053 |

As shown in the NMR spectra, both NMR peak shift may be increased by decreasing any of the four compositional variants in the order $SiO_2$>$TiO_2$>ZnO>$La_2O_3$, and that the line width follows the same order, except for $La_2O_3$ The NMR spectra (FIG. 7)) obtained for ORP2, 9 and 11 appear significantly broader than the other spectra obtained for all other compositions. The difference between the corresponding specimens is that ORP2, 9 and 11 do not contain Lanthanum, while the others do.

Specimen ORP2 is comprised of more $TiO_2$ at the cost of ZnO compared to ORP11 and therefore has a higher charge-to-silica ratio, but, the $Q''$ (nSi, 4-nTi) species resonate at lower ppm values than the $Q''$ (nSi, 4-nZn) species. Based on the charge-to-silica ratio and assuming a roughly binary Q-species distribution, ORP11 and 2 should and experimentally do resonate in the $Q^3/Q^2$ range, specimens ORP9, 7, 5, 3, and 1 in the $Q^2/Q^1$ range (deconvolutions indicate the presence $Q^1$ sites) and specimen ORP6 and below in the $Q^1/Q^0$ range, while specimen ORP10 should only consist of $Q^0$ and separate metal oxide species. Interestingly, for specimen ORP1 and 6, (i.e. where the charge-to-silica ratio comes in the range of $Q^0$ contributions), separation into glassy and crystalline components already occurs with a higher charge ratio and cannot be made into frits at all. This phase separation in specimen ORP6 is the reason, why its NMR properties fall in between those of the spectra for ORP7 and ORP5, due to the crystals withdrawing cation-oxides and to result in a glass of different composition studied by NMR. $La_2O_3$, even at modest concentrations causes a breakdown of the glasses. This is useful because it adds to the tunability of the degradation of the particulate material.

Quantification of Degradation Products from Glass and Composite

TRIS-HCl buffer and citric acid buffer solutions with a pH of 7.4±0.1 and pH of 3.0±0.2 respectively, are prepared to simulate normal and extreme physiological conditions (according to ISO10993-14). Both buffer solutions are used for the quantification of degradation products from the glasses. 100 mg of each particulate material are immersed in 10 ml of each solution (n=3) in polypropylene tubes maintained at 37° C. in a shaking waterbath, agitated at 2 Hz. Specimens are stored for various durations of time—for example, 1, 3, 7, or 30 days. After each time period, specimens are removed and filtered through Grade 5 Whatman filter paper, the filtrate retained for ionic content analysis. The degradation products from the glass are identified and quantified using Inductively Coupled Plasma-Mass Spectrometer. Analysis of each extract are performed in triplicate (n=3 (extracts per condition), 3 analyses performed on each extract).

Analysis of Ion Release Profiles

The ion release profiles from the embolic agents are described in terms of the ion release concentration (Y) over incubation time (X). Since the incubation time is not an input of the correlation function, the time dependent functions have been fitted to nonlinear regressive polynomial, gaussian, sine waves and exponential models using Prism 5.0 software (GraphPad software Inc.). The best fitting model for the four elements with respect to each embolic agent is the one phase-decay association model:

$$Y=Y_0+(Plateau-Y_0)*(1-\exp(-K*X)) \qquad Eq. 7$$

Wherein:
'Y' and 'X' are the ion release concentrations in ppm and incubation time in hours, respectively;
'$Y_0$' is the ion release concentration (ppm) at initial ion release; where Y value at $X_0$=1;
'Plateau' is the ion release concentration at an infinite time (ppm), where Y value at X=120 h;
'K' is the rate constant, expressed in reciprocal of the '$t_{au}$' incubation time and unit is inverse days;
'$t_{au}$' denotes the time necessary for ion release to reach 63% of the estimated '$y_{max}$' (ppm);
'$t^{1/2}$' denotes the half-life (time) to reach 50% of final '$y_{max}$' value, '$t^{1/2}=t_{au}*LN (2)$';
'$t_s$' denotes the difference between $Y_0$ and Plateau;
'$R^2$' is the sum of the squares of the distances of the points from the best-fit of the exponential nonlinear regression as determined by Prism 5.0 (GraphPad Inc.) software. The value of $R^2$ is a fraction between 0.0 and 1.0, with the best-fit line with a $R^2$ equal to 1.0.

Cell Culture Testing with Mouse Fibroblast Cell Line L929

The established mouse fibroblast cell line L929 (American Type Culture Collection CCL 1 fibroblast, NCTC clone 929) is cultured in M199 media supplemented with 10% foetal bovine serum and 1% (2 mM) L-glutamine. Cells are grown in T-75 flasks at 37° C. in a 5% $CO_2$ incubator. When the cells reach confluency, they are chemically removed using 0.25% trypsin, centrifuged and re-suspended in fresh culture media to create a new single cell suspension for further inoculation.

Cell Viability Assay

3T3 cells are seeded at a density of $1\times10^4$/ml in 24 well plates (Sarstedt, Ireland). M199 Culture media is used as a negative control and culture media plus cells used as a positive control. Plates are then incubated for 24 hrs in a cell culture incubator at 37° C. (5% $CO_2$/95% air atmosphere). After 24 hrs, 100 µl of sterile tissue culture water are added to control wells. 100 µl of relevant experimental extracts (containing particles) are added to appropriate wells for testing. The plate is then incubated for 24 hrs in a cell culture incubator at 37° C. (5% $CO_2$/95% air atmosphere). After 24 hrs incubation, each well is exposed to MTT (Sigma Aldrich, Ireland) at an amount equal to 10% of the culture media volume (100 µl). Plates are returned to the incubator for 3 hrs. After incubation, MTT solubilisation solution are added to each well at a volume equal to the original culture media volume (1 ml). Each well is titrated using a pipette in order to enhance dissolution of the crystals, after which the absorbance of each well is measured spectrophotometrically at a wavelength of 570 nm. Cell positive control wells were assumed to have metabolic activities of 100% and the percentage metabolic activity of the cells exposed to experimental extracts were calculated relative to this.

Example 9

Preparation of Particle Extracts for Degradation Studies 0.1 g of particles and Contour™ (commercial control) (Lot No.s: 13473927 and 13599201) were immersed in 10 ml[6] of sterile tissue culture water (Sigma-Aldrich, Canada) for 12, 24, 48, 96 and 120 hours at 37° C. in a shaking waterbath (Stuart Sb40, Techne Inc., USA) vibrated rotationally at 2 Hz. After each storage period, samples were filtered using a sterile 0.20 μm filter (Sarstedt, Canada), and filtrates stored at 7° C. prior to in vitro evaluation.

The $SO^{4+}$, $Na^+$, $Ca^{2+}$, $Zn^{2+}$, $Ti^{4+}$, $La^{3+}$, $Sr^{2+}$, and $Mg^{2+}$ concentrations for each extract were analyzed using inductively coupled plasma atomic emission spectroscopy (ICP-AES, Perkin Elmer Optima 3000, MA, USA). The absorption wavelengths used for the determination of each element is reported in Table 14. Before each cycle of measurement, calibration curves were obtained by preparing standard solutions containing $Ti^{4+}$, $La^{3+}$, $Sr^{2+}$, and $Mg^{2+}$ and a separate set of standard solutions containing $Si^{4+}$, $Na^+$, $Ca^{2+}$ and $Zn^{2+}$ (as obtained from JVA Analytical Ltd, Ireland) at concentrations reported in Tables 15 and 16. Standard sample concentrations were measured periodically to ensure the accuracy of the calibration curve. Triplicates of each extract (from each incubated embolic agent) were measured for each element, with appropriate adjustments in outputs being deployed to balance dilutions of original extracts. The results demonstrate that the complex multi-component system provides for tailored rates of degradability.

TABLE 14

| Element | Absorption Wavelength | Lower Limit | Upper Limit | Background Correction |
|---|---|---|---|---|
| $Si^{4+}$ | 288.158 | 288.073 | 288.256 | ±0.026 |
| $Na^+$ | 330.237 | 330.136 | 330.348 | ±0.030 |
| $Ca^{2+}$ | 396.847 | 396.679 | 397.039 | ±0.072 |
| $Zn^{2+}$ | 334.501 | 334.400 | 334.614 | ±0.031 |
| $Ti^{4+}$ | 337.279 | 335.188 | 334.810 | ±0.031 |
| $La^{3+}$ | 407.735 | 407.971 | 407.596 | ±0.075 |
| $Mg^{2+}$ | 279.553 | 279.646 | 279.399 | ±0.026 |
| $Sr^{2+}$ | 421.552 | 421.759 | 421.371 | ±0.078 |

Table 15 provides the standard concentrations used for the ICP measurements (JVA Analytical, Ireland).

TABLE 15

| Standard | $Si^{4+}$ (mg/L) | $Na^+$ (mg/L) | $Ca^{2+}$ (mg/L) | $Zn^{2+}$ (mg/L) |
|---|---|---|---|---|
| 1 | 2 | 1 | 0.5 | 1 |
| 2 | 4 | 2 | 1 | 2 |
| 3 | 10 | 4 | 3 | 4 |

Table 16 provides laboratory standard concentrations used for the ICP measurements.

TABLE 16

| Standard | $Ti^{4+}$ (mg/L) | $La^{3+}$ (mg/L) | $Mg^{2+}$ (mg/L) | $Sr^{2+}$ (mg/L) |
|---|---|---|---|---|
| 4 | 0.1 | 0.1 | 0.1 | 0.1 |
| 5 | 1 | 1 | 1 | 1 |
| 6 | 10 | 10 | 10 | 10 |

Figures 11A, 11B:
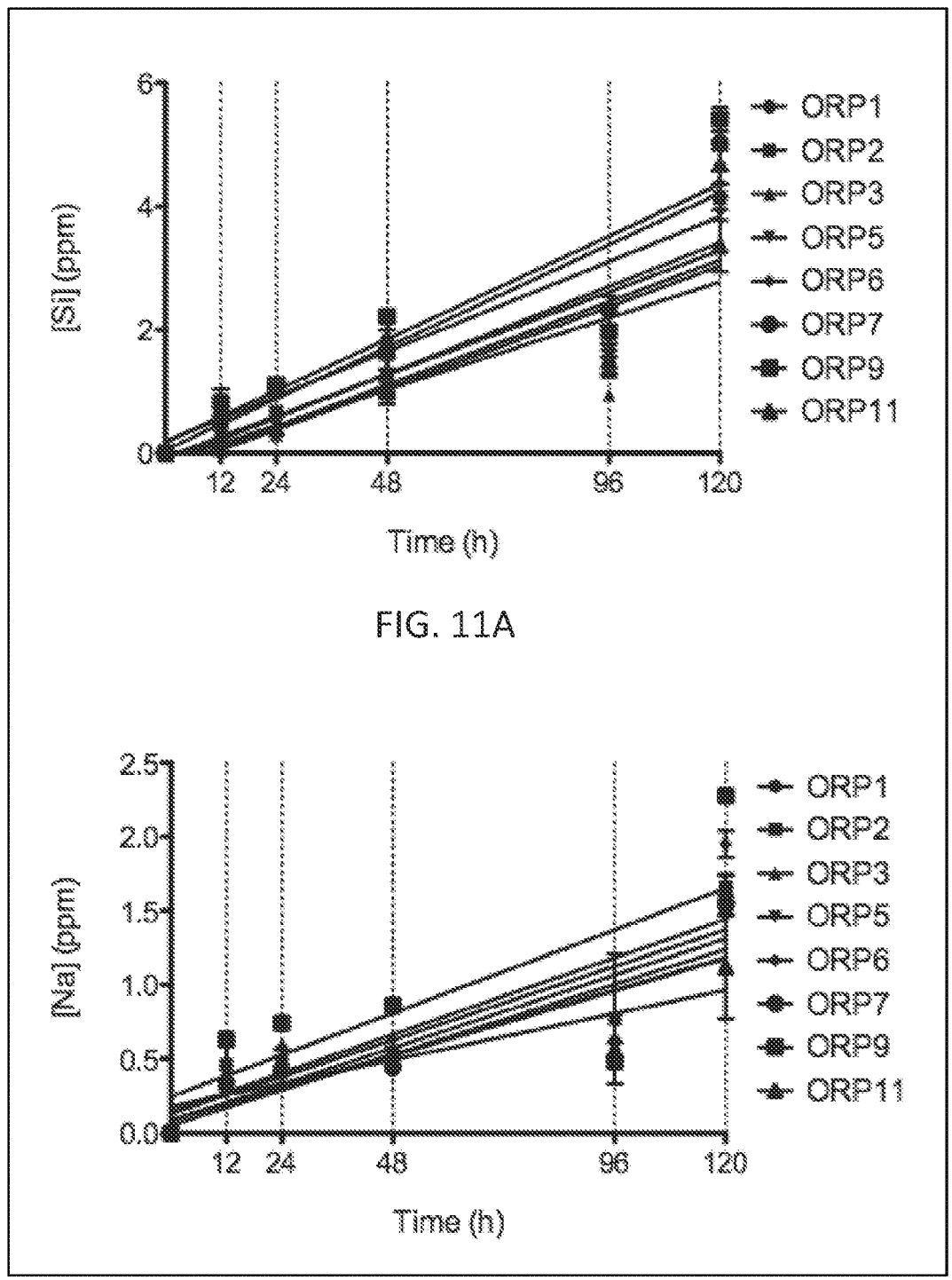
FIG. 11 presents ion release profiles for Si (FIG. 11A) and Na (FIG. 11B) release of the eight embolic particulates.
Figures 12A, 12B:
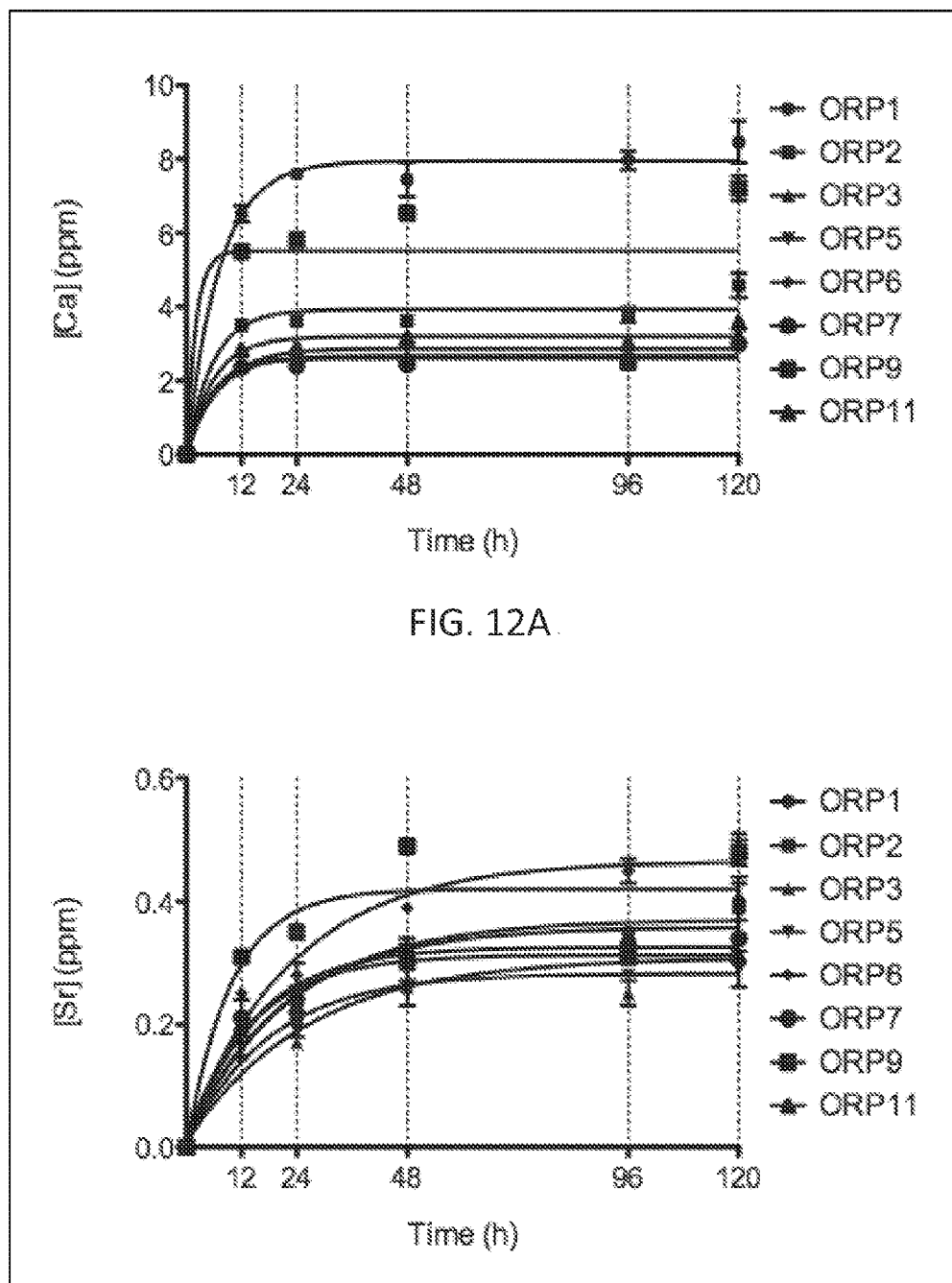
FIG. 12 presents ion release profiles for Ca (FIG. 12A) and Sr (FIG. 12B) release of the eight embolic particulates.
Figures 13A, 13B:
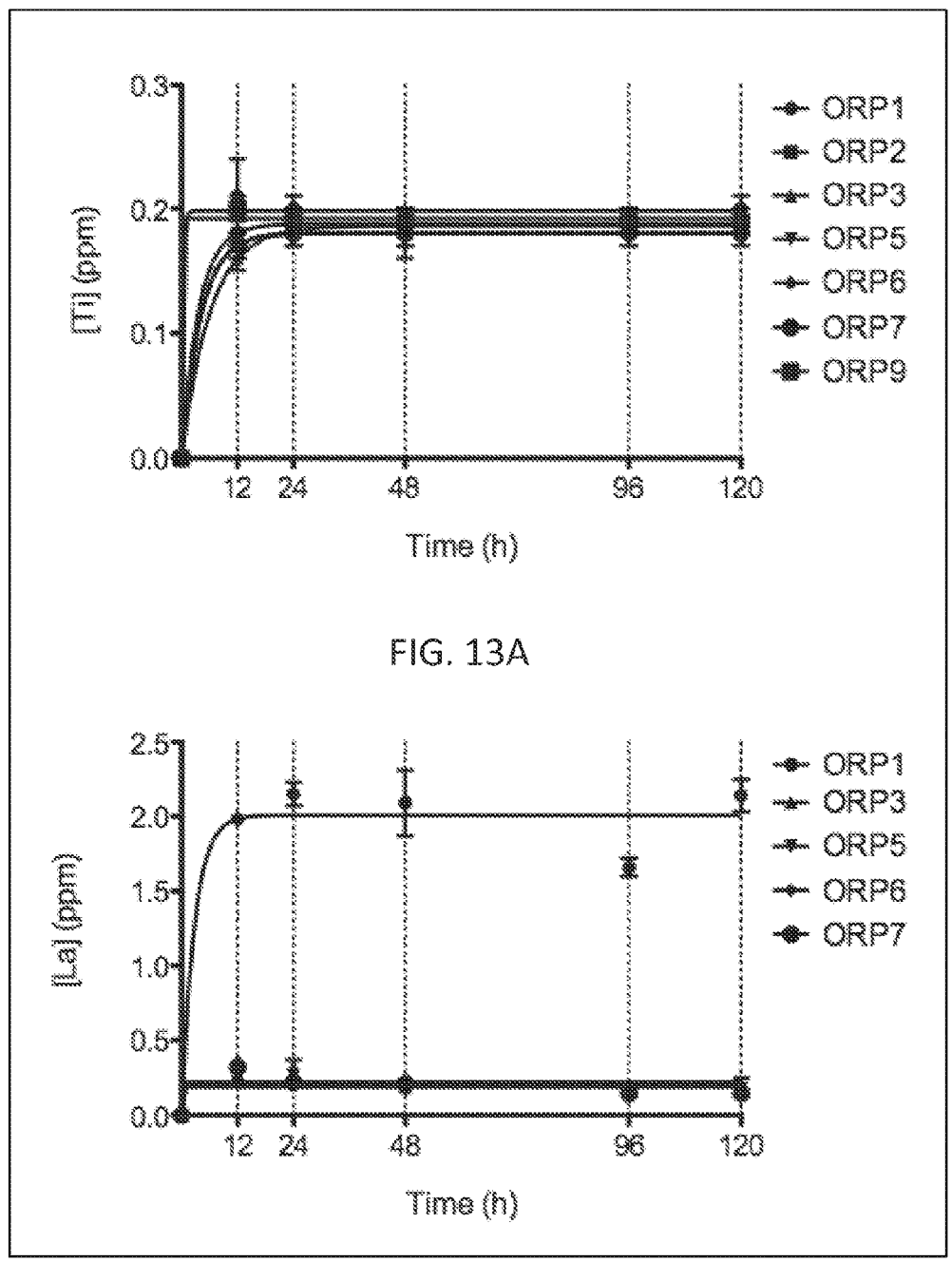
FIG. 13 presents ion release profiles for Ti (FIG. 13A) and La (FIG. 13B) release of the eight embolic particulates.
Figures 14A, 14B:
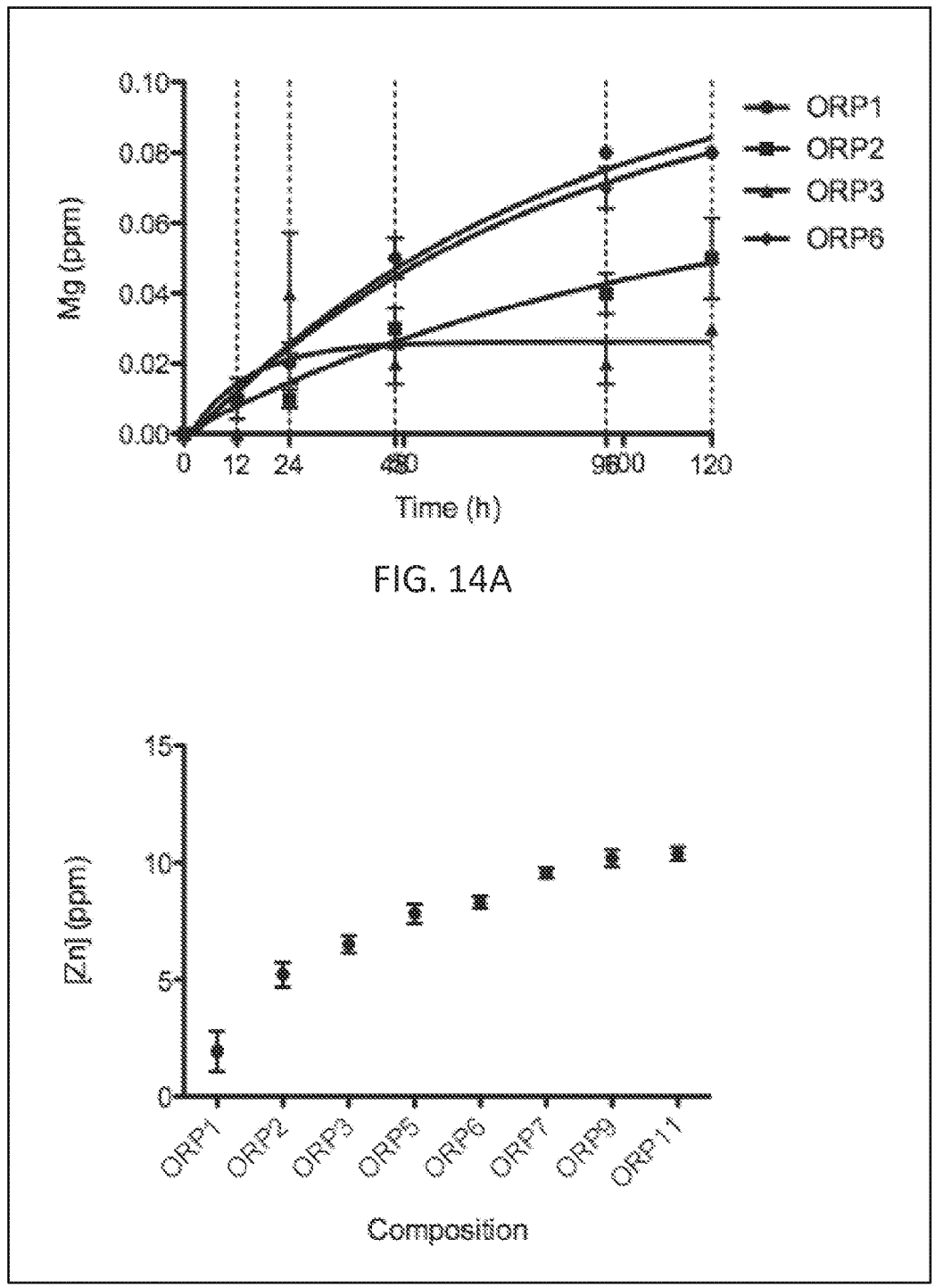
FIG. 14 presents an ion release profile for Mg (FIG. 14A) and mean (±SD) release levels for Zn (FIG. 14B) of the eight embolic particulates.
Figures 15A, 15B:
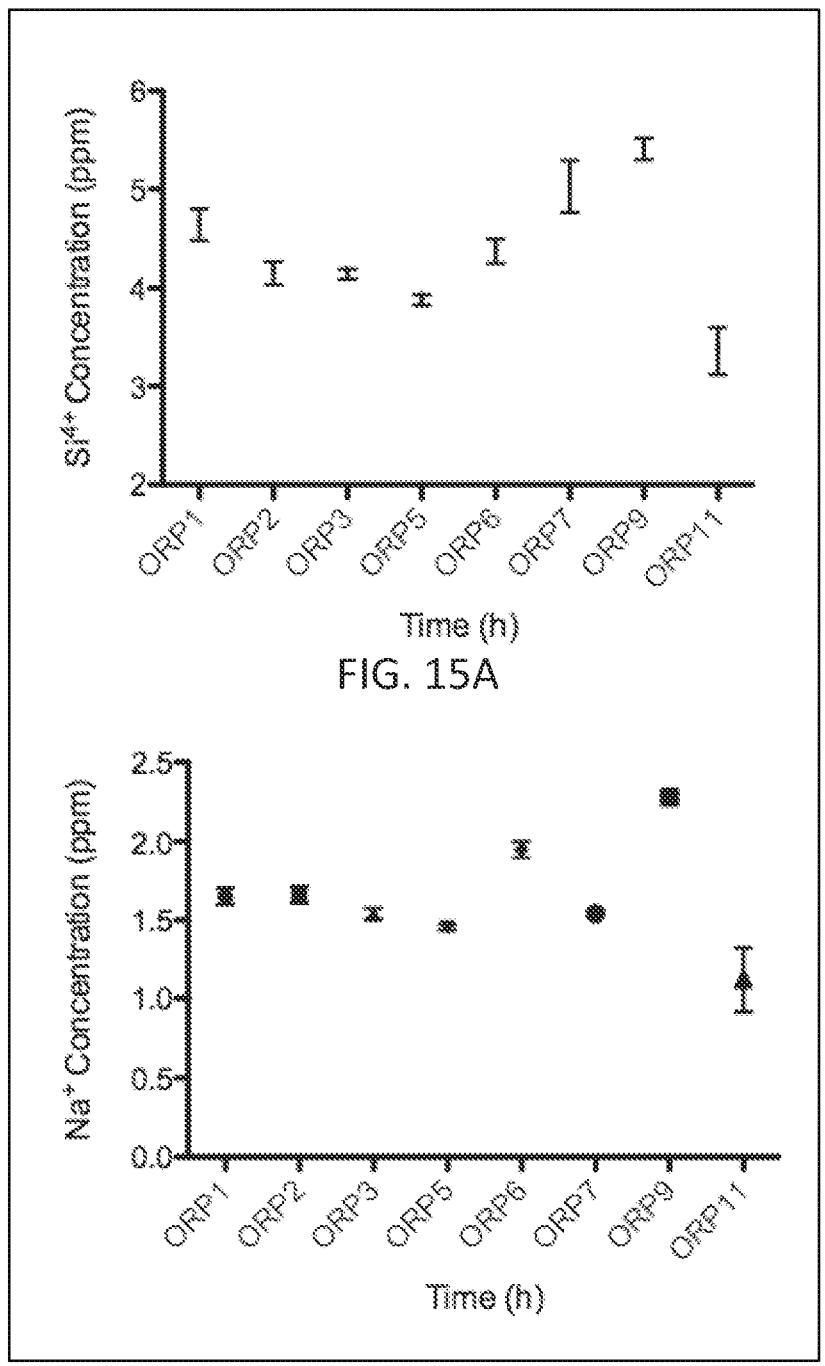
FIG. 15 presents the effect of embolic material composition on release levels for Si (FIG. 15A) and Na (FIG. 15B) after 120 h incubation periods.
Figures 16A, 16B:
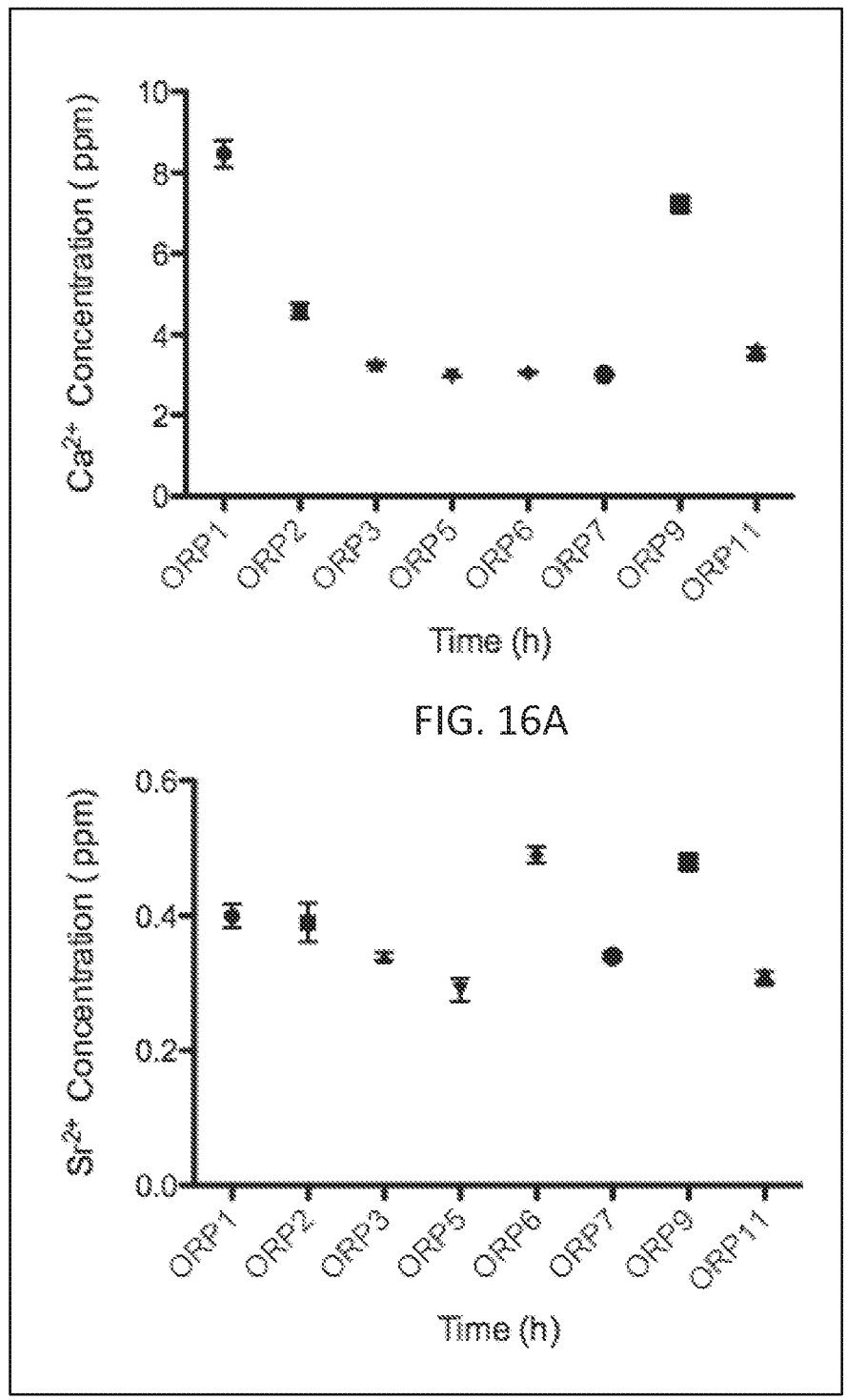
FIG. 16 presents the effect of embolic material composition on release levels for Ca (FIG. 16A) and Sr (FIG. 16B) after 120 h incubation periods.
Figure 17A:
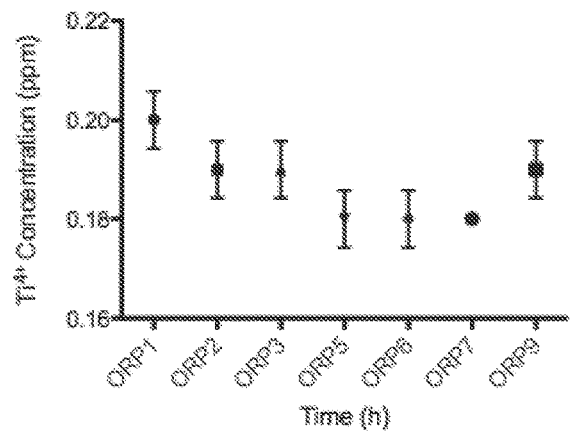
FIG. 17 presents the effect of embolic material composition on release levels for Ti (FIG. 17A); La (FIG. 17B) and Mg (FIG. 17C) after 120 h incubation periods.
Figure 17B:
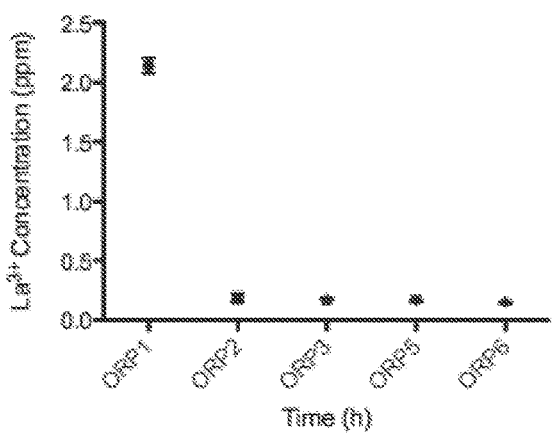
Figure 17C:
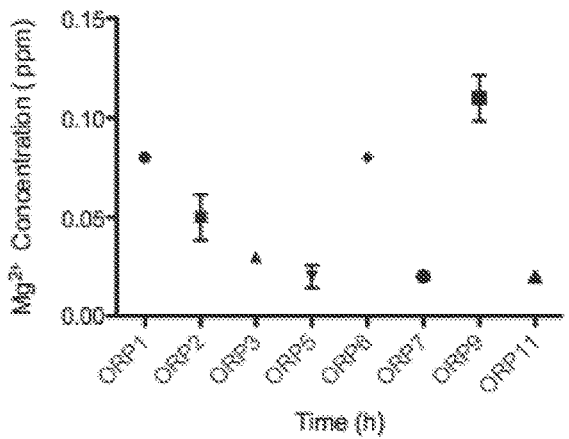

FIG. 11 presents ion release profiles for Si (FIG. 11A) and Na (FIG. 11B) release of the eight embolic particulates with time dependency over 12, 24, 48, 96 and 120 h. Lines are drawn as visual guides. FIG. 12 presents ion release profiles for Ca (FIG. 12A) and Sr (FIG. 12B) release of the eight embolic particulates with time dependency over 12, 24, 48, 96 and 120 h. Lines are drawn as visual guides. FIG. 13 presents ion release profiles for Ti (FIG. 13A) and La (FIG. 13B) release of the eight embolic particulates with time dependency over 12, 24, 48, 96 and 120 h. Lines are drawn as visual guides. Lines are drawn as visual guides (excluding ambiguous data with $R^2<0.6$). FIG. 14 presents an ion release profile for Mg (FIG. 14A) and mean (±SD) release levels for Zn (FIG. 14B) of the eight embolic particulates with time dependency over 12, 24, 48, 96 and 120 h (for Zn (FIG. 14B) only). Lines are drawn as visual guides. Lines are drawn as visual guides (excluding ambiguous data with $R^2<0.6$). FIG. 15 presents the effect of embolic material composition on release levels for Si (FIG. 15A) and Na (FIG. 15B) after 120 h incubation periods. FIG. 16 presents the effect of embolic material composition on release levels for Ca (FIG. 16A) and Sr (FIG. 16B) after 120 h incubation periods. FIG. 17 presents the effect of embolic material composition on release levels for Ti (FIG. 17A); La (FIG. 17B) and Mg (FIG. 17C) after 120 h incubation periods.

Table 16 provides the goodness of fit (in terms of $R^2$ values) for the non-linear one phase association model formed from $Si^{4+}$ and $Na^+$ release over 5 time points (12, 24, 48, 96, 120 h).

TABLE 16

| Embolic Composition | $Si^{4+}$ $R^2$ | $Na^+$ $R^2$ |
|---|---|---|
| ORP1 | 0.8219 | 0.7752 |
| ORP2 | 0.8115 | 0.7383 |
| ORP3 | 0.7195 | 0.7174 |
| ORP5 | 0.8691 | 0.8935 |
| ORP6 | 0.8123 | 0.6263 |
| ORP7 | 0.8672 | 0.7111 |
| ORP9 | 0.7839 | 0.5419 |
| ORP11 | 0.8697 | 0.6747 |

Table 17 provides the best-fit parameters for the non-linear one phase association model formed from $Ca^{2+}$ release over 5 time points (12, 24, 48, 96, 120 h).

TABLE 17

| Embolic Composition | $t^{1/2}$ (h) | $t_{au}$ (h) | $t_s$ (h) | $y_{max}$ (ppm) | $R^2$ |
|---|---|---|---|---|---|
| ORP1 | 4.938 | 7.123 | 7.948 | 7.953 | 0.9808 |
| ORP2 | 4.003 | 5.776 | 3.932 | 3.936 | 0.9427 |
| ORP3 | 4.840 | 6.982 | 2.860 | 2.868 | 0.9594 |
| ORP5 | 4.523 | 6.525 | 2.663 | 2.669 | 0.9660 |
| ORP6 | 3.926 | 5.664 | 2.650 | 2.653 | 0.9604 |
| ORP7 | 3.771 | 5.440 | 2.605 | 2.607 | 0.9605 |
| ORP9 | 1.379 | 1.989 | 5.515 | 5.515 | 0.6575 |
| ORP11 | 4.044 | 5.835 | 3.189 | 3.193 | 0.9669 |

Table 18 provides the best-fit parameters for the non-linear one phase association model formed from $Sr^{2+}$ release over 5 time points (12, 24, 48, 96, 120 h).

TABLE 18

| Embolic Composition | $t^{1/2}$ (h) | $t_{au}$ (h) | $t_s$ (h) | $y_{max}$ (ppm) | $R^2$ |
|---|---|---|---|---|---|
| ORP1 | 15.70 | 22.65 | 0.3583 | 0.3706 | 0.9550 |
| ORP2 | 14.64 | 21.12 | 0.3446 | 0.3585 | 0.9181 |
| ORP3 | 18.28 | 26.38 | 0.2980 | 0.3089 | 0.9239 |
| ORP5 | 12.63 | 18.21 | 0.2772 | 0.2828 | 0.9713 |

TABLE 18-continued

| Embolic Composition | $t^{1/2}$ (h) | $t_{au}$ (h) | $t_s$ (h) | $y_{max}$ (ppm) | $R^2$ |
|---|---|---|---|---|---|
| ORP6 | 16.00 | 23.08 | 0.4494 | 0.4669 | 0.9645 |
| ORP7 | 10.20 | 14.72 | 0.3201 | 0.3262 | 0.9666 |
| ORP9 | 6.786 | 9.79 | 0.4188 | 0.4202 | 0.8559 |
| ORP11 | 9.671 | 13.95 | 0.3096 | 0.3129 | 0.9749 |

Table 19 presents the best-fit parameters for the non-linear one phase association model formed from $Ti^{4+}$ release over 5 time points (12, 24, 48, 96, 120 h). The asterisk (*) represents the models denoted as ambiguous.

TABLE 19

| Embolic Composition | $t^{1/2}$ (h) | $t_{au}$ (h) | $t_s$ (h) | $y_{max}$ (ppm) | $R^2$ |
|---|---|---|---|---|---|
| ORP1* | ~0.233 | ~0.336 | 0.1980 | 0.1980 | 0.9661 |
| ORP2 | 2.563 | 3.698 | 0.1875 | 0.1875 | 0.9815 |
| ORP3 | 4.300 | 6.203 | 0.1861 | 0.1862 | 0.9878 |
| ORP5 | 2.885 | 4.162 | 0.1801 | 0.1801 | 0.9876 |
| ORP6 | 2.885 | 4.162 | 0.1801 | 0.1801 | 0.9876 |
| ORP7 | 2.885 | 4.162 | 0.1801 | 0.1801 | 0.9925 |
| ORP9* | ~0.000 | ~0.000 | 0.1920 | 0.1920 | 0.9867 |

Table 20 presents the best-fit parameters for the non-linear one phase association model formed from $Mg^{2+}$ release over 5 time points (12, 24, 48, 96, 120 h). The asterisk (*) represents the models denoted as ambiguous.

TABLE 20

| Embolic Composition | $t^{1/2}$ (h) | $t_{au}$ (h) | $t_s$ (h) | $y_{max}$ (ppm) | $R^2$ |
|---|---|---|---|---|---|
| ORP1 | 57.52 | 82.98 | 0.11 | 0.1111 | 0.9639 |
| ORP2 | 74.21 | 107.10 | 0.07 | 0.0721 | 0.7802 |
| ORP3 | 9.50 | 13.70 | 0.03 | 0.0261 | 0.3176 |
| ORP5* | ~0.05 | ~0.01 | 0.05 | 0.0460 | 0.2356 |
| ORP6 | 58.01 | 83.69 | 0.11 | 0.1058 | 0.9656 |
| ORP7* | ~0.00 | ~0.00 | 0.05 | 0.0460 | 0.1572 |
| ORP9 | 7.71 | 11.12 | 0.08 | 0.0751 | 0.4458 |
| OR11 | 3.91 | 5.64 | 0.04 | 0.0372 | 0.1779 |

Surprisingly, $Zn^{2+}$ was only found to initially release after 120 h. All other ions were found to release continuously for all time periods. This is contrary to the expectation that $Zn^{2+}$ would release ions with the immediate onset of its submersion into solution.

The ion release profiles for both $Si^{4+}$ and $Na^{+}$ present stable time-dependent increases in ion release (denoted by the goodness of fit values represented by $R^2$ values ranging from 0.81 to 0.87 with the exception of ORP3 and 9 yielding $R^2$ values of 0.72 and 0.78, respectively for $Si^{4+}$ and $R^2$ values ranging from 0.71 to 0.90 with the exception of ORP6, 9 and 11 yielding $R^2$ values of 0.63, 0.54 and 0.67, respectively for $Na^{2+}$) up to 120 h, which potentially indicate the controllable nature for each composition. Full stabilization of ion release is not evident for both ions after 120 h.

An initial burst of $Ca^{2+}$ released for ORP9 during the first few hours in solution was noted, ending abruptly to maintain a stable release level for the remainder of the study. ORP1 also exhibited an initial burst of $Ca^{2+}$ release to gradually release $Ca^{2+}$ at a stable rate past 24 h. The remaining compositions however, show more gradual initial $Ca^{2+}$ release up to 24 h prior to reach full stabilization. This is likely due to the formation of a hydrogel like layer on the full surface area of the glass particulate as a result of initial $Ca^{2+}$ release (from the particulate) in exchange for $H_3O^+$ in the incubation media, to precipitate onto the entire surface of the particulate; and further impact upon the rate of ion release from the particulates. Interestingly, the same release profiles were observed for $Sr^{2+}$ and $Ti^{4+}$.

Importantly, very slow release levels of $Mg^{2+}$ into the solution were noted, to suggests that it is strongly chelated by the silicate network. The same is reported for $La^{2+}$ with the exception of ORP1 (possibly due to an increase in crystalline species).

Preparation of Particle Extracts for MTT/Release of LDH Assays

For this protocol, all particles were sterilized by autoclaving (AMSCO Medallist) at 121°/25 bar for a period of 20 mins prior to incubation. Pre-sterilized batches of Contour™ (Lot No.s: 13473927 and 13599201) were used as a control. Subsequently, an equivalent amount (0.1 g) of each sterile glass (ORP1-3, ORP5-7, ORP9, ORP11) and Contour™ were immersed in 10 mL of sterile tissue culture water (Sigma-Aldrich, Canada) for 24 hours, placed on a roller (rotating at ~2 Hz.) positioned inside a 37° C. incubator. After each storage period, samples were filtered using a sterile 0.20 μm filter (Sarstedt, Canada), and filtrates stored at 7° C. prior to in vitro evaluation.

Fibroblast Cell Culture

Immortalized rat fibroblasts (NIH-3T3; American Type Tissue Collection, Manassas, Va.) at passages 15-20 were used for experiments. The cells were grown in 75-cm² tissue culture flasks in Dulbecco's Modified Eagle's Medium (DMEM) supplemented with 5% fetal calf serum (FCS; heat-inactivated at 56° C. for 60 min). Cells were passaged twice weekly at 70% confluence, using 2 mL of 0.25% trypsin-EDTA to detach cells, and re-suspended in 8 mL of DMEM. Flasks were maintained in a humidified atmosphere at 37° C. and 10% $CO_2$. No antibiotics were used during routine subdivisions or for cell culture experiments to avoid altering cell metabolism. Fibroblasts for use in experiments were harvested at 70% confluence, detached using trypsin-EDTA, suspended at a concentration of $1 \times 10^4$ cells/mL, and verified using a Coulter counter.

Assessment of Cell Viability (MTT Assay)

NIH-3T3 cells (200 μL) were seeded at a density of $1 \times 10^4$ cells/mL in 96-nontissue culture-treated polystyrene plates (CoStar, Corning, Canada). DMEM+5% FCS culture media plus sterile tissue culture water only was used as a negative control and culture media plus cells plus sterile tissue culture water used as a positive control. Serial dilutions were performed on all samples (at 25, 50, 75 and 100%) and performed in triplicate. Hence, 4 plates (corresponding to each dilution) were incubated for 24 h in a cell culture incubator at 37° C. (10% $CO_2$/95% air atmosphere). After 24 h, 5, 10 and 15 μL of sterile tissue culture water were added to each well in their respective plate (corresponding to 75, 50 and 25% dilutions). 20 μL of relevant experimental extracts were then added to appropriate wells for testing. The plate was incubated again for 24 h in a cell culture incubator at 37° C. (10% $CO_2$/95% air atmosphere). A 5 mg/mL solution of MTT reagent (M2128, Sigma Aldrich Canada) was prepared in phosphate-buffered saline, vortexed and sterile-filtered (0.20 μm). Post 24 h incubation of the plates, each well was exposed to the prepared MTT at an amount equal to 10% of the culture media volume. The four plates representing each set of dilutions were then returned to the incubator for 3 h. After incubation, MTT solubilisation solution (Catalog Code: M8910) was added to each well at a volume equal to the original culture media volume. Each well was gently stirred on a rotating table to enhance dissolution of the formazan crystals. Subsequently, the absorbance of each well was spectrophotometrically measured at a wavelength of 570 nm on a multidetection microplate reader (Synergy HT, BIO-TEK). Cell positive control wells were assumed to have 100% metabolic activity corresponding to cellular viability of 100% and the percentage cell viability of the cells exposed to experimental extracts were calculated relative to this.

Assessment of Cell Cytotoxicity (Release of LDH Assay)

The lactate dehydrogenase (LDH) assay was measured by a colorimetric lactate dehydrogenase (LDH) assay (TOX-7 (Product Code: 050M6079), Sigma Aldrich, Canada), according to instructions from the supplier. The amount of LDH in the medium is proportional to the number of lysed/dead cells present; therefore, this assay can be used to estimate cell death. This assay measures membrane integrity as a function of the amount of cytoplasmic LDH released into the medium. Briefly, assay mixture was prepared by mixing equal amounts of LDH assay substrate (Catalog Number: L2402), cofactor (Catalog Number: L2527) and dye solutions (Catalog Number: L2277). For all cultures (70 µL), assay mixture was added to the medium in a proportion of two to one in 4×96-nontissue culture-treated polystyrene plates (CoStar, Corning, Canada). Each plate corresponds to medium dilutions of 25, 50, 75 and 100%, respectively. After incubation at room temperature in the dark (each plate covered with Al foil) and through gentle rotation on a roller, the color reaction was stopped by 1 N HCl. Similar to the MTT assay, DMEM+5% FCS culture media plus sterile tissue culture water only was used as a negative control and culture media plus cells plus sterile tissue culture water used as a positive control. Absorbance was determined at 490 nm using a multidetection microplate reader (Synergy HT, BIO-TEK), with the background correction performed at 650 nm.

Statistical Analysis

Figure 18A:
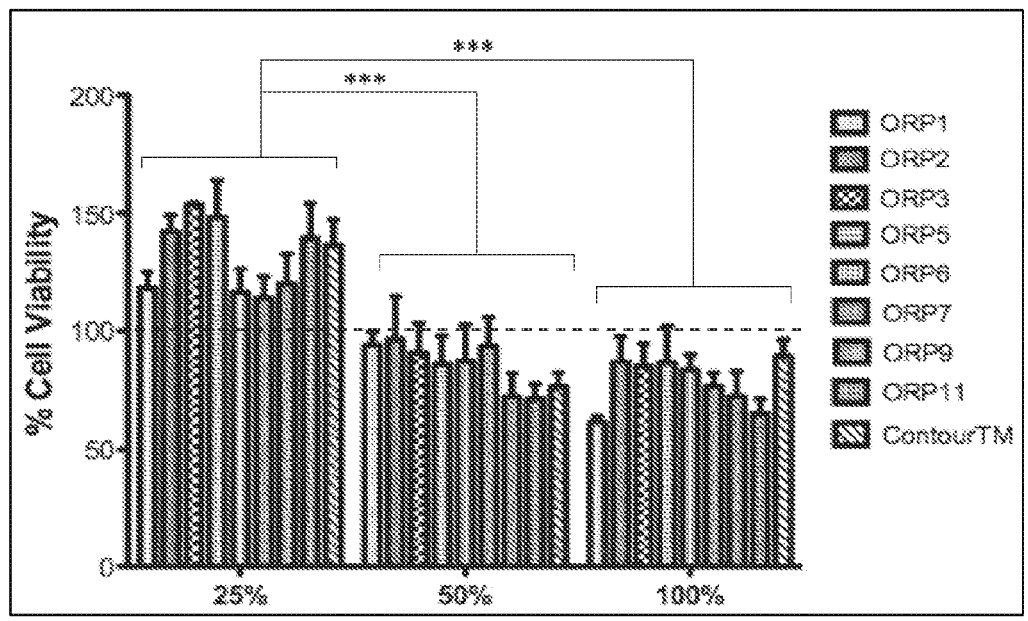
FIG. 18 presents cell viability and cell toxicity data.
Figure 18B:
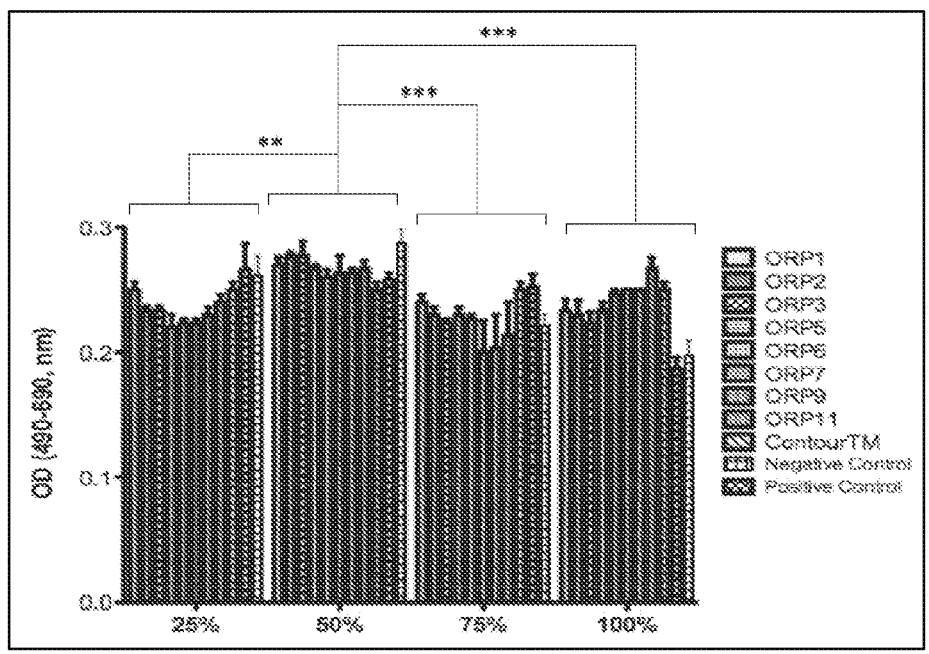
Figure 19A:
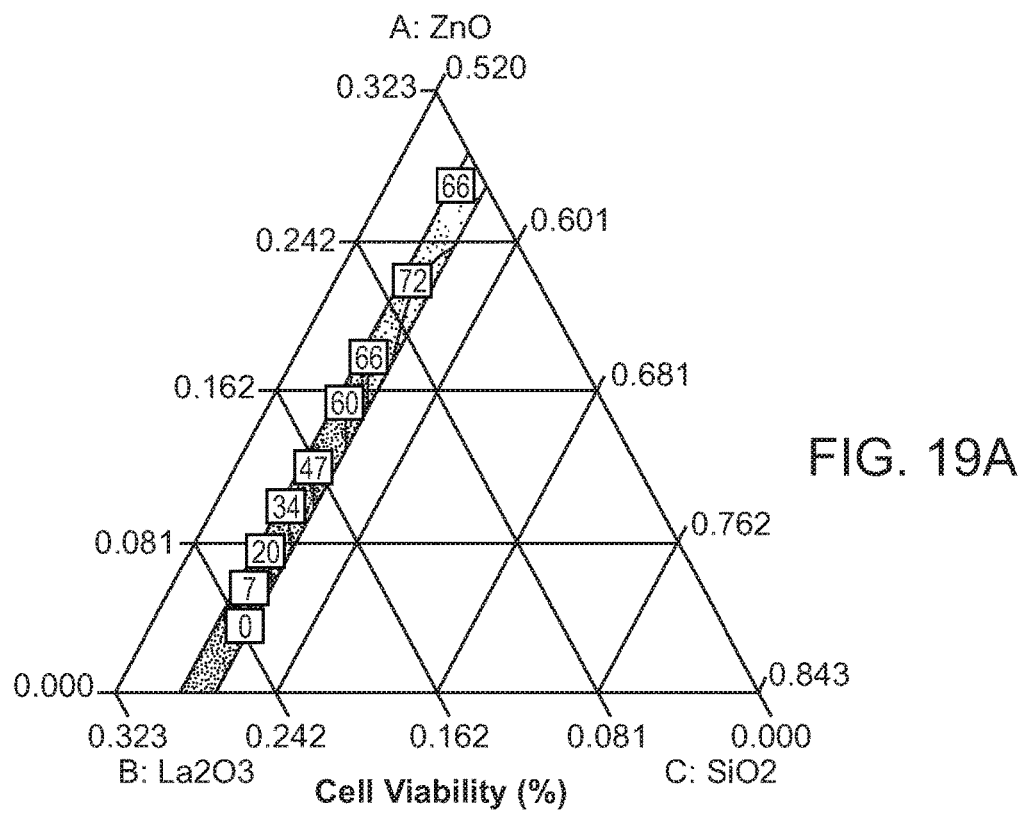
FIG. 19 presents contour plots' showing the compositional-interaction effects on the experimental embolic materials cell viability (%) at four various additions of Ti.
Figure 19B:
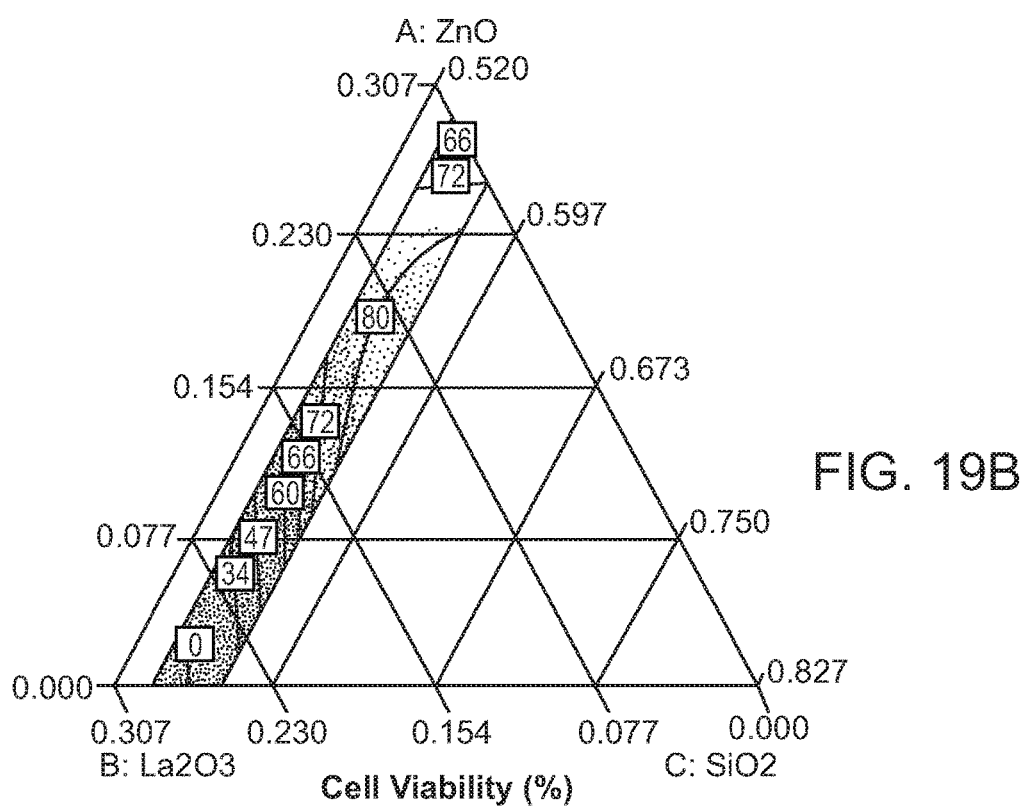
Figure 19C:
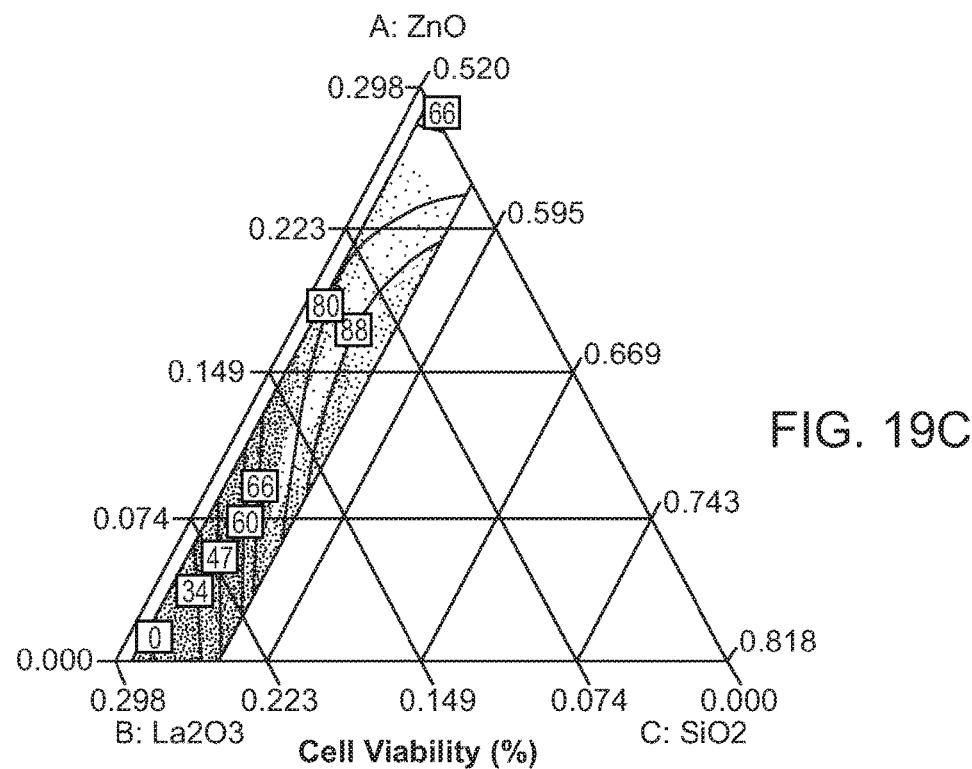
Figure 19D:
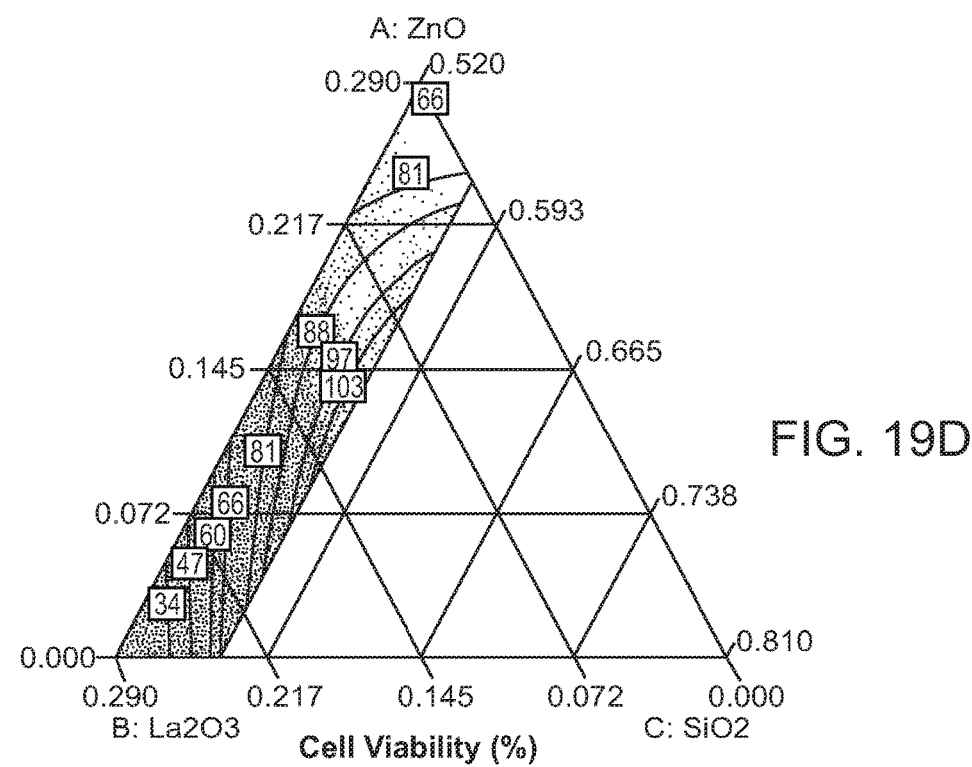

Each experiment was performed in triplicate and analysed using Prism 5.0 software (GraphPad software, Inc.) Results are expressed as mean±standard deviation of the triplicate determinations. One way analysis of variance (ANOVA) was carried out followed by a Tukey's post hoc test for comparisons between groups. The level of significance was set at $p<0.05$. FIG. 18A presents cell viability in the presence of ORP1-3, ORP5-7, ORP9 and ORP11 and Contour™ for 24 h embolic particulate extracts at 25, 50 and 100% serial dilutions. Results represent mean±SD (no significant statistical differences ($p<0.05$) were observed between any of the extracts tested). FIG. 18B presents cell toxicity in the presence of ORP1-3, ORP5-7, ORP9 and ORP11 and Contour™ for 24 h embolic particulate extracts at 25, 50, 75 and 100% serial dilutions. Results represent mean±SD (no significant statistical differences ($p<0.05$) were observed between any of the extracts tested). FIG. 19 presents contour plots' showing the compositional-interaction effects on the experimental embolic materials cell viability (%) at four various additions of Ti (0.017 (FIG. 19A), 0.033 (FIG. 19B), 0.042 (FIG. 19C) and 0.05 mol. (FIG. 19D)) in actual component coding.

Table 21 provides the final regression equations in terms of L_Pseudo (1); Actual components (2) and $R^2$ values; and summarized ANOVA for cell viability. The ANOVA data demonstrates that the model adequately predicts the cell viability response of the particulate material.

TABLE 21

| | | | Summarized ANOVA | | | | | |
|---|---|---|---|---|---|---|---|---|
| Response | | Regression Models | $R^2$ | $R^2_{adj.}$ | $R^2_{pred.}$ | Prob > F | CV (%) | Adeq. Prec. |
| Cell Viability (%) | 1 | $+66.63 ZnO - 145.51 La_2O_3 + 338.30 SiO_2 + 815.98 TiO_2 + 265.33 ZnO * La_2O_3 - 365.03 ZnO * SiO_2 - 913.28 ZnO * TiO_2$ | 0.9999 | 0.9994 | 0.9817 | 0.0179 | 0.36 | 123.770 |
| | 2 | $+1236.37607 ZnO - 1029.59161 La_2O_3 + 393.36925 SiO_2 + 1798.32577 TiO_2 + 2295.21826 ZnO * La_2O_3 - 3157.72134 ZnO * SiO_2 - 7900.33004 ZnO * TiO_2$ | | | | | | |

Table 22 provides the residuals of the cell viability study for all material compositions synthesized.

TABLE 22

| | Cell Viability (%) | | | |
|---|---|---|---|---|
| Glass | Experimental Data | SD | Calculated Data | Residual (Difference) |
| ORP1 | 73.790 | °19.77 | 73.954 | −0.164 |
| ORP2 | 84.120 | °17.23 | 84.087 | −0.033 |
| ORP3 | 81.270 | °16.15 | 81.153 | 0.117 |
| ORP5 | 91.790 | °18.74 | 91.885 | −0.095 |
| ORP6 | 72.370 | °17.05 | 72.301 | 0.069 |
| ORP7 | 71.440 | °10.90 | 71.323 | 0.117 |
| ORP9 | 62.240 | °22.03 | 62.278 | −0.038 |
| ORP11 | 60.760 | °03.49 | 60.798 | −0.038 |

Table 23 provides the summary of the significant (positive and negative) main, interaction and quadratic compositional factors (ranked highest to lowest) and its effect on increasing cytocompatibility; where ↑ denotes an increase and ↓ a decrease. The data is based on actual component coding.

TABLE 23

| Ranking of Compositional Factors | Cell Viability Response |
|---|---|
| 1 | ↓$ZnO*TiO_2$ |
| 2 | ↑$TiO_2$ |
| 3 | ↓$ZnO*SiO_2$ |
| 4 | ↑$SiO_2$ |
| 5 | ↑$ZnO*La_2O_3$ |

The data demonstrates that the most significant 'main' compositional variants which impact upon cell viability at 75% are on the order $TiO_2>SiO_2$. An interesting feature is that, counter to what would be expected, ZnO in its own right does not contribute to a reduction in cell viability. Rather, ZnO is dependant on interactions with $TiO_2$ (Table 23 G; $ZnO*TiO_2$ is the $1^{st}$ most significant factor with respect to the MTT assay) to reduce cell viability; whereby a decrease in ZnO for an increase in $TiO_2$ may enhance cell viability. Similarly, the interactions between ZnO and $SiO_2$ indicates that decreased ratio of $ZnO:SiO_2$ will allow for enhanced cytocompatibility. Other surprising relationships shown in the data are described below.

It also would not have been predicted that increasing the ratio of $ZnO:La_2O_3$ provides for increased levels of cell viabilities. This interaction effect deems $La_2O_3$ more cytotoxic than ZnO. To the contrary, it would have been expected that the Zn containing materials described herein would demonstrate a cytotoxicity profile counter to requirements. However, it is clearly demonstrated that the complex multi-component system provides for tailored (equivalent or superior) cytocompatibility versus conventional embolic materials (Contour).

Evaluation of Radiopacity

Figure 20:
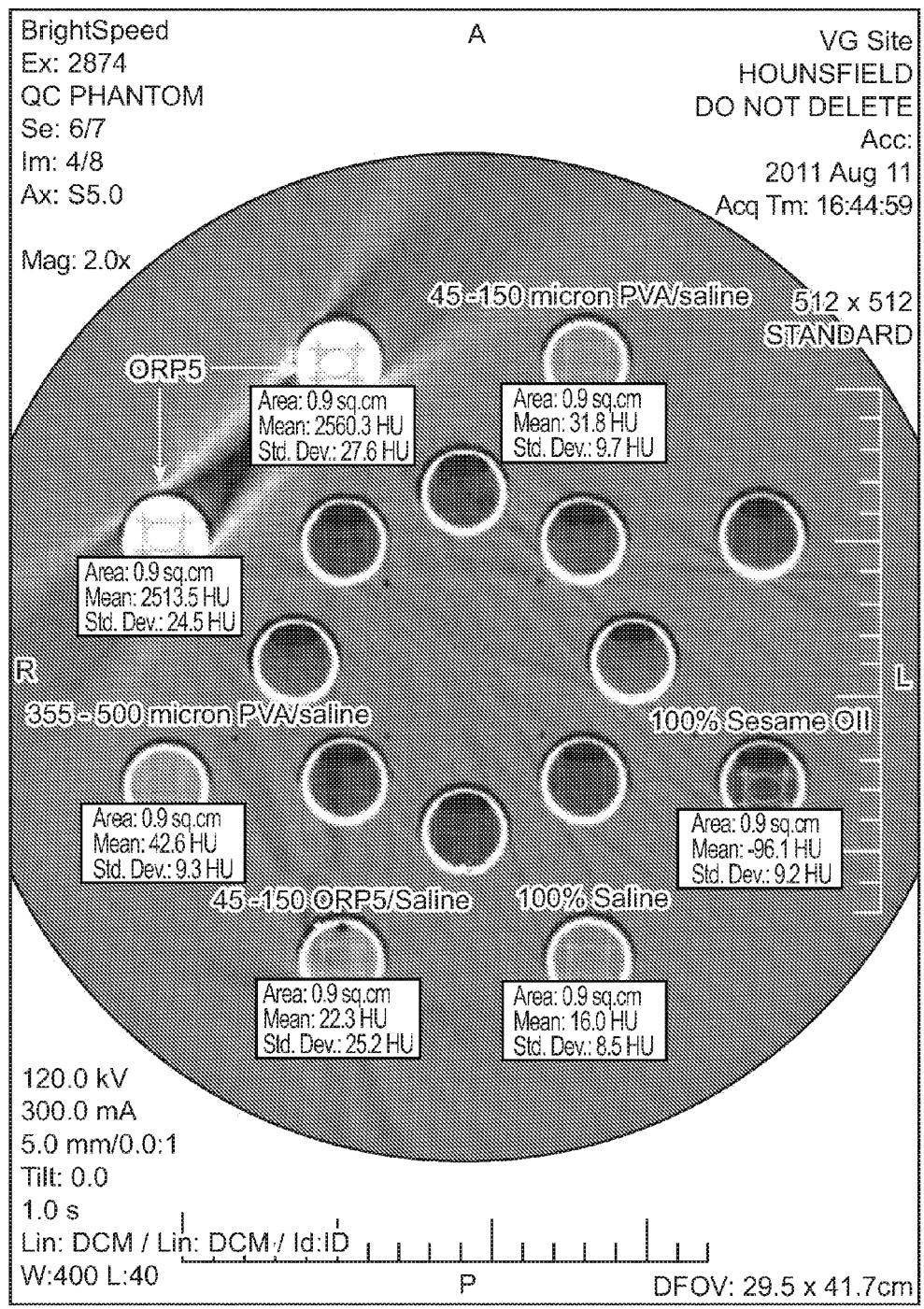
FIG. 20 presents a comparison of radiopacity for ORP vs. PVA in various dilutions of saline/contrast agent.

Radiopacity of OccluRad versus PVA (Contour) was determined using computed tomography scans of Gammex Tissue Characterization phantom inserts filled with each product. FIG. 20 is a comparison of radiopacity for ORP vs. PVA in various dilutions of saline/contrast agent. Results are provided in terms of the materials Hounsfield Unit (HU) values.

Due to the complexity of the multi-component systems (compositions) disclosed, one could not predict the response for each, with respect to its inherent radiopacity. It is noted that the HU values for ORP5 representative for all sets of compositions disclosed) demonstrates far superior levels to Contour in the absence of any contrast agent.

In Vivo Evaluation of Safety and Efficacy

Animal units (New Zealand White Rabbits) were used for a pilot examination of local effects after implantation in the uterine artery. Material (ORP 5) was delivered to the relevant vasculature, using a 25G butterfly cannulae, in a suspension of saline (8 mg/mL). 8 animals were utilized; 4 treated with ORP5 and 4 with Contour. Animals were euthanized after 21 days, using Isofluorane and KCl (the latter administered via IV at 2 mg/kg). Laparotomy was performed, and the uterus, including both ovaries, was removed. The left and right uterine horns were dissected, fixed in 10% formaldehyde solution and sectioned appropriately for histological evaluation. Histological samples were taken at four to six different levels (depending on size) along the uterine horn; routine hematoxylin and eosin staining was performed thereafter.

Figure 21A:
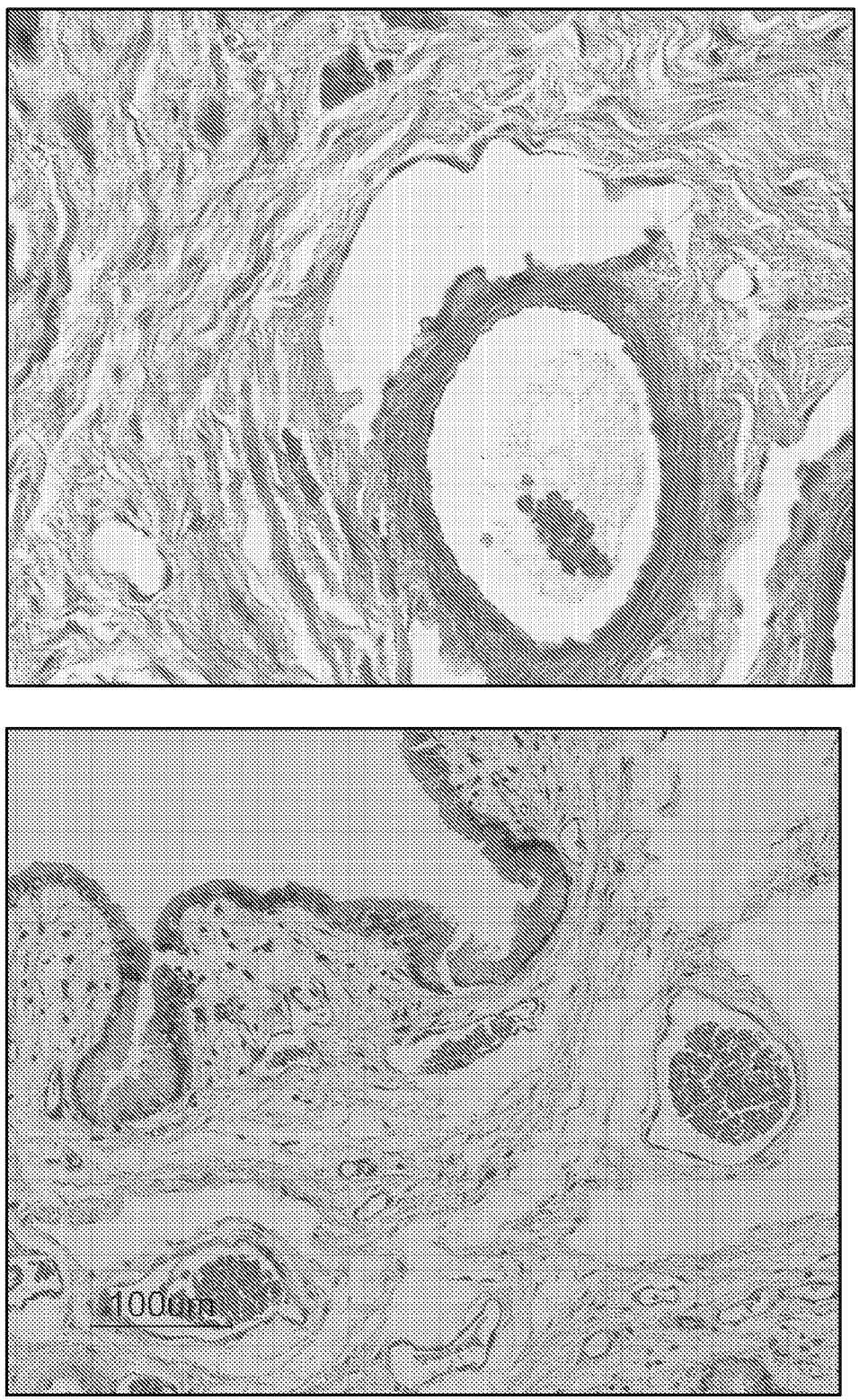
FIG. 21 presents histological data, derived from one animal in each group, with respect to the performance of ORP5 and Contour.
Figure 21B:
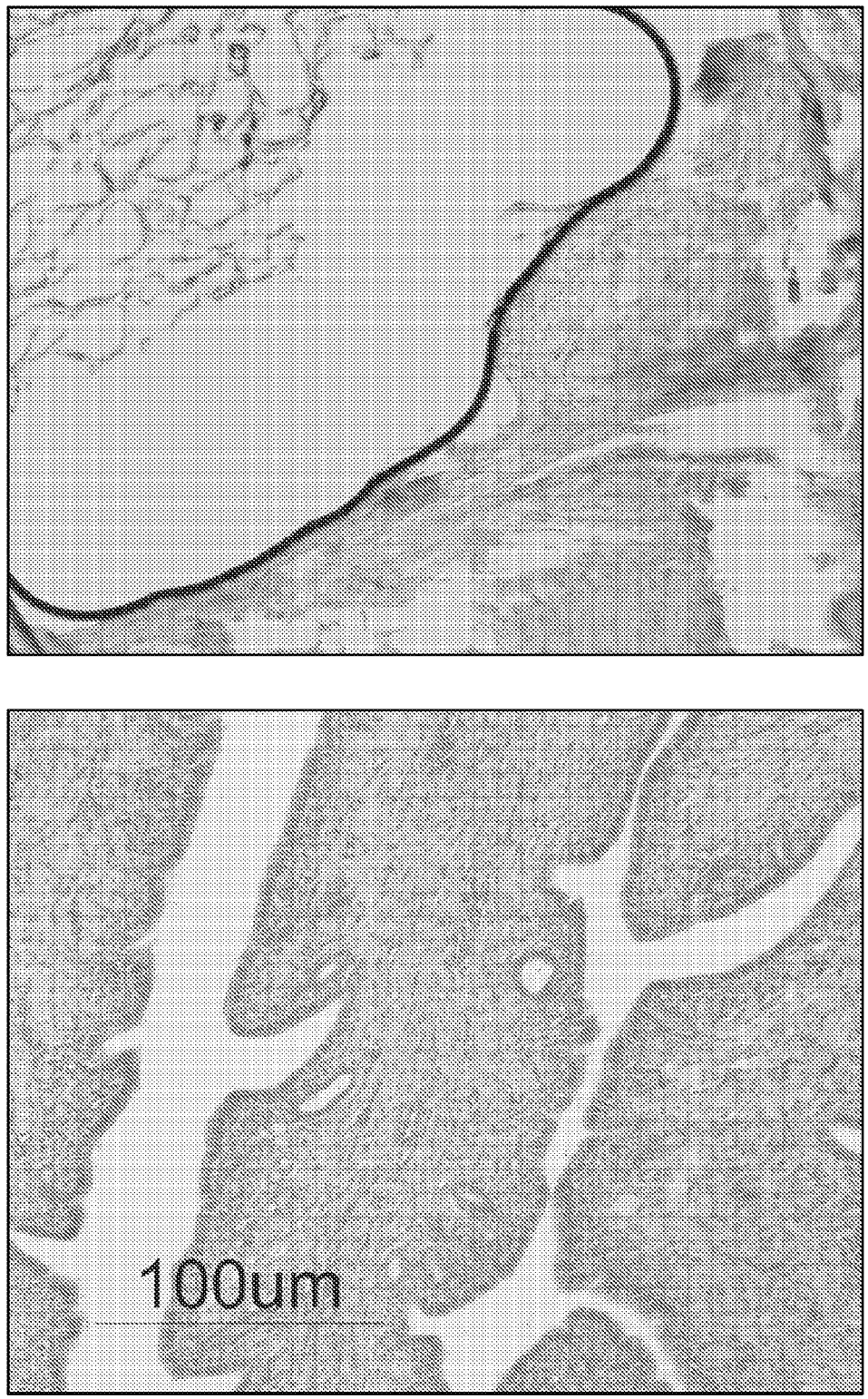
Figure 21C:
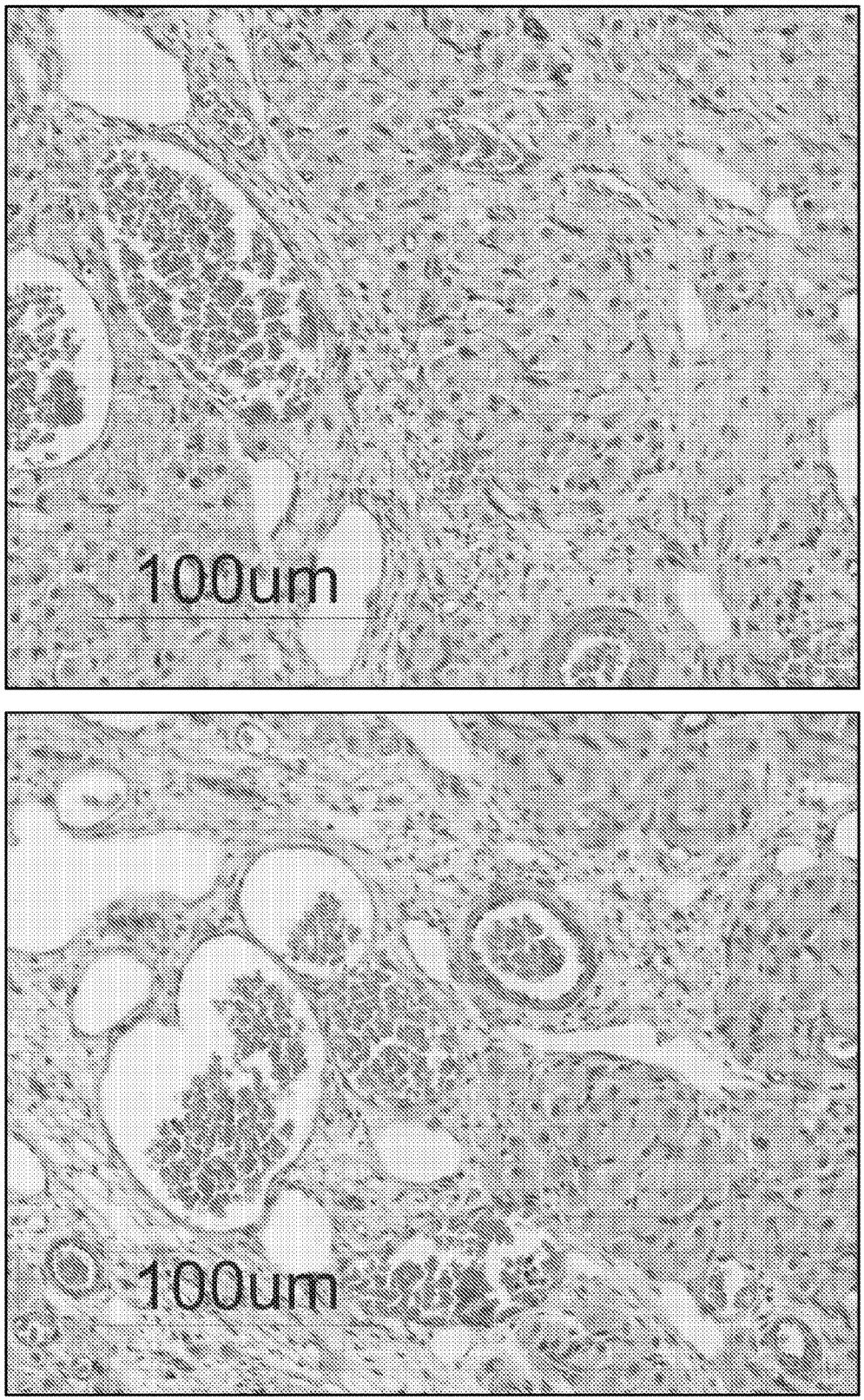

FIG. 21 presents histological data, derived from one animal in each group, with respect to the performance of Contour (FIG. 21A), ORP5 (FIG. 21B) and Control (FIG. 21C).

That ORP5 worked as well as and in some measures, out performed, the Contour could not have been predicted. Gross examination of the pathology specimens from all 8 rabbits showed a necrotic uterus at the embolization site, with no obvious changes in any of the untreated uterine horns. No adverse reactions were observed for any of the H&E stained tissues examined (in both experimental and commercial groups) with comparable data to untreated (normal) uterine tissues. In the intracutaneous irritation test, there was no evidence of irritation in both the polar (normal saline) and non-polar (sesame oil) vehicles (the mean score difference less than 1 in all observations), to demonstrate equivalency for ORP5 to the embolic predicate Contour.

Intracutaneous Irritation Test

Figure 22:
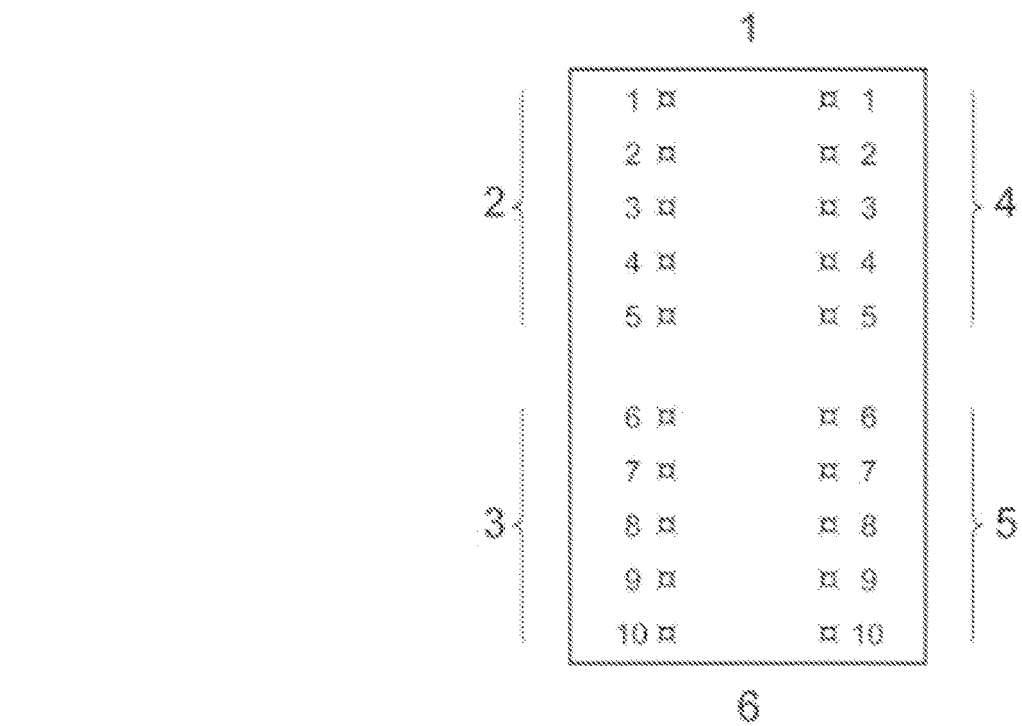
FIG. 22 illustrates the intracutaneous irritation test design of NZW Rabbits.

This study was conducted according to ISO 10993-10. The potential of the test article (extract of particle ORP5) producing irritation was evaluated after intracutaneous injection of the test article. Three New Zealand White rabbits were used in this study. Each rabbit was injected intracutaneously with 0.2 mL of test article or vehicles. The polar vehicle was normal saline, and the nonpolar vehicle was sesame oil. The treatment designs of each animal are presented in FIG. 22. Table 24 provides the Draize grading system for the experiment.

TABLE 24

| Reaction | Numerical Grading |
|---|---|
| 1. Erythema and eschar formation | |
| No erythema | 0 |
| Very slight erythema (barely perceptible) | 1 |
| Well-defined erythema | 2 |
| Moderate erythema | 3 |
| Severe erythema (beet-redness) to escher formation preventing grading of erythema | 4 |
| 2. Edema formation | |
| No edema | 0 |
| Very slight edema (barely perceptible) | 1 |
| Well-defined edema (edges of area well-defined by definite raising) | 2 |
| Moderate edema (raised approximately 1 mm) | 3 |
| Severe erythema (raised approximately 1 mm and extending beyond exposure area) | 4 |

Figure 23:
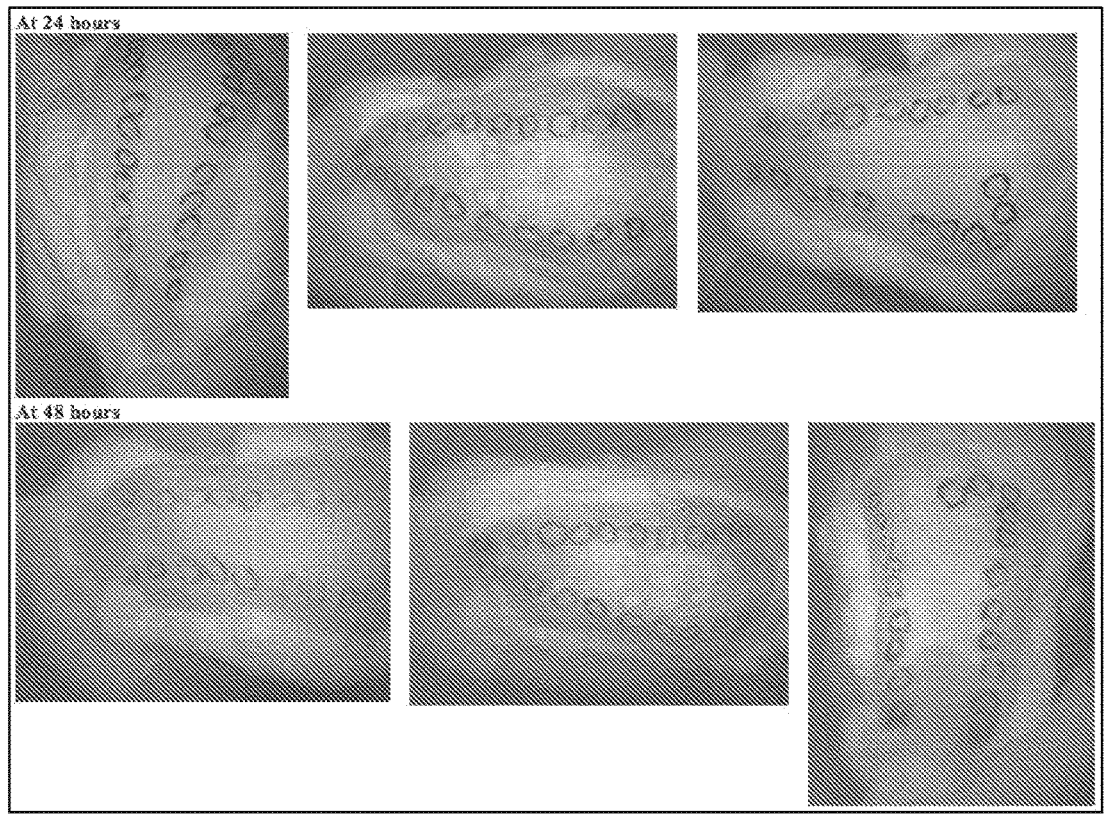
FIG. 23 are images of the intradermal injection sites for the three NZW rabbits after 24, 48 and 72 h observations.
Figure 23:
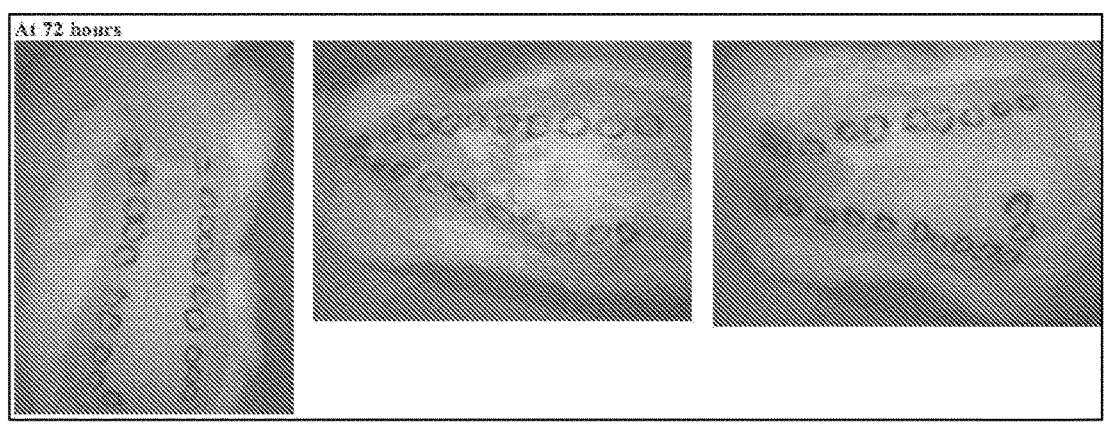

The appearance of each injection site was noted and marked immediately after injection. Observation of the tissue reaction at 0 hours (immediately after injection), 24 hours, 48 hours, and 72 hours after injection were graded. Any reaction at the injection site was recorded accordingly. FIG. 23 provides images of the intradermal injection sites for the three NZW rabbits after 24, 48 and 72 h observations.

Conformation of Fibrinogen in Embolic Extracts Containing Degradation Products

Figure 24:
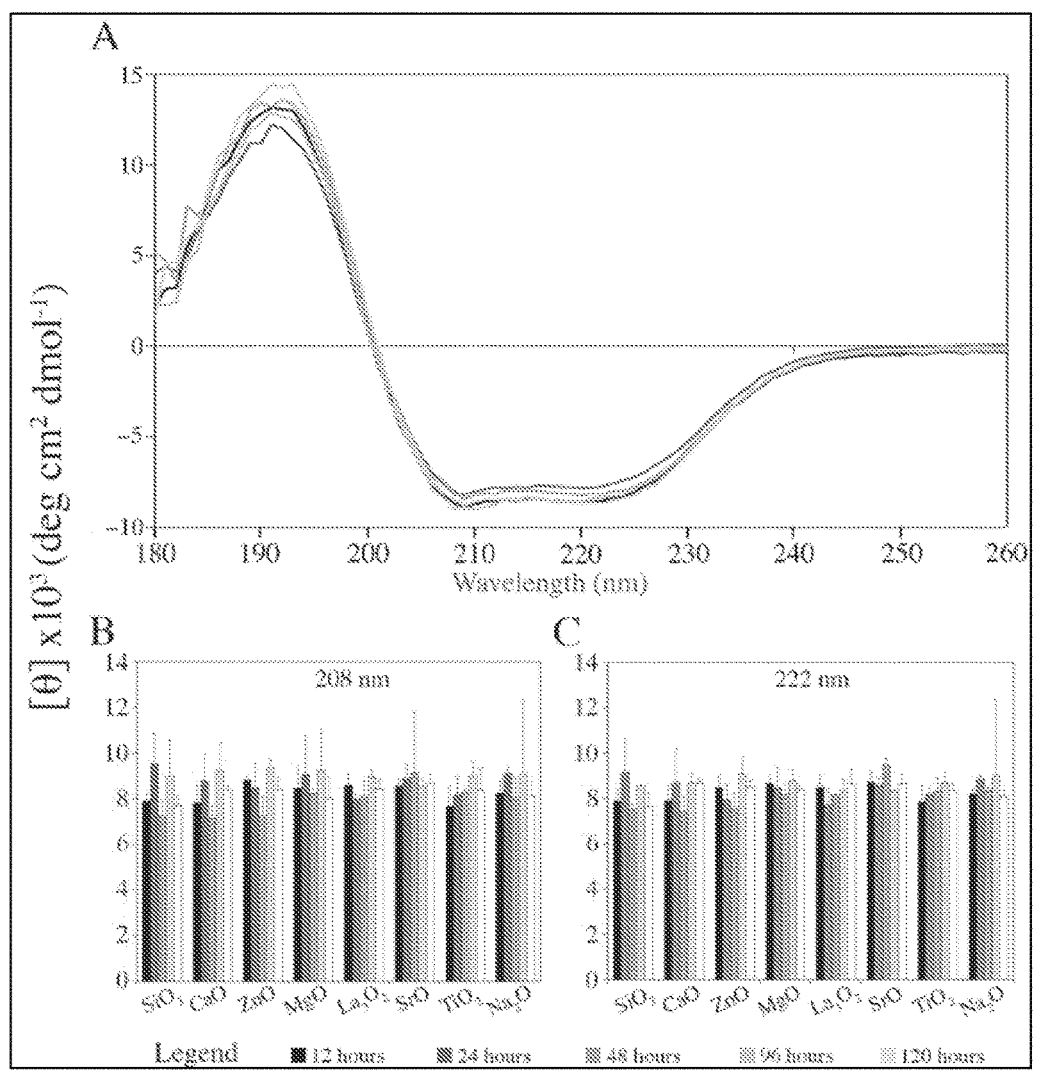
FIG. 24 illustrates changes in Fg conformation monitored by far-ultraviolet circular dichroism (CD) spectroscopy as a function of the ionic dissolution products with respect to time.

Far-ultraviolet (UV) Circular Dichroism (CD) spectra were recorded using a Jasco J-810 spectropolarimeter (Easton, Md.) with temperature control capability. A 6.4 mg/mL solution of fibrinogen from human plasma (F4883, plasminogen free, containing 58% protein, 96% clottable protein; Sigma Aldrich, ON) in 25 mM sodium phosphate buffer adjusted to pH 7.4±0.05 using NaOH and $H_2SO_4$ was diluted to a concentration of 0.2 mg/mL with the solutions of embolic extracts (containing the ion degradation products, as prepared in Example 9 at n=3 for each extract)). The concentration of the stock fibrinogen solution was determined by UV spectroscopy at 280 nm using the manufacturer's molar extinction coefficient. All spectra were collected at 37° C. (controlled with a NESLAB RTE-111 bath, Thermo Scientific, Newington, N.H.) in three repetitions (260-190 nm, 1 nm steps, 50 nm/min) in a 0.5 mm pathlength quartz cuvette (Hellma, Müllheim, Germany). The triplicate spectra for each ion degradation solution were averaged, blank subtracted with phosphate buffer (25 mM; pH 7.4±0.05), and converted to mean residue ellipticity ([θ]). Relative fibrinogen conformation between samples was monitored by comparing [θ] at the minima corresponding to the α-helical bands at ~208 and 222 nm. FIG. 24 illustrates changes in Fg conformation monitored by far-ultraviolet circular dichroism (CD) spectroscopy as a function of the ionic dissolution products with respect to time. FIG. 24A is an example of CD spectra for ORP5 over time. FIGS. 24B and C are intensity (mean of 3 replicates, blank subtracted; average deviation shown) at the minima at ~208 and 222 nm of Fg CD spectra for each ionic dissolution product. All data is reported in mean residue ellipticity [θ]. The provided legend applies for all three panels.

The effect of the degradation by-products from such complex multi-component systems on the secondary structure of fibrinogen, Fg (an essential precursor protein for clot formation) could not have been predicted. Interestingly, no significant conformational changes to Fg structure were observed by CD (FIG. 24), despite previous literature reports of this possibility. The response of platelets in contact with ORP5 and Contour using LDH assays could not have been predicted.

Platelet Lactate Dehydrogenase (LDH) Assay Studies

All protocols pertaining to the use of whole blood and platelets were approved by the Capital Health Research Ethics Board. The blood (31.5 mL) was collected via venipuncture from healthy, aspirin-free human volunteers at the Laboratory Blood Collection facility at the Victoria General Hospital in seven 4.5 mL glass BD Vacutarier tubes (Catalog No. 364606, Becton-Dickinson, Franklin Lakes, N.J.) containing an acid-citrated dextrose (ACD) anticoagulant. It is important to note that the first tube (4.5 mL) of blood was discarded, as it is rich in clotting factors, and then the remaining 27 mL was collected. Platelet rich plasma (PRP) was generated by centrifuging the ACD-anticoagulated blood (1500 rpm, 8 min, 25° C.) using an Eppendorf 5702 centrifuge. Careful transfer of the PRP to individual centrifuge tubes was completed using sterile plastic pasteur pipettes.

Platelet concentration was measured using a LH 785 CBC analyzer. The platelet concentration was recorded for each patient but not adjusted. The platelet suspension was then added to the preferred particles (ORP5 and Contour™) at a final concentration of 0.1 cc per mL of platelet suspension (3 mL of patient PRP for each embolic agent with the exception of patient 1006 which only had enough PRP to add 2.5 ml of PRP per embolic agent) and allowed to adhere for 1 h at 37° C. under static conditions.

Figure 25A:
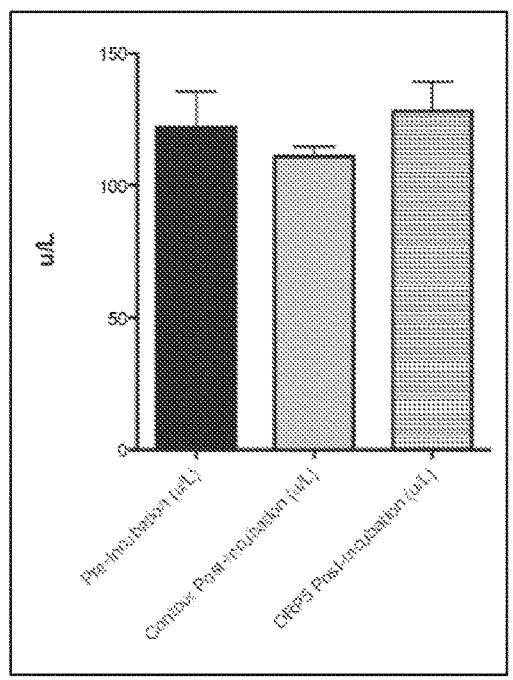
FIG. 25 illustrates results for platelet LDH assay (ORP5 vs. PVA) with (FIG. 25A) and without (FIG. 25B) outlier.
Figure 25B:
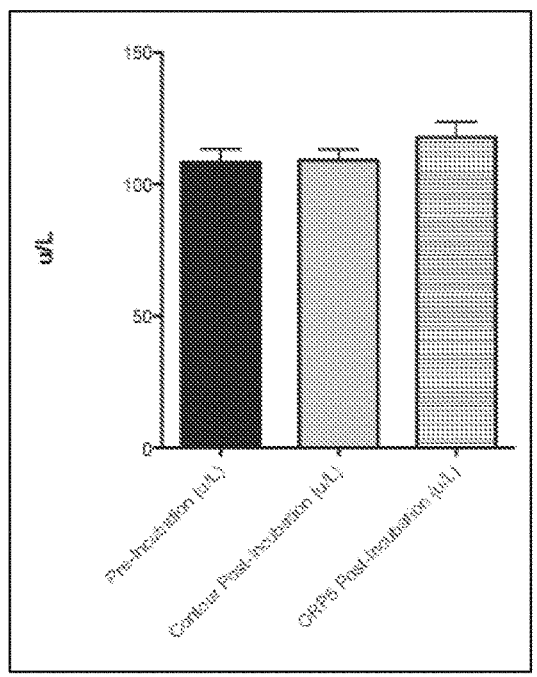

At the end of this step, the suspension was aspirated from each well, and the non-adherent platelets were rinsed away by filling and aspirating the wells ten times with 2.5 mL of PBS. The entire duration from blood collection to the conclusion of this step was less than 4 h. Platelet LDH was quantified by measuring the lactate dehydrogenase (LDH) released when the adherent platelets were lysed with a Triton-PSB buffer. A calibration curve was constructed using a known number of platelets and the platelet adhesion on the embolic agents was determined from this calibration curve. FIG. 25 illustrates results for platelet LDH assay (ORP5 vs. PVA) with (FIG. 25A) and without (FIG. 25B) outlier.

Given the complexity of the disclosed compositions, one could not have predicted the response of platelets to the material using the LDH assay. It is noted that performance of the multi-component systems in this assay demonstrate equivalent compatibility to Contour.

All publications and patent applications cited in this specification are herein incorporated by reference as if each individual publication or patent application were specifically and individually indicated to be incorporated by reference.

Although the foregoing invention has been described in some detail by way of illustration and example for purposes of clarity of understanding, it will be readily apparent to one of ordinary skill in the art in light of the teachings of this invention that certain changes and modifications may be made thereto without departing from the spirit or scope of the invention as defined in the appended claims.

REFERENCES

1. Zhang X F, Kehoe S, Adhi S K, Ajithkumar T G, Moane S, O'Shea H, Boyd D, Composition-structure-property ($Zn^{2+}$ and $Ca^{2+}$ ion release) evaluation of Si—Na—Ca—Zn—Ce glasses: Potential components for nerve guidance conduits. Materials Science and Engineering C 2011; doi:10.1016/j.msec.2010.12.016
2. Murphy S, Boyd D, Moane S, and Bennett M. The effect of composition on ion release from Ca—Sr—Na—Zn—Si glass bone grafts. J Mater Sci Mater Med 2009; 20: 2207-2214.
3. Duee, C., et al., Mixture designs applied to glass bioactivity evaluation in the Si—Ca—Na system. Journal of Non-Crystalline Solids, 2009. 355(16-17): p. 943-950.
4. Akalin, O., et al., *Optimization of chemical admixture for concrete on mortar performance tests using mixture experiments*. Chemometrics and Intelligent Laboratory Systems, 2010. 104(2): p. 233-242.
5. Papelis C, Um W, Russell C E, and Chapman J B. Measuring the specific surface area of natural and man-made glasses: effects of formation process, morphology, and particle size. Colloids and Surfaces a-Physicochemical and Engineering Aspects 2003; 215: 221-239.
6. Ning J, Yao A, Wang D P, Huang W H, Fu H L, Liu X, Jiang X Q, and Zhang X L. Synthesis and in vitro bioactivity of a borate-based bioglass. Materials Letters 2007; 61: 5223-5226.
7. Cheung S, Gauthier M, Lefebvre L P, Dunbar M, and Filiaggi M. Fibroblastic interactions with high-porosity Ti-6Al-4V metal foam. Journal of Biomedical Materials Research Part B-Applied Biomaterials 2007; 82B: 440-449.

TABLE 2

177 glass compositions (mol. fraction) formulated using design of experiments. The NM components are varied between 0 to 0.140 mol. fraction.

| Std. ORP# | Run | Si | Ca | Zn | Mg | La | Sr | Ti | Na |
|---|---|---|---|---|---|---|---|---|---|
| 78 | 1 | 0.000 | 0.150 | 0.520 | 0.050 | 0.140 | 0.000 | 0.140 | 0.000 |
| 4 | 2 | 0.290 | 0.000 | 0.570 | 0.000 | 0.000 | 0.140 | 0.000 | 0.000 |
| 17 | 3 | 0.290 | 0.140 | 0.520 | 0.050 | 0.000 | 0.000 | 0.000 | 0.000 |
| 132 | 4 | 0.000 | 0.000 | 0.570 | 0.050 | 0.100 | 0.140 | 0.000 | 0.140 |
| 150 | 5 | 0.000 | 0.150 | 0.520 | 0.050 | 0.000 | 0.000 | 0.140 | 0.140 |
| 73 | 6 | 0.200 | 0.000 | 0.520 | 0.000 | 0.140 | 0.000 | 0.140 | 0.000 |
| 6 | 7 | 0.290 | 0.000 | 0.570 | 0.000 | 0.000 | 0.000 | 0.000 | 0.140 |
| 43 | 8 | 0.290 | 0.000 | 0.520 | 0.000 | 0.140 | 0.000 | 0.050 | 0.000 |
| 10 | 9 | 0.000 | 0.290 | 0.570 | 0.000 | 0.000 | 0.000 | 0.140 | 0.000 |
| 125 | 10 | 0.000 | 0.200 | 0.520 | 0.000 | 0.000 | 0.140 | 0.000 | 0.140 |
| 14 | 11 | 0.290 | 0.000 | 0.520 | 0.050 | 0.000 | 0.140 | 0.000 | 0.000 |
| 142 | 12 | 0.000 | 0.010 | 0.520 | 0.050 | 0.140 | 0.140 | 0.000 | 0.140 |
| 121 | 13 | 0.000 | 0.100 | 0.570 | 0.050 | 0.140 | 0.000 | 0.000 | 0.140 |
| 20 | 14 | 0.000 | 0.290 | 0.520 | 0.050 | 0.000 | 0.000 | 0.140 | 0.000 |
| 144 | 15 | 0.000 | 0.000 | 0.520 | 0.050 | 0.140 | 0.140 | 0.010 | 0.140 |
| 171 | 16 | 0.000 | 0.000 | 0.570 | 0.010 | 0.000 | 0.140 | 0.140 | 0.140 |
| 62 | 17 | 0.000 | 0.100 | 0.570 | 0.050 | 0.140 | 0.140 | 0.000 | 0.000 |
| 152 | 18 | 0.000 | 0.100 | 0.570 | 0.050 | 0.000 | 0.140 | 0.140 | 0.140 |
| 151 | 19 | 0.100 | 0.000 | 0.570 | 0.050 | 0.000 | 0.000 | 0.140 | 0.140 |
| 15 | 20 | 0.290 | 0.000 | 0.520 | 0.050 | 0.000 | 0.140 | 0.000 | 0.000 |
| 153 | 21 | 0.000 | 0.000 | 0.570 | 0.050 | 0.100 | 0.000 | 0.140 | 0.140 |
| 27 | 22 | 0.290 | 0.090 | 0.570 | 0.050 | 0.000 | 0.000 | 0.000 | 0.000 |
| 8 | 23 | 0.000 | 0.290 | 0.570 | 0.000 | 0.140 | 0.000 | 0.000 | 0.000 |
| 145 | 24 | 0.200 | 0.000 | 0.520 | 0.000 | 0.000 | 0.000 | 0.140 | 0.140 |

TABLE 2-continued 177 glass compositions (mol. fraction) formulated using design of experiments. The NM components are varied between 0 to 0.140 mol. fraction.

| Std. ORP# | Run | Si | Ca | Zn | Mg | La | Sr | Ti | Na |
|---|---|---|---|---|---|---|---|---|---|
| 63 | 25 | 0.290 | 0.000 | 0.520 | 0.000 | 0.000 | 0.000 | 0.140 | 0.050 |
| 134 | 26 | 0.060 | 0.000 | 0.520 | 0.000 | 0.140 | 0.140 | 0.000 | 0.140 |
| 107 | 27 | 0.290 | 0.000 | 0.520 | 0.000 | 0.000 | 0.000 | 0.050 | 0.140 |
| 148 | 28 | 0.000 | 0.150 | 0.570 | 0.000 | 0.000 | 0.000 | 0.140 | 0.140 |
| 160 | 29 | 0.000 | 0.000 | 0.570 | 0.010 | 0.140 | 0.000 | 0.140 | 0.140 |
| 120 | 30 | 0.100 | 0.000 | 0.570 | 0.050 | 0.140 | 0.000 | 0.000 | 0.140 |
| 75 | 31 | 0.150 | 0.000 | 0.570 | 0.000 | 0.140 | 0.000 | 0.140 | 0.000 |
| 128 | 32 | 0.150 | 0.000 | 0.520 | 0.050 | 0.000 | 0.140 | 0.000 | 0.140 |
| 108 | 33 | 0.050 | 0.290 | 0.520 | 0.000 | 0.000 | 0.000 | 0.000 | 0.140 |
| 159 | 34 | 0.000 | 0.010 | 0.570 | 0.000 | 0.140 | 0.000 | 0.140 | 0.140 |
| 24 | 35 | 0.290 | 0.000 | 0.570 | 0.050 | 0.000 | 0.090 | 0.000 | 0.000 |
| 164 | 36 | 0.000 | 0.000 | 0.530 | 0.050 | 0.140 | 0.000 | 0.140 | 0.140 |
| 9 | 37 | 0.000 | 0.290 | 0.570 | 0.000 | 0.000 | 0.140 | 0.000 | 0.000 |
| 124 | 38 | 0.200 | 0.000 | 0.520 | 0.000 | 0.000 | 0.140 | 0.000 | 0.140 |
| 90 | 39 | 0.100 | 0.000 | 0.570 | 0.050 | 0.000 | 0.140 | 0.140 | 0.000 |
| 126 | 40 | 0.150 | 0.000 | 0.570 | 0.000 | 0.000 | 0.140 | 0.000 | 0.140 |
| 174 | 41 | 0.000 | 0.010 | 0.520 | 0.050 | 0.000 | 0.140 | 0.140 | 0.140 |
| 141 | 42 | 0.010 | 0.000 | 0.520 | 0.050 | 0.140 | 0.140 | 0.000 | 0.140 |
| 7 | 43 | 0.290 | 0.140 | 0.570 | 0.000 | 0.000 | 0.000 | 0.000 | 0.000 |
| 92 | 44 | 0.000 | 0.000 | 0.570 | 0.050 | 0.100 | 0.140 | 0.140 | 0.000 |
| 74 | 45 | 0.000 | 0.200 | 0.520 | 0.000 | 0.140 | 0.000 | 0.140 | 0.000 |
| 122 | 46 | 0.000 | 0.000 | 0.570 | 0.050 | 0.140 | 0.100 | 0.000 | 0.140 |
| 135 | 47 | 0.000 | 0.060 | 0.520 | 0.000 | 0.140 | 0.140 | 0.000 | 0.140 |
| 64 | 48 | 0.290 | 0.050 | 0.520 | 0.000 | 0.000 | 0.000 | 0.140 | 0.000 |
| 93 | 49 | 0.000 | 0.000 | 0.520 | 0.000 | 0.140 | 0.140 | 0.140 | 0.060 |
| 12 | 50 | 0.140 | 0.290 | 0.570 | 0.000 | 0.000 | 0.000 | 0.000 | 0.000 |
| 95 | 51 | 0.000 | 0.060 | 0.520 | 0.000 | 0.140 | 0.140 | 0.140 | 0.000 |
| 119 | 52 | 0.000 | 0.150 | 0.520 | 0.050 | 0.140 | 0.000 | 0.000 | 0.140 |
| 162 | 53 | 0.010 | 0.000 | 0.520 | 0.050 | 0.140 | 0.000 | 0.140 | 0.140 |
| 69 | 54 | 0.000 | 0.290 | 0.520 | 0.000 | 0.050 | 0.000 | 0.140 | 0.000 |
| 80 | 55 | 0.100 | 0.000 | 0.570 | 0.000 | 0.140 | 0.000 | 0.140 | 0.000 |
| 112 | 56 | 0.240 | 0.000 | 0.570 | 0.050 | 0.000 | 0.000 | 0.000 | 0.140 |
| 49 | 57 | 0.050 | 0.290 | 0.520 | 0.000 | 0.000 | 0.140 | 0.000 | 0.000 |
| 157 | 58 | 0.000 | 0.000 | 0.520 | 0.000 | 0.140 | 0.060 | 0.140 | 0.140 |
| 133 | 59 | 0.000 | 0.000 | 0.570 | 0.050 | 0.000 | 0.140 | 0.100 | 0.140 |
| 23 | 60 | 0.290 | 0.000 | 0.570 | 0.050 | 0.090 | 0.000 | 0.000 | 0.000 |
| 86 | 61 | 0.000 | 0.150 | 0.570 | 0.000 | 0.000 | 0.140 | 0.140 | 0.000 |
| 47 | 62 | 0.000 | 0.290 | 0.520 | 0.000 | 0.000 | 0.140 | 0.050 | 0.000 |
| 21 | 63 | 0.000 | 0.290 | 0.520 | 0.050 | 0.000 | 0.000 | 0.000 | 0.140 |
| 19 | 64 | 0.000 | 0.290 | 0.520 | 0.050 | 0.000 | 0.140 | 0.000 | 0.000 |
| 71 | 65 | 0.240 | 0.000 | 0.570 | 0.050 | 0.000 | 0.000 | 0.140 | 0.000 |
| 56 | 66 | 0.000 | 0.150 | 0.570 | 0.000 | 0.140 | 0.140 | 0.000 | 0.000 |
| 176 | 67 | 0.000 | 0.000 | 0.520 | 0.050 | 0.010 | 0.140 | 0.140 | 0.140 |
| 102 | 68 | 0.000 | 0.000 | 0.520 | 0.050 | 0.140 | 0.140 | 0.140 | 0.010 |
| 67 | 69 | 0.000 | 0.290 | 0.520 | 0.000 | 0.000 | 0.000 | 0.140 | 0.050 |
| 76 | 70 | 0.000 | 0.150 | 0.570 | 0.000 | 0.140 | 0.000 | 0.140 | 0.000 |
| 99 | 71 | 0.000 | 0.000 | 0.570 | 0.010 | 0.140 | 0.140 | 0.140 | 0.000 |
| 115 | 72 | 0.000 | 0.200 | 0.520 | 0.000 | 0.140 | 0.000 | 0.000 | 0.140 |
| 58 | 73 | 0.000 | 0.150 | 0.520 | 0.050 | 0.140 | 0.140 | 0.000 | 0.000 |
| 34 | 74 | 0.290 | 0.000 | 0.520 | 0.000 | 0.140 | 0.000 | 0.050 | 0.000 |
| 29 | 75 | 0.000 | 0.290 | 0.570 | 0.050 | 0.000 | 0.090 | 0.000 | 0.000 |
| 41 | 76 | 0.240 | 0.000 | 0.570 | 0.050 | 0.140 | 0.000 | 0.000 | 0.000 |
| 163 | 77 | 0.000 | 0.010 | 0.520 | 0.050 | 0.140 | 0.000 | 0.140 | 0.140 |
| 87 | 78 | 0.150 | 0.000 | 0.520 | 0.050 | 0.000 | 0.140 | 0.140 | 0.000 |
| 139 | 79 | 0.000 | 0.000 | 0.570 | 0.010 | 0.140 | 0.140 | 0.000 | 0.140 |
| 167 | 80 | 0.000 | 0.060 | 0.520 | 0.000 | 0.140 | 0.140 | 0.140 | 0.140 |
| 48 | 81 | 0.000 | 0.290 | 0.520 | 0.000 | 0.140 | 0.000 | 0.000 | 0.050 |
| 65 | 82 | 0.290 | 0.000 | 0.520 | 0.000 | 0.050 | 0.000 | 0.140 | 0.000 |
| 5 | 83 | 0.290 | 0.000 | 0.570 | 0.000 | 0.000 | 0.000 | 0.140 | 0.000 |
| 156 | 84 | 0.000 | 0.060 | 0.520 | 0.000 | 0.140 | 0.000 | 0.140 | 0.140 |
| 88 | 85 | 0.000 | 0.150 | 0.520 | 0.050 | 0.000 | 0.140 | 0.140 | 0.000 |
| 45 | 86 | 0.290 | 0.050 | 0.520 | 0.000 | 0.140 | 0.000 | 0.000 | 0.000 |
| 83 | 87 | 0.200 | 0.000 | 0.520 | 0.000 | 0.140 | 0.000 | 0.140 | 0.000 |
| 40 | 88 | 0.050 | 0.290 | 0.520 | 0.000 | 0.140 | 0.000 | 0.000 | 0.000 |
| 173 | 89 | 0.010 | 0.000 | 0.520 | 0.050 | 0.000 | 0.140 | 0.140 | 0.140 |
| 51 | 90 | 0.240 | 0.000 | 0.570 | 0.050 | 0.000 | 0.140 | 0.000 | 0.000 |
| 165 | 91 | 0.000 | 0.000 | 0.520 | 0.050 | 0.140 | 0.010 | 0.140 | 0.140 |
| 28 | 92 | 0.000 | 0.290 | 0.570 | 0.050 | 0.090 | 0.000 | 0.000 | 0.000 |
| 113 | 93 | 0.000 | 0.240 | 0.570 | 0.050 | 0.000 | 0.000 | 0.000 | 0.140 |
| 44 | 94 | 0.290 | 0.000 | 0.520 | 0.000 | 0.140 | 0.000 | 0.000 | 0.050 |
| 118 | 95 | 0.150 | 0.000 | 0.520 | 0.050 | 0.000 | 0.000 | 0.140 | 0.140 |
| 131 | 96 | 0.000 | 0.100 | 0.570 | 0.050 | 0.000 | 0.140 | 0.000 | 0.140 |
| 66 | 97 | 0.290 | 0.000 | 0.520 | 0.000 | 0.000 | 0.050 | 0.140 | 0.000 |
| 26 | 98 | 0.290 | 0.000 | 0.570 | 0.050 | 0.000 | 0.000 | 0.000 | 0.090 |
| 170 | 99 | 0.000 | 0.010 | 0.570 | 0.000 | 0.000 | 0.140 | 0.140 | 0.140 |
| 52 | 100 | 0.000 | 0.240 | 0.570 | 0.050 | 0.000 | 0.140 | 0.000 | 0.000 |
| 104 | 101 | 0.290 | 0.050 | 0.520 | 0.000 | 0.000 | 0.000 | 0.000 | 0.140 |
| 46 | 102 | 0.290 | 0.000 | 0.520 | 0.000 | 0.050 | 0.140 | 0.000 | 0.000 |
| 37 | 103 | 0.000 | 0.290 | 0.520 | 0.000 | 0.140 | 0.050 | 0.000 | 0.000 |
| 36 | 104 | 0.290 | 0.050 | 0.520 | 0.000 | 0.140 | 0.000 | 0.000 | 0.000 |
| 146 | 105 | 0.000 | 0.200 | 0.520 | 0.000 | 0.000 | 0.000 | 0.140 | 0.140 |
| 158 | 106 | 0.010 | 0.000 | 0.570 | 0.000 | 0.140 | 0.000 | 0.140 | 0.140 |
| 89 | 107 | 0.000 | 0.000 | 0.570 | 0.050 | 0.000 | 0.140 | 0.140 | 0.100 |
| 109 | 108 | 0.000 | 0.290 | 0.520 | 0.000 | 0.050 | 0.000 | 0.000 | 0.140 |
| 96 | 109 | 0.010 | 0.000 | 0.570 | 0.000 | 0.140 | 0.140 | 0.140 | 0.000 |
| 18 | 110 | 0.000 | 0.290 | 0.520 | 0.050 | 0.140 | 0.000 | 0.000 | 0.000 |
| 25 | 111 | 0.290 | 0.000 | 0.570 | 0.050 | 0.000 | 0.000 | 0.090 | 0.000 |
| 42 | 112 | 0.000 | 0.240 | 0.570 | 0.050 | 0.140 | 0.000 | 0.000 | 0.000 |
| 32 | 113 | 0.090 | 0.290 | 0.570 | 0.050 | 0.000 | 0.000 | 0.000 | 0.000 |
| 116 | 114 | 0.150 | 0.000 | 0.570 | 0.000 | 0.140 | 0.000 | 0.000 | 0.140 |
| 149 | 115 | 0.150 | 0.000 | 0.520 | 0.050 | 0.140 | 0.000 | 0.000 | 0.140 |
| 129 | 116 | 0.000 | 0.150 | 0.520 | 0.050 | 0.000 | 0.140 | 0.000 | 0.140 |
| 117 | 117 | 0.000 | 0.150 | 0.570 | 0.000 | 0.140 | 0.000 | 0.000 | 0.140 |
| 101 | 118 | 0.000 | 0.010 | 0.520 | 0.050 | 0.140 | 0.140 | 0.140 | 0.000 |
| 82 | 119 | 0.000 | 0.000 | 0.570 | 0.050 | 0.140 | 0.100 | 0.140 | 0.000 |
| 84 | 120 | 0.000 | 0.200 | 0.520 | 0.000 | 0.140 | 0.140 | 0.000 | 0.000 |
| 2 | 121 | 0.190 | 0.290 | 0.520 | 0.000 | 0.000 | 0.000 | 0.000 | 0.000 |
| 61 | 122 | 0.100 | 0.000 | 0.570 | 0.050 | 0.140 | 0.140 | 0.000 | 0.000 |
| 175 | 123 | 0.000 | 0.000 | 0.530 | 0.050 | 0.000 | 0.140 | 0.140 | 0.140 |
| 166 | 124 | 0.060 | 0.000 | 0.520 | 0.000 | 0.140 | 0.140 | 0.140 | 0.000 |
| 11 | 125 | 0.000 | 0.290 | 0.570 | 0.000 | 0.000 | 0.000 | 0.000 | 0.140 |
| 97 | 126 | 0.000 | 0.010 | 0.570 | 0.000 | 0.140 | 0.140 | 0.140 | 0.000 |
| 168 | 127 | 0.000 | 0.000 | 0.520 | 0.000 | 0.060 | 0.140 | 0.140 | 0.140 |
| 13 | 128 | 0.290 | 0.000 | 0.520 | 0.050 | 0.140 | 0.000 | 0.000 | 0.000 |
| 22 | 129 | 0.140 | 0.290 | 0.520 | 0.050 | 0.000 | 0.000 | 0.000 | 0.000 |
| 147 | 130 | 0.150 | 0.000 | 0.570 | 0.000 | 0.000 | 0.000 | 0.140 | 0.140 |
| 68 | 131 | 0.050 | 0.290 | 0.520 | 0.000 | 0.000 | 0.000 | 0.140 | 0.000 |
| 39 | 132 | 0.000 | 0.290 | 0.520 | 0.000 | 0.140 | 0.000 | 0.000 | 0.050 |
| 1 | 133 | 0.290 | 0.190 | 0.520 | 0.000 | 0.000 | 0.000 | 0.000 | 0.000 |
| 81 | 134 | 0.000 | 0.100 | 0.570 | 0.050 | 0.140 | 0.000 | 0.140 | 0.000 |
| 54 | 135 | 0.000 | 0.200 | 0.520 | 0.000 | 0.140 | 0.140 | 0.000 | 0.000 |
| 94 | 136 | 0.060 | 0.000 | 0.520 | 0.000 | 0.140 | 0.140 | 0.140 | 0.000 |
| 31 | 137 | 0.000 | 0.290 | 0.570 | 0.050 | 0.000 | 0.000 | 0.000 | 0.090 |
| 50 | 138 | 0.000 | 0.290 | 0.520 | 0.000 | 0.050 | 0.140 | 0.000 | 0.000 |
| 53 | 139 | 0.200 | 0.000 | 0.520 | 0.000 | 0.140 | 0.140 | 0.000 | 0.000 |
| 138 | 140 | 0.000 | 0.010 | 0.570 | 0.000 | 0.140 | 0.000 | 0.140 | 0.140 |
| 114 | 141 | 0.200 | 0.000 | 0.520 | 0.000 | 0.140 | 0.000 | 0.000 | 0.140 |
| 127 | 142 | 0.000 | 0.150 | 0.570 | 0.000 | 0.000 | 0.000 | 0.140 | 0.140 |
| 143 | 143 | 0.000 | 0.000 | 0.530 | 0.050 | 0.140 | 0.140 | 0.000 | 0.140 |
| 91 | 144 | 0.000 | 0.100 | 0.570 | 0.050 | 0.140 | 0.140 | 0.000 | 0.000 |
| 38 | 145 | 0.000 | 0.290 | 0.520 | 0.000 | 0.140 | 0.000 | 0.050 | 0.000 |
| 123 | 146 | 0.000 | 0.000 | 0.570 | 0.050 | 0.140 | 0.000 | 0.100 | 0.140 |
| 155 | 147 | 0.060 | 0.000 | 0.520 | 0.000 | 0.140 | 0.000 | 0.140 | 0.140 |
| 16 | 148 | 0.290 | 0.000 | 0.520 | 0.050 | 0.000 | 0.000 | 0.000 | 0.140 |
| 55 | 149 | 0.150 | 0.000 | 0.570 | 0.000 | 0.140 | 0.140 | 0.000 | 0.000 |
| 161 | 150 | 0.000 | 0.000 | 0.570 | 0.000 | 0.140 | 0.010 | 0.140 | 0.140 |
| 105 | 151 | 0.290 | 0.000 | 0.520 | 0.000 | 0.050 | 0.000 | 0.000 | 0.140 |
| 59 | 152 | 0.000 | 0.000 | 0.570 | 0.050 | 0.140 | 0.140 | 0.100 | 0.000 |
| 33 | 153 | 0.290 | 0.000 | 0.520 | 0.000 | 0.140 | 0.050 | 0.000 | 0.000 |
| 172 | 154 | 0.000 | 0.000 | 0.570 | 0.010 | 0.140 | 0.140 | 0.140 | 0.000 |
| 72 | 155 | 0.000 | 0.240 | 0.570 | 0.050 | 0.000 | 0.140 | 0.000 | 0.000 |
| 3 | 156 | 0.290 | 0.000 | 0.570 | 0.000 | 0.140 | 0.000 | 0.000 | 0.000 |
| 77 | 157 | 0.150 | 0.000 | 0.520 | 0.050 | 0.000 | 0.140 | 0.140 | 0.000 |
| 177 | 158 | 0.085 | 0.085 | 0.543 | 0.023 | 0.066 | 0.066 | 0.066 | 0.066 |
| 35 | 159 | 0.290 | 0.000 | 0.520 | 0.000 | 0.140 | 0.000 | 0.000 | 0.050 |
| 57 | 160 | 0.150 | 0.000 | 0.520 | 0.050 | 0.140 | 0.140 | 0.000 | 0.000 |
| 100 | 161 | 0.010 | 0.000 | 0.520 | 0.050 | 0.140 | 0.140 | 0.140 | 0.000 |
| 169 | 162 | 0.010 | 0.000 | 0.570 | 0.000 | 0.140 | 0.140 | 0.140 | 0.140 |
| 60 | 163 | 0.000 | 0.000 | 0.570 | 0.050 | 0.140 | 0.140 | 0.000 | 0.100 |
| 111 | 164 | 0.000 | 0.290 | 0.520 | 0.000 | 0.000 | 0.000 | 0.050 | 0.140 |
| 70 | 165 | 0.000 | 0.290 | 0.520 | 0.000 | 0.000 | 0.050 | 0.140 | 0.000 |
| 140 | 166 | 0.000 | 0.000 | 0.570 | 0.050 | 0.140 | 0.140 | 0.010 | 0.140 |
| 154 | 167 | 0.000 | 0.000 | 0.570 | 0.050 | 0.100 | 0.140 | 0.140 | 0.000 |
| 137 | 168 | 0.010 | 0.000 | 0.570 | 0.000 | 0.140 | 0.140 | 0.000 | 0.140 |
| 106 | 169 | 0.290 | 0.000 | 0.520 | 0.000 | 0.000 | 0.050 | 0.000 | 0.140 |
| 98 | 170 | 0.000 | 0.000 | 0.570 | 0.000 | 0.140 | 0.140 | 0.140 | 0.010 |

TABLE 2-continued 177 glass compositions (mol. fraction) formulated using design of experiments. The NM components are varied between 0 to 0.140 mol. fraction.

| Std. ORP# | Run | Si | Ca | Zn | Mg | La | Sr | Ti | Na |
|---|---|---|---|---|---|---|---|---|---|
| 79 | 171 | 0.000 | 0.000 | 0.570 | 0.050 | 0.140 | 0.000 | 0.140 | 0.100 |
| 30 | 172 | 0.000 | 0.290 | 0.570 | 0.050 | 0.000 | 0.000 | 0.090 | 0.000 |
| 85 | 173 | 0.150 | 0.000 | 0.570 | 0.000 | 0.000 | 0.140 | 0.140 | 0.000 |
| 103 | 174 | 0.000 | 0.000 | 0.530 | 0.050 | 0.140 | 0.140 | 0.140 | 0.000 |
| 110 | 175 | 0.000 | 0.290 | 0.520 | 0.000 | 0.000 | 0.050 | 0.000 | 0.140 |
| 130 | 176 | 0.100 | 0.000 | 0.570 | 0.050 | 0.000 | 0.140 | 0.000 | 0.140 |
| 136 | 177 | 0.000 | 0.000 | 0.520 | 0.000 | 0.140 | 0.140 | 0.060 | 0.140 |

The invention claimed is:

1. A particulate material comprising:
0.4-0.6 mole fraction $SiO_2$;
0.00-0.1 mole fraction $TiO_2$;
0.04-0.188 mole fraction $La_2O_3$;
0.008-0.290 mole fraction ZnO;
about 0.035 mote fraction $Na_3O$;
about 0.035 mole fraction MgO;
about 0.035 mole fraction SrO; and
about 0.035 mole fraction CaO.

2. The particulate material of claim 1 wherein $La_2O_3$ is present at 0.04 to 0.1 mole fraction.

3. The particulate material of claim 2 wherein $La_2O_3$ is present at 0.04 to 0.07 mole fraction.

4. The particulate material of claim 1 wherein $TiO_2$ is present at 0.017 to 0.05 mole fraction.

5. The particulate material of claim 1 wherein $SiO_2$ present at 0.5-0.57 mole fraction.

6. The particulate material of claim 1 wherein the particulate material is radiopaque.

7. The particulate material claim 1 wherein the particulate material is biocompatible.

8. The particulate material of claim 1 wherein said particulate material is degradable in vivo.

9. The particulate material of claim 8 wherein said particulate material degrades substantially in more than six months.

10. The particulate material of claim 1 further comprising a therapeutic component.

11. The particulate material of claim 10 wherein said therapeutic component is released under physiological conditions.

12. The particulate material of claim 1 having a Q-speciation of $Q^1$-$Q^3$.

13. The particulate material of claim 12 having a Q-speciation of $Q^1$.

14. The particulate material of claim 1 having an average diameter of 45-1180 μm.

15. The particulate material of claim 14 having an average diameter of 200-1000 μm.

16. The particulate material of claim 15 having an average diameter of 300-400 μm.

17. The particulate material of claim 15 having an average diameter of 500-710 μm.

18. The particulate material of claim 1 further comprising a polymeric coating.

19. The particulate material of claim 18 wherein said polymeric coating comprises poly(lactic-co-glycolic acid).

20. The particulate material of claim 18 wherein said polymeric coating comprises a poloxamer.

21. The particulate material of claim 20 wherein said polymeric coating comprises Pluronic F-127.

22. The particulate material of claim 18 further comprising a therapeutic component.

23. The particulate material of claim 22 wherein said therapeutic component is released under physiological conditions.

24. The particular material of claim 1 comprising no more than 0.1 mole fraction aluminosilicates, phosphates or a combination thereof.

25. The particulate material according to claim 1, wherein the particulate material consists of:
0.562 mole fraction $SiO_2$;
0.042 mole fraction $TiO_2$;
0.068 mole fraction $La_2O_3$;
0.035 mule fraction MgO;
0.035 mole fraction $Na_2O$;
0.188 mole fraction ZnO;
0.035 mole fraction CaO; and
0.035 mole fraction SrO.

26. The particulate material of claim 1, wherein the particulate material consists essentially of:
0.4-0.6 mote fraction $SiO_2$;
0.00-0.1 mole fraction $TiO_2$;
0.04-0.188 mole fraction $La_2O_3$;
0.008-0.290 mole fraction ZnO;
about 0.035 mole fraction $Na_2O$;
about 0.035 mole fraction MgO;
about 0.035 mole fraction SrO; and
about 0.035 mole fraction CaO.

27. The particulate material of claim 1, wherein the particulate material consists of:
0.4-0.6 mole fraction SiO2;
0.00-0.1 mole fraction TiO2;
0.04-0.188 mole fraction La2O3;
0.068-0.290 mole fraction ZnO; and
about 0.0435 mole fraction $Na_2O$;
about 0.035 mole fraction MgO;
about 0.035 mole fraction SrO; and
about 0.035 mole fraction CaO.

* * * * *

UNITED STATES PATENT AND TRADEMARK OFFICE
CERTIFICATE OF CORRECTION

PATENT NO. : 9,757,480 B2
APPLICATION NO. : 13/980316
DATED : September 12, 2017
INVENTOR(S) : Robert J. Abraham et al.

It is certified that error appears in the above-identified patent and that said Letters Patent is hereby corrected as shown below:

In the Specification
Column 19, Line 14, Delete "$SO^{4+}$" and insert --$Si^{4+}$--, therefor.

In the Claims
Column 31, Line 21, In Claim 1, Delete "0.008-0.290" and insert --0.068-0.290--, therefor.
Column 31, Line 22, In Claim 1, Delete "$Na_3O$" and insert --$Na_2O$--, therefor.
Column 32, Line 37, In Claim 26, Delete "0.008-0.290" and insert --0.068-0.290--, therefor.
Column 32, Line 47, In Claim 27, Delete "La2O3" and insert --$La_2O_3$--, therefor.

Signed and Sealed this
Twenty-seventh Day of February, 2018

Andrei Iancu
*Director of the United States Patent and Trademark Office*